US012662552B2

(12) United States Patent
Soeda et al.

(10) Patent No.: US 12,662,552 B2
(45) Date of Patent: Jun. 23, 2026

(54) ANTIBODY FOR NEUTRALIZING SUBSTANCE HAVING COAGULATION FACTOR VIII (F.VIII) FUNCTION-SUBSTITUTING ACTIVITY

(71) Applicant: Chugai Seiyaku Kabushiki Kaisha, Tokyo (JP)

(72) Inventors: Tetsuhiro Soeda, Kanagawa (JP); Jinki Hadano, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 818 days.

(21) Appl. No.: 17/923,997

(22) PCT Filed: May 21, 2021

(86) PCT No.: PCT/JP2021/019299
§ 371 (c)(1),
(2) Date: Nov. 8, 2022

(87) PCT Pub. No.: WO2021/235537
PCT Pub. Date: Nov. 25, 2021

(65) Prior Publication Data
US 2023/0183376 A1     Jun. 15, 2023

(30) Foreign Application Priority Data

May 22, 2020     (JP) ................................. 2020-089570

(51) Int. Cl.
| C07K 16/42 | (2006.01) |
| C12N 15/63 | (2006.01) |
| G01N 33/49 | (2006.01) |

(52) U.S. Cl.
CPC .......... C07K 16/4241 (2013.01); C12N 15/63 (2013.01); G01N 33/4905 (2013.01)

(58) Field of Classification Search
None
See application file for complete search history.

(56) References Cited

U.S. PATENT DOCUMENTS

2017/0275376 A1     9/2017   Igawa et al.

FOREIGN PATENT DOCUMENTS

| EP | 3 690 050 A1 | 8/2020 |
| WO | WO 2005/035756 | 4/2005 |
| WO | WO 2006/109592 | 10/2006 |
| WO | WO 2012/067176 | 5/2012 |
| WO | WO 2016/047652 | 3/2016 |
| WO | WO 2016/047656 | 3/2016 |
| WO | WO 2019/065795 | 4/2019 |

OTHER PUBLICATIONS

Mariuzza, R.A. etal. The Structural Basis of Antigen-Antibody Recognition1 Annu. Rev. Biophys. Biphys. Chem. 16:139-159, 1987.*

Maccallum et al. "Antibody-antigen interactions: contact analysis and binding site topography", Journal of Molecular Biology, 1996. vol. 262, pp. 732-745.*

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

Goel et al. Plasticity within the Antigen-Combining Site May Manifest as Molecular Mimicry in the Humoral Immune Response.1 J. Immunol. 173(12)7358-7367, 2004.*

Kahn et al. 'Adjustable Locks and Flexible Keys: Plasticity of Epitope-Paratope Interactions in Germline Antibodies.' J. Immunol. 192:5398-5405, 2014.*

Poosarla et al. 'Computational De Novo Design of Antibodies Binding to a Peptide With High Affinity.' Biotech. Bioeng. 114(6): 1331-1342, 2017.*

Nogami et al., "Routine measurements of factor VIII activity and inhibitor titer in the presence of emicizumab utilizing anti-idiotype monoclonal antibodies," J Thromb Haemost, Jul. 2018, 16(7):1383-1390.

Nogami et al., "A method to solve the issue of emicizumab's interference with FVIII:C and FVIII inhibitor titer assays," Haemophilia, 2016, 22(Suppl. 4):76-77.

Hardisty et al., "A One-stage Factor VIII (Antihaemophilic Globulin) Assay and its Use on Venous and Capillary Plasma," Thromb Diath Haemorrh, May 15, 1962, 7:215-228.

Kasper et al., "A More Uniform Measurement of Factor VIII Inhibitors," Thromb Diath Haemorrh, Dec. 15, 1975, 34(3):869-872.

Kitazawa et al., "A bispecific antibody to factors IXa and X restores factor VIII hemostatic activity in a hemophilia A model," Nat Med, Oct. 2012, 18(10):1570-1574. doi: 10.1038/nm.2942. Epub Sep. 30, 2012.

Manco-Johnson et al., "Prophylaxis versus Episodic Treatment to Prevent Joint Disease in Boys with Severe Hemophilia," N Engl J Med, Aug. 9, 2007, 357(6):535-544.

Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2):206-213.

Oldenburg, "Prophylaxis in bleeding disorders," Thromb Res, Jan. 2011, 127 Suppl 1:S14-S17. doi: 10.1016/j.thromres.2010.10.005. Epub Nov. 26, 2010.

(Continued)

*Primary Examiner* — Nora M Rooney

(74) *Attorney, Agent, or Firm* — Fish & Richardson P.C.

(57) ABSTRACT

Production was attempted for antibodies that neutralize the activity of a bispecific antibody having F.VIII function-substituting activity, for use in a method for measuring the reactivity of F.VIII in the presence of a bispecific antibody having F.VIII function-substituting activity. As a result, it was discovered that by using the produced antibodies, F.VIII activity in the plasma of a hemophilia A patient can be evaluated accurately by performing APTT-based one-stage clotting assay on a wide range of bispecific antibodies having F.VIII function-substituting activity. It was also discovered that F.VIII inhibitor titer in the plasma of a hemophilia A patient carrying F.VIII inhibitor can be evaluated accurately by APTT-based Bethesda assay.

16 Claims, 1 Drawing Sheet

Specification includes a Sequence Listing.

(56) References Cited

OTHER PUBLICATIONS

Sampei et al., "Identification and Multidimensional Optimization of an Asymmetric Bispecific IgG Antibody Mimicking the Function of Factor VIII Cofactor Activity," PLoS One, 2013, 8(2):e57479, 13 pages. doi: 10.1371/journal.pone.0057479. Epub Feb. 28, 2013.

Verbruggen et al., "The Nijmegen Modification of the Bethesda Assay for Factor VIII: C Inhibitors: Improved Specificity and Reliability," Thromb Haemost, Feb. 1995, 73(2):247-251.

Wagenvoord et al., "Development of a Simple Chromogenic Factor VIII Assay for Clinical Use," Haemostasis, 1989, 19(4):196-204.

International Search Report in PCT/JP2021/019299, mailed Jun. 22, 2021, 2 pages.

* cited by examiner

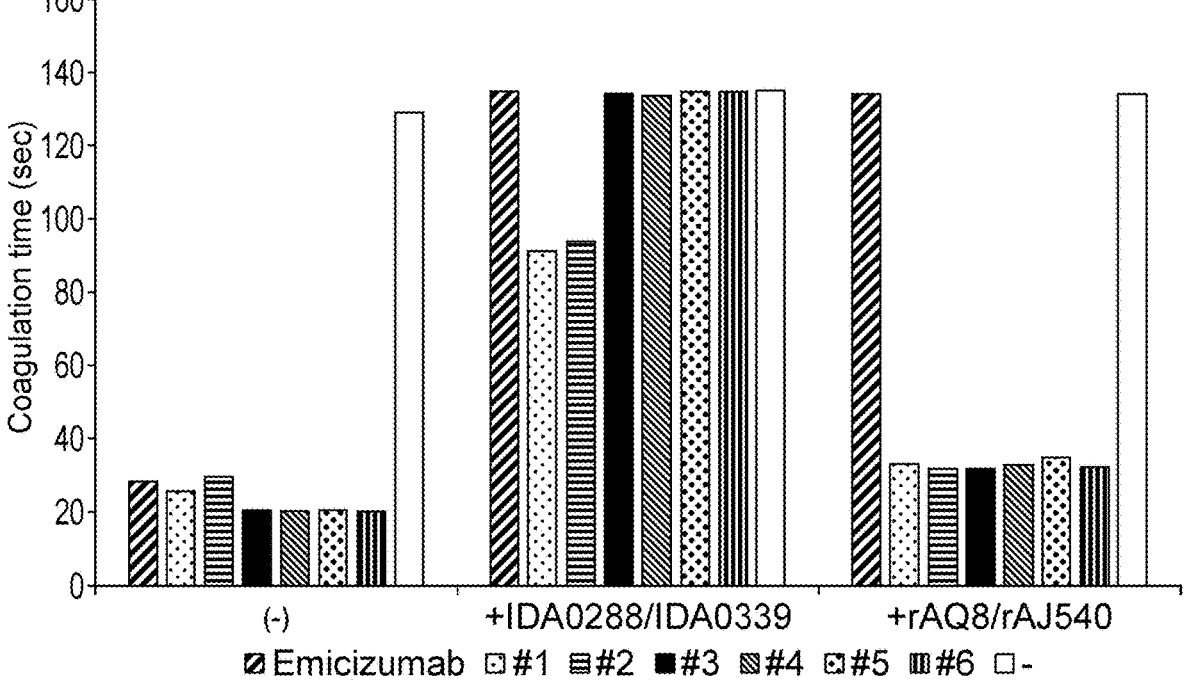

ANTIBODY FOR NEUTRALIZING SUBSTANCE HAVING COAGULATION FACTOR VIII (F.VIII) FUNCTION-SUBSTITUTING ACTIVITY

CROSS-REFERENCE TO RELATED APPLICATIONS

This application is the National Stage of International Application No. PCT/JP2021/019299, filed on May 21, 2021, which claims the benefit of Japanese Application No. 2020-089570, filed on May 22, 2020.

SEQUENCE LISTING

This application contains a Sequence Listing that has been submitted electronically as an ASCII text file named SequenceListing.txt. The ASCII text file, created on Nov. 8, 2022, is 283,964 bytes in size. The material in the ASCII text file is hereby incorporated by reference in its entirety.

TECHNICAL FIELD

The present invention relates to antibodies that neutralize a substance having an activity of functionally substituting for coagulation factor VIII (F.VIII). The present invention also relates to antibodies to be used for methods of measuring reactivity of F.VIII in the presence of a substance having F.VIII function-substituting activity.

BACKGROUND ART

Hemophilia is a hemorrhagic disease caused by a congenital defect or dysfunction of F.VIII or coagulation factor IX (F.IX). The former is called hemophilia A and the latter is called hemophilia B. Both of these genes are located on the X chromosome; and since they are X-chromosome-linked recessive genetic abnormalities, 99% or more of those who develop the disease are men. It is known that the prevalence rate is approximately one in 10,000 male births, and the ratio between hemophilia A and hemophilia B is approximately 5:1.

The main bleeding sites in hemophilia patients include intraarticular, intramuscular, subcutaneous, intraoral, intracranial, digestive tract, intranasal, and such. Among them, repeated intraarticular bleeding can develop into hemophilic arthropathy accompanied by articular disorders and difficulty in walking, which eventually may require joint replacement. Therefore, it is a major factor that lowers the QOL of hemophilia patients.

The severity of hemophilia correlates well with the F.VIII activity or F.IX activity in blood. Patients with a coagulation factor activity of less than 1% are classified as severe, patients with an activity of 1% or more to less than 5% are classified as moderate, and patients with an activity of 5% or more and less than 40% are classified as mild. Patients with severe symptoms, accounting for approximately half of hemophilia patients, exhibit bleeding symptoms several times a month if they do not receive the later-described preventive replacement therapy, and this frequency is markedly high compared to those of moderately symptomatic patients and mildly symptomatic patients.

In addition to hemophilia and acquired hemophilia, von Willebrand's disease caused by functional abnormality or deficiency of von Willebrand factor (vWF) is known to be a related bleeding abnormality. vWF is not only necessary for platelets to undergo normal adhesion to the subendothelial tissues at lesion sites of vascular walls, but it is also necessary for forming a complex with F.VIII and keeping F.VIII in the blood at a normal level. In von Willebrand's disease patients, these functions are decreased, leading to hemostasis dysfunction.

For prevention and/or treatment of bleeding in hemophilia patients, blood coagulation factors purified from plasma or those produced by genetic engineering techniques are mainly used. In severe hemophilia patients, maintaining the F.VIII activity or F.IX activity in the blood at 1% or more by F.VIII or F.IX replacement therapy are considered to be effective for preventing manifestation of bleeding symptoms (NPL 1, 2). On the other hand, in hemophilia patients, particularly severe hemophilia patients, antibodies against F.VIII or F.IX which are called inhibitors may be generated. When such inhibitors are generated, the effect of the coagulation factor formulation is blocked by the inhibitors. As a result, neutralization treatment using large amounts of the coagulation factor formulation, or bypass treatment using a complex concentrate or an activated coagulation factor VII formulation (F.VIIa formulation) is carried out.

Measurement of the F.VIII activity in hemophilia A is carried out mainly by one-stage clotting assay based on activated partial thromboplastin time (APTT) (NPL 3) and chromogenic assay which is a system reconstructed using a purified coagulation factor (NPL 4).

Measurement of the F.VIII inhibitor titer in hemophilia A is carried out mainly by Bethesda assay or Nijmegen Bethesda assay (NPL 5, 6).

Recently, a bispecific antibody, Emicizumab, that binds to both F.IX and/or activated coagulation factor IX (F.IXa) and coagulation factor X (F.X) and/or activated blood coagulation factor X (F.Xa), and substitutes for the cofactor function of F.VIII or more specifically, the function of promoting F.X activation by F.IXa, was found (NPL 7, 8; PTL 1, 2, 3). The bispecific antibody functionally substitutes for F.VIII to improve the decrease in coagulation reaction due to F.VIII deficiency or functional abnormality. For example, with respect to thrombin production and APTT which are indicators of the coagulation reaction, the bispecific antibody shortens the APTT of plasma derived from a hemophilia A patient regardless of the presence of a F.VIII inhibitor, and increases the production of thrombin. The APTT-shortening effect of the bispecific antibody was remarkable in comparison to F.VIII. This is because F.VIII in plasma shows cofactor activity only after activation by activated factor X (F.Xa) or thrombin, whereas the above-mentioned bispecific antibody does not need such activation process, and for that reason, exhibits the cofactor function more quickly.

Furthermore, antibodies against F.IXa Fab and against F.X Fab of the bispecific antibody were obtained, and the concentrations of the bispecific antibody in plasma samples from animal testing were determined (NPL 9).

The present bispecific antibody substitutes for the cofactor function of F.VIII, thus affecting the assay system that measures the reactivity of F.VIII itself. For example, when measuring the plasma F.VIII activity by APTT-based one-stage clotting assay to diagnose the severity of hemophilia A or to monitor the pharmacological activity of a F.VIII formulation in a F.VIII formulation-administered patient, the action of promoting the shortening of coagulation time of the bispecific antibody strongly interferes in the presence of the bispecific antibody, which greatly impairs the accuracy of measurement. Furthermore, when determining the plasma F.VIII inhibitor titer by APTT-based Bethesda assay, the action of promoting the shortening of coagulation time of the bispecific antibody strongly interferes in the presence of the bispecific antibody, which greatly impairs the accuracy of measurement. That is, in patients administered with the bispecific antibody, the F.VIII activity and F.VIII inhibitor titer cannot be accurately measured. Therefore, methods that enable measurement of the F.VIII activity and F.VIII inhibitor titer even in the presence of a bispecific antibody are desired.

Antibodies against Emicizumab, a bispecific antibody which substitutes for the function of promoting F.X activation by F.IXa, and methods that enable measurement of F.VIII activity and F.VIII inhibitor titer using those antibodies were also developed (PTL 4 and 5).

The bispecific antibody which substitutes for the function of promoting F.X activation by F.IXa is not limited to Emicizumab and novel bispecific antibodies whose function has been further improved are also known (PTL 6).

CITATION LIST

Patent Literature

[PTL 1] WO2005/035756
[PTL 2] WO2006/109592
[PTL 3] WO2012/067176
[PTL 4] WO2016/047656
[PTL 5] WO2016/047652
[PTL 6] WO2019/065795

Non-Patent Literature

[NPL 1] N Engl J Med. 2007; 357(6):535-44
[NPL 2] Thromb Res. 2011; 127 (suppl1):S14-7
[NPL 3] Thromb Diath Haemorrh. 1962 May 15; 7:215-28
[NPL 4] Haemostasis. 1989 19:196-204.
[NPL 5] Thromb Diath Haemorrh. 1975; 34(3):869-72
[NPL 6] Thromb Haemost. 1995 February; 73(2):247-51.
[NPL 7] Nat Med. 2012; 18(10):1570-74
[NPL 8] PLoS One. 2013; 8(2):e57479.
[NPL 9] J Thromb Haemost. 2014; 12(2):206-13 Supporting Information

SUMMARY OF INVENTION

Technical Problem

As described above, in patients with hemorrhagic diseases such as hemophilia who received a bispecific antibody, there was a problem in that it was difficult to measure the F.VIII activity and the F.VIII inhibitor titer accurately due to presence of the bispecific antibody in the plasma samples. The invention of this application solves such problems. The objective of the present invention is to provide antibodies that neutralize a substance having an activity of functionally substituting for coagulation factor VIII (F.VIII), which can be used in a method for accurately measuring the reactivity of F.VIII in the presence of the substance having F.VIII function-substituting activity, such as a method of accurately measuring F.VIII activity and F.VIII inhibitor titer. Furthermore, an objective of the present invention is to provide methods, kits, and such for measuring the reactivity of F.VIII, such as F.VIII activity and F.VIII inhibitor titer, in the presence of a substance having F.VIII function-substituting activity.

Solution to Problem

To solve the above-mentioned problems, the present inventors focused on test items for measuring the reactivity of F.VIII, and produced a substance that neutralizes the activity of a bispecific antibody having F.VIII function-substituting activity, and examined whether accuracy of evaluation of F.VIII reactivity was maintained even in the presence of the bispecific antibody. As a result, the present inventors discovered that by using a neutralizing antibody against a bispecific antibody having F.VIII function-substituting activity at a concentration that allows sufficient neutralization of the bispecific antibody, the F.VIII activity in the plasma of hemophilia A patients can be evaluated accurately by APTT-based one-stage clotting assay. The present inventors also succeeded in discovering a kit comprising a neutralizing antibody against a bispecific antibody having a F.VIII function-substituting activity, which can be used for the present measurement. Furthermore, the present inventors discovered that the antibodies of the present invention neutralize a wide range of bispecific antibodies. The present invention is based on these findings and provides the following.

[1] An antibody that neutralizes a bispecific antibody that binds to coagulation factor IX and/or activated coagulation factor IX and coagulation factor X and/or activated blood coagulation factor X, wherein the bispecific antibody is selected from the group consisting of (a) to (t) below:

(a) a bispecific antibody which comprises a first antibody heavy chain variable region comprising the amino acid sequence of SEQ ID NO: 83, a first antibody light chain variable region comprising the amino acid sequence of SEQ ID NO: 88, a second antibody heavy chain variable region comprising the amino acid sequence of SEQ ID NO: 100, and a second antibody light chain variable region comprising the amino acid sequence of SEQ ID NO: 111;

(b) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 100, and a second antibody light chain variable region comprising the amino acid sequence of SEQ ID NO: 111;

(c) a bispecific antibody which comprises a first antibody heavy chain variable region comprising the amino acid sequence of SEQ ID NO: 85, a first antibody light chain variable region comprising the amino acid sequence of SEQ ID NO: 90, a second antibody heavy chain variable region comprising the amino acid sequence of SEQ ID NO: 101, and a second antibody light chain variable region comprising the amino acid sequence of SEQ ID NO: 112;

(d) a bispecific antibody which comprises a first antibody heavy chain variable region comprising the amino acid sequence of SEQ ID NO: 85, a first antibody light chain variable region comprising the amino acid sequence of SEQ ID NO: 91, a second antibody heavy chain variable region comprising the amino acid sequence of SEQ ID NO: 101, and a second antibody light chain variable region comprising the amino acid sequence of SEQ ID NO: 112;

(e) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 102, and a second antibody light chain variable region comprising the amino acid sequence of SEQ ID NO: 113;

(f) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 103, and a second antibody light chain variable region comprising the amino acid sequence of SEQ ID NO: 114;

(g) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 101, and a second antibody light chain variable region comprising the amino acid sequence of SEQ ID NO: 112;

(h) a bispecific antibody which comprises a first antibody heavy chain variable region comprising the amino acid sequence of SEQ ID NO: 86, a first antibody light chain variable region comprising the amino acid sequence of SEQ ID NO: 92, a second antibody heavy chain variable region comprising the amino acid sequence of SEQ ID NO: 101, and a second antibody light chain variable region comprising the amino acid sequence of SEQ ID NO: 112;

(i) a bispecific antibody which comprises a first antibody heavy chain variable region comprising the amino acid sequence of SEQ ID NO: 86, a first antibody light chain variable region comprising the amino acid sequence of SEQ ID NO: 93, a second antibody heavy chain variable region comprising the amino acid sequence of SEQ ID NO: 101, and a second antibody light chain variable region comprising the amino acid sequence of SEQ ID NO: 112;

(j) a bispecific antibody which comprises a first antibody heavy chain variable region comprising the amino acid sequence of SEQ ID NO: 86, a first antibody light chain variable region comprising the amino acid sequence of SEQ ID NO: 93, a second antibody heavy chain variable region comprising the amino acid sequence of SEQ ID NO: 104, and a second antibody light chain variable region comprising the amino acid sequence of SEQ ID NO: 115;

(k) a bispecific antibody which comprises a first antibody heavy chain variable region comprising the amino acid sequence of SEQ ID NO: 86, a first antibody light chain variable region comprising the amino acid sequence of SEQ ID NO: 94, a second antibody heavy chain variable region comprising the amino acid sequence of SEQ ID NO: 104, and a second antibody light chain variable region comprising the amino acid sequence of SEQ ID NO: 115;

(l) a bispecific antibody which comprises a first antibody heavy chain variable region comprising the amino acid sequence of SEQ ID NO: 86, a first antibody light chain variable region comprising the amino acid sequence of SEQ ID NO: 94, a second antibody heavy chain variable region comprising the amino acid sequence of SEQ ID NO: 105, and a second antibody light chain variable region comprising the amino acid sequence of SEQ ID NO: 116;

(m) a bispecific antibody which comprises a first antibody heavy chain variable region comprising the amino acid sequence of SEQ ID NO: 86, a first antibody light chain variable region comprising the amino acid sequence of SEQ ID NO: 95, a second antibody heavy chain variable region comprising the amino acid sequence of SEQ ID NO: 104, and a second antibody light chain variable region comprising the amino acid sequence of SEQ ID NO: 115;

(n) a bispecific antibody which comprises a first antibody heavy chain variable region comprising the amino acid sequence of SEQ ID NO: 86, a first antibody light chain variable region comprising the amino acid sequence of SEQ ID NO: 95, a second antibody heavy chain variable region comprising the amino acid sequence of SEQ ID NO: 105, and a second antibody light chain variable region comprising the amino acid sequence of SEQ ID NO: 116;

(o) a bispecific antibody which comprises a first antibody heavy chain variable region comprising the amino acid sequence of SEQ ID NO: 87, a first antibody light chain variable region comprising the amino acid sequence of SEQ ID NO: 96, a second antibody heavy chain variable region comprising the amino acid sequence of SEQ ID NO: 106, and a second antibody light chain variable region comprising the amino acid sequence of SEQ ID NO: 117;

(p) a bispecific antibody which comprises a first antibody heavy chain variable region comprising the amino acid sequence of SEQ ID NO: 86, a first antibody light chain variable region comprising the amino acid sequence of SEQ ID NO: 97, a second antibody heavy chain variable region comprising the amino acid sequence of SEQ ID NO: 107, and a second antibody light chain variable region comprising the amino acid sequence of SEQ ID NO: 118;

(q) a bispecific antibody which comprises a first antibody heavy chain variable region comprising the amino acid sequence of SEQ ID NO: 87, a first antibody light chain variable region comprising the amino acid sequence of SEQ ID NO: 98, a second antibody heavy chain variable region comprising the amino acid sequence of SEQ ID NO: 106, and a second antibody light chain variable region comprising the amino acid sequence of SEQ ID NO: 117;

(r) a bispecific antibody which comprises a first antibody heavy chain variable region comprising the amino acid sequence of SEQ ID NO: 87, a first antibody light chain variable region comprising the amino acid sequence of SEQ ID NO: 98, a second antibody heavy chain variable region comprising the amino acid sequence of SEQ ID NO: 108, and a second antibody light chain variable region comprising the amino acid sequence of SEQ ID NO: 119;

(s) a bispecific antibody which comprises a first antibody heavy chain variable region comprising the amino acid sequence of SEQ ID NO: 87, a first antibody light chain variable region comprising the amino acid sequence of SEQ ID NO: 96, a second antibody heavy chain variable region comprising the amino acid sequence of SEQ ID NO: 109, and a second antibody light chain variable region comprising the amino acid sequence of SEQ ID NO: 120; and (t) a bispecific antibody which comprises a first antibody heavy chain variable region comprising the amino acid sequence of SEQ ID NO: 122, a first antibody light chain variable region comprising the amino acid sequence of SEQ ID NO: 99, a second antibody heavy chain variable region comprising the amino acid sequence of SEQ ID NO: 110, and a second antibody light chain variable region comprising the amino acid sequence of SEQ ID NO: 121.

[2] The neutralizing antibody of [1], wherein the bispecific antibody further comprises:

(1) a first antibody heavy chain constant region comprising the amino acid sequence of SEQ ID NO: 139 and a first antibody light chain constant region comprising the amino acid sequence of SEQ ID NO: 140, and (2) a second antibody heavy chain constant region comprising the amino acid sequence of SEQ ID NO: 141 and a second antibody light chain constant region comprising the amino acid sequence of SEQ ID NO: 142.

[3] An antibody that neutralizes a bispecific antibody that binds to coagulation factor IX and/or activated coagulation factor IX and coagulation factor X and/or activated blood coagulation factor X, wherein the bispecific antibody is selected from the group consisting of (a) to (t) below:

(a) a bispecific antibody which comprises a first antibody heavy chain comprising the amino acid sequence of SEQ ID NO: 143, a first antibody light chain comprising the amino acid sequence of SEQ ID NO: 149, a second antibody heavy chain comprising the amino acid sequence of SEQ ID NO: 161, and a second antibody light chain comprising the amino acid sequence of SEQ ID NO: 172;

(b) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 161, and a second antibody light chain comprising the amino acid sequence of SEQ ID NO: 172;

(c) a bispecific antibody which comprises a first antibody heavy chain comprising the amino acid sequence of SEQ ID NO: 145, a first antibody light chain comprising the amino acid sequence of SEQ ID NO: 151, a second antibody heavy chain comprising the amino acid sequence of SEQ ID NO: 162, and a second antibody light chain comprising the amino acid sequence of SEQ ID NO: 173;

(d) a bispecific antibody which comprises a first antibody heavy chain comprising the amino acid sequence of SEQ ID NO: 145, a first antibody light chain comprising the amino acid sequence of SEQ ID NO: 152, a second antibody heavy chain comprising the amino acid sequence of SEQ ID NO: 162, and a second antibody light chain comprising the amino acid sequence of SEQ ID NO: 173;

(e) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 163, and a second antibody light chain comprising the amino acid sequence of SEQ ID NO: 174;

(f) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 164, and a second antibody light chain comprising the amino acid sequence of SEQ ID NO: 175;

(g) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 162, and a second antibody light chain comprising the amino acid sequence of SEQ ID NO: 173;

(h) a bispecific antibody which comprises a first antibody heavy chain comprising the amino acid sequence of SEQ ID NO: 146, a first antibody light chain comprising the amino acid sequence of SEQ ID NO: 153, a second antibody heavy chain comprising the amino acid sequence of SEQ ID NO: 162, and a second antibody light chain comprising the amino acid sequence of SEQ ID NO: 173;

(i) a bispecific antibody which comprises a first antibody heavy chain comprising the amino acid sequence of SEQ ID NO: 146, a first antibody light chain comprising the amino acid sequence of SEQ ID NO: 154, a second antibody heavy chain comprising the amino acid sequence of SEQ ID NO: 162, and a second antibody light chain comprising the amino acid sequence of SEQ ID NO: 173;

(j) a bispecific antibody which comprises a first antibody heavy chain comprising the amino acid sequence of SEQ ID NO: 146, a first antibody light chain comprising the amino acid sequence of SEQ ID NO: 154, a second antibody heavy chain comprising the amino acid sequence of SEQ ID NO: 165, and a second antibody light chain comprising the amino acid sequence of SEQ ID NO: 176;

(k) a bispecific antibody which comprises a first antibody heavy chain comprising the amino acid sequence of SEQ ID NO: 146, a first antibody light chain comprising the amino acid sequence of SEQ ID NO: 155, a second antibody heavy chain comprising the amino acid sequence of SEQ ID NO: 165, and a second antibody light chain comprising the amino acid sequence of SEQ ID NO: 176;

(l) a bispecific antibody which comprises a first antibody heavy chain comprising the amino acid sequence of SEQ ID NO: 146, a first antibody light chain comprising the amino acid sequence of SEQ ID NO: 155, a second antibody heavy chain comprising the amino acid sequence of SEQ ID NO: 166, and a second antibody light chain comprising the amino acid sequence of SEQ ID NO: 177;

(m) a bispecific antibody which comprises a first antibody heavy chain comprising the amino acid sequence of SEQ ID NO: 146, a first antibody light chain comprising the amino acid sequence of SEQ ID NO: 156, a second antibody heavy chain comprising the amino acid sequence of SEQ ID NO: 165, and a second antibody light chain comprising the amino acid sequence of SEQ ID NO: 176;

(n) a bispecific antibody which comprises a first antibody heavy chain comprising the amino acid sequence of SEQ ID NO: 146, a first antibody light chain comprising the amino acid sequence of SEQ ID NO: 156, a second antibody heavy chain comprising the amino acid sequence of SEQ ID NO: 166, and a second antibody light chain comprising the amino acid sequence of SEQ ID NO: 177;

(o) a bispecific antibody which comprises a first antibody heavy chain comprising the amino acid sequence of SEQ ID NO: 147, a first antibody light chain comprising the amino acid sequence of SEQ ID NO: 157, a second antibody heavy chain comprising the amino acid sequence of SEQ ID NO: 167, and a second antibody light chain comprising the amino acid sequence of SEQ ID NO: 178;

(p) a bispecific antibody which comprises a first antibody heavy chain comprising the amino acid sequence of SEQ ID NO: 146, a first antibody light chain comprising the amino acid sequence of SEQ ID NO: 158, a second antibody heavy chain comprising the amino acid sequence of SEQ ID NO: 168, and a second antibody light chain comprising the amino acid sequence of SEQ ID NO: 179;

(q) a bispecific antibody which comprises a first antibody heavy chain comprising the amino acid sequence of SEQ ID NO: 147, a first antibody light chain comprising the amino acid sequence of SEQ ID NO: 159, a second antibody heavy chain comprising the amino acid sequence of SEQ ID NO: 167, and a second antibody light chain comprising the amino acid sequence of SEQ ID NO: 178;

(r) a bispecific antibody which comprises a first antibody heavy chain comprising the amino acid sequence of SEQ ID NO: 147, a first antibody light chain comprising the amino acid sequence of SEQ ID NO: 159, a second antibody heavy chain comprising the amino acid sequence of SEQ ID NO: 169, and a second antibody light chain comprising the amino acid sequence of SEQ ID NO: 180;

(s) a bispecific antibody which comprises a first antibody heavy chain comprising the amino acid sequence of SEQ ID NO: 147, a first antibody light chain comprising the amino acid sequence of SEQ ID NO: 157, a second antibody heavy chain comprising the amino acid sequence of SEQ ID NO: 170, and a second antibody light chain comprising the amino acid sequence of SEQ ID NO: 181; and (t) a bispecific antibody which comprises a first antibody heavy chain comprising the amino acid sequence of SEQ ID NO: 148, a first antibody light chain comprising the amino acid sequence of SEQ ID NO: 160, a second antibody heavy chain comprising the amino acid sequence of SEQ ID NO: 171, and a second antibody light chain comprising the amino acid sequence of SEQ ID NO: 182.

[4] An antibody that comprises a heavy chain variable region comprising the amino acid sequence of SEQ ID NO: 1 and a light chain variable region comprising the amino acid sequence of SEQ ID NO: 2, or an antibody that binds to an epitope overlapping with or identical to an epitope bound by said antibody.

[5] An antibody that comprises an antibody heavy chain comprising the amino acid sequence of SEQ ID NO: 131 and an antibody light chain comprising the amino acid sequence of SEQ ID NO: 132, or an antibody that binds to an epitope overlapping with or identical to an epitope bound by said antibody.

[6] An antibody that comprises a heavy chain variable region comprising the amino acid sequence of SEQ ID NO: 3 and a light chain variable region comprising the amino acid sequence of SEQ ID NO: 4, or an antibody that binds to an epitope overlapping with or identical to an epitope bound by said antibody.

[7] An antibody that comprises an antibody heavy chain comprising the amino acid sequence of SEQ ID NO: 135 and an antibody light chain comprising the amino acid sequence of SEQ ID NO: 136, or an antibody that binds to an epitope overlapping with or identical to an epitope bound by said antibody.

[8] A nucleic acid encoding the antibody of any one of [1] to [7].

[9] A vector in which the nucleic acid of [8] has been inserted.

[10] A cell comprising the nucleic acid of [8] or the vector of [9].

[11] A method for producing an antibody, which comprises the step of culturing the cell of [10].

[12] A composition comprising the antibody of [4] and/or the antibody of [6].

[13] A composition comprising the antibody of [5] and/or the antibody of [7].

[14] A method for measuring the reactivity of coagulation factor VIII, which comprises the step of bringing the following (1) into contact with the following (2):

(1) a blood-derived sample comprising a bispecific antibody that binds to coagulation factor IX and/or activated coagulation factor IX and coagulation factor X and/or activated blood coagulation factor X; and (2) the antibody of [4] or [5] and/or the antibody of [6] or [7].

[15] A method for measuring the reactivity of coagulation factor VIII, which comprises the step of bringing the following (1) into contact with the following (2):

(1) a blood-derived sample comprising a bispecific antibody that binds to coagulation factor IX and/or activated coagulation factor IX and coagulation factor X and/or activated blood coagulation factor X; and (2) the composition of [12] or [13].

[16] A kit for use in the method of [15], which comprises the composition of [12] or [13].

Furthermore, the present invention provides the following [101] to [106].

[101] An antibody that binds to a Fab comprising an antigen-binding site that binds to coagulation factor IX and/or activated coagulation factor IX, wherein a) the heavy chain variable region comprises CDR1 that consists of the amino acid sequence of SEQ ID NO: 12, CDR2 that consists of the amino acid sequence of SEQ ID NO: 13, and CDR3 that consists of the amino acid sequence of SEQ ID NO: 14; and b) the light chain variable region comprises CDR1 that consists of the amino acid sequence of SEQ ID NO: 18, CDR2 that consists of the amino acid sequence of SEQ ID NO: 19, and CDR3 that consists of the amino acid sequence of SEQ ID NO: 20.

[102] An antibody that binds to a Fab comprising an antigen-binding site that binds to coagulation factor X and/or activated coagulation factor X, wherein a) the heavy chain variable region comprises CDR1 that consists of the amino acid sequence of SEQ ID NO: 24, CDR2 that consists of the amino acid sequence of SEQ ID NO: 25, and CDR3 that consists of the amino acid sequence of SEQ ID NO: 26; and b) the light chain variable region comprises CDR1 that consists of the amino acid sequence of SEQ ID NO: 30, CDR2 that consists of the amino acid sequence of SEQ ID NO: 31, and CDR3 that consists of the amino acid sequence of SEQ ID NO: 32.

[103] A nucleic acid encoding the antibody of any one of [101] to [102].

[104] A vector in which the nucleic acid of [103] has been inserted.

[105] A cell comprising the nucleic acid of [103] or the vector of [104].

[106] A method for producing an antibody, which comprises the step of culturing the cell of [105].

Effects of the Invention

The present invention provides antibodies that can be used for measuring F.VIII activity and F.VIII inhibitor titer without being influenced by the activity of a substance having F.VIII function-substituting activity. Examples of a substance having F.VIII-substituting activity include bispecific antibodies that bind to F.IX and/or F.IXa and F.X and/or F.Xa. By using the antibodies provided in the present invention, F.VIII activity and F.VIII inhibitor titer can be measured accurately, even when a substance having F.VIII function-substituting activity is present in a sample.

BRIEF DESCRIPTION OF DRAWINGS

FIG. 1 shows the results of one-stage clotting assay performed under neutralization of the anti-F.IXa/F.X bispecific antibody using IDA0288 and IDA0339, or rAQ8 and rAJ540.

DESCRIPTION OF EMBODIMENTS

The invention of the present application relates to antibodies that neutralize a substance having an activity of functionally substituting for F.VIII and nucleic acids encoding the antibodies. The antibodies of the present invention can be used for measuring F.VIII activity and F.VIII inhibitor titer in a sample without being influenced by the activity of a substance having F.VIII function-substituting activity, when measuring the reactivity of F.VIII in the presence of the substance having F.VIII function-substituting activity.

The nucleic acids in the present invention include those in the form of DNA and those in the form of mRNA.

F.VIII Function-Substituting Activity

F.VIII is one of a series of molecules involved in blood coagulation, which demonstrates cofactor activity when it is activated by thrombin or F.Xa and promotes the F.X activation reaction by F.IXa.

A substance having F.VIII function-substituting activity in the present invention can be rephrased as a substance having a F.VIII-like activity. In the present invention, the phrase "functionally substituting for F.VIII" means that F.X activation by F.IXa is promoted (F.Xa generation by F.IXa is promoted). More specifically, in the present invention, the phrase "functionally substituting for F.VIII" means recognizing F.IX and/or F.IXa, and F.X and/or F.Xa, and promoting activation of F.X by F.IXa (promoting F.Xa generation by F.IXa). The activity of promoting F.Xa generation can be evaluated using, for example, a measurement system composed of F.IXa, F.X, synthetic substrate S-2222 (synthetic substrate of F.Xa), and phospholipids. Such a measurement system shows correlation between the severity of the disease and clinical symptoms in hemophilia A cases (Rosen S, Andersson M, Blomba¨ck M et al. Clinical applications of a chromogenic substrate method for determination of F.VIII activity. Thromb Haemost 1985; 54: 811-23).

A preferred embodiment of a substance having an activity of substituting the function of F.VIII in the present invention includes, for example, a bispecific antibody that binds to F.IX and/or F.IXa, and to F.X and/or F.Xa. Such an antibody can be obtained according to methods described, for example, in WO2005/035756, WO2006/109592, WO2012/067176, and WO2019/065795. The bispecific antibody of the present invention includes antibodies described in these documents.

A preferred bispecific antibody includes, for example, Emicizumab (Q499-z121/J327-z119/L404-k) which is a bispecific antibody described in a patent literature (WO 2012/067176) (a bispecific antibody in which the heavy chain consisting of the amino acid sequence of SEQ ID NO: 9 and the light chain of SEQ ID NO: 10 are associated, and the heavy chain consisting of the amino acid sequence of SEQ ID NO: 11 and the light chain of SEQ ID NO: 10 are associated), hBS23 (Q153-G4k/J142-G4h/L180-k) (a bispecific antibody in which the heavy chain consisting of the amino acid sequence of SEQ ID NO: 36 and the light chain of SEQ ID NO: 38 are associated, and the heavy chain consisting of the amino acid sequence of SEQ ID NO: 37 and the light chain of SEQ ID NO: 38 are associated), and any one of the following antibodies (a) to (t), which are bispecific antibodies described in a patent literature (WO 2019/065795):

(a) a bispecific antibody which comprises a first antibody heavy chain variable region comprising the amino acid sequence of SEQ ID NO: 83, a first antibody light chain variable region comprising the amino acid sequence of SEQ ID NO: 88, a second antibody heavy chain variable region comprising the amino acid sequence of SEQ ID NO: 100, and a second antibody light chain variable region comprising the amino acid sequence of SEQ ID NO: 111;

(b) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 100, and a second antibody light chain variable region comprising the amino acid sequence of SEQ ID NO: 111;

(c) a bispecific antibody which comprises a first antibody heavy chain variable region comprising the amino acid sequence of SEQ ID NO: 85, a first antibody light chain variable region comprising the amino acid sequence of SEQ ID NO: 90, a second antibody heavy chain variable region comprising the amino acid sequence of SEQ ID NO: 101, and a second antibody light chain variable region comprising the amino acid sequence of SEQ ID NO: 112;

(d) a bispecific antibody which comprises a first antibody heavy chain variable region comprising the amino acid sequence of SEQ ID NO: 85, a first antibody light chain variable region comprising the amino acid sequence of SEQ ID NO: 91, a second antibody heavy chain variable region comprising the amino acid sequence of SEQ ID NO: 101, and a second antibody light chain variable region comprising the amino acid sequence of SEQ ID NO: 112;

(e) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 102, and a second antibody light chain variable region comprising the amino acid sequence of SEQ ID NO: 113;

(f) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 103, and a second antibody light chain variable region comprising the amino acid sequence of SEQ ID NO: 114;

(g) a bispecific antibody which comprises a first antibody heavy chain variable region comprising the amino acid sequence of SEQ ID NO: 84, a first antibody light chain variable region comprising the amino acid sequence of SEQ ID NO: 89, a second antibody heavy chain variable region comprising the amino acid sequence of SEQ ID NO: 101, and a second antibody light chain variable region comprising the amino acid sequence of SEQ ID NO: 112;

(h) a bispecific antibody which comprises a first antibody heavy chain variable region comprising the amino acid sequence of SEQ ID NO: 86, a first antibody light chain variable region comprising the amino acid sequence of SEQ ID NO: 92, a second antibody heavy chain variable region comprising the amino acid sequence of SEQ ID NO: 101, and a second antibody light chain variable region comprising the amino acid sequence of SEQ ID NO: 112;

(i) a bispecific antibody which comprises a first antibody heavy chain variable region comprising the amino acid sequence of SEQ ID NO: 86, a first antibody light chain variable region comprising the amino acid sequence of SEQ ID NO: 93, a second antibody heavy chain variable region comprising the amino acid sequence of SEQ ID NO: 101, and a second antibody light chain variable region comprising the amino acid sequence of SEQ ID NO: 112;

(j) a bispecific antibody which comprises a first antibody heavy chain variable region comprising the amino acid sequence of SEQ ID NO: 86, a first antibody light chain variable region comprising the amino acid sequence of SEQ ID NO: 93, a second antibody heavy chain variable region comprising the amino acid sequence of SEQ ID NO: 104, and a second antibody light chain variable region comprising the amino acid sequence of SEQ ID NO: 115;

(k) a bispecific antibody which comprises a first antibody heavy chain variable region comprising the amino acid sequence of SEQ ID NO: 86, a first antibody light chain variable region comprising the amino acid sequence of SEQ ID NO: 94, a second antibody heavy chain variable region comprising the amino acid sequence of SEQ ID NO: 104, and a second antibody light chain variable region comprising the amino acid sequence of SEQ ID NO: 115;

(l) a bispecific antibody which comprises a first antibody heavy chain variable region comprising the amino acid sequence of SEQ ID NO: 86, a first antibody light chain variable region comprising the amino acid sequence of SEQ ID NO: 94, a second antibody heavy chain variable region comprising the amino acid sequence of SEQ ID NO: 105, and a second antibody light chain variable region comprising the amino acid sequence of SEQ ID NO: 116;

(m) a bispecific antibody which comprises a first antibody heavy chain variable region comprising the amino acid sequence of SEQ ID NO: 86, a first antibody light chain variable region comprising the amino acid sequence of SEQ ID NO: 95, a second antibody heavy chain variable region comprising the amino acid sequence of SEQ ID NO: 104, and a second antibody light chain variable region comprising the amino acid sequence of SEQ ID NO: 115;

(n) a bispecific antibody which comprises a first antibody heavy chain variable region comprising the amino acid sequence of SEQ ID NO: 86, a first antibody light chain variable region comprising the amino acid sequence of SEQ ID NO: 95, a second antibody heavy chain variable region comprising the amino acid sequence of SEQ ID NO: 105, and a second antibody light chain variable region comprising the amino acid sequence of SEQ ID NO: 116;

(o) a bispecific antibody which comprises a first antibody heavy chain variable region comprising the amino acid sequence of SEQ ID NO: 87, a first antibody light chain variable region comprising the amino acid sequence of SEQ ID NO: 96, a second antibody heavy chain variable region comprising the amino acid sequence of SEQ ID NO: 106, and a second antibody light chain variable region comprising the amino acid sequence of SEQ ID NO: 117;

(p) a bispecific antibody which comprises a first antibody heavy chain variable region comprising the amino acid sequence of SEQ ID NO: 86, a first antibody light chain variable region comprising the amino acid sequence of SEQ ID NO: 97, a second antibody heavy chain variable region comprising the amino acid sequence of SEQ ID NO: 107, and a second antibody light chain variable region comprising the amino acid sequence of SEQ ID NO: 118;

(q) a bispecific antibody which comprises a first antibody heavy chain variable region comprising the amino acid sequence of SEQ ID NO: 87, a first antibody light chain variable region comprising the amino acid sequence of SEQ ID NO: 98, a second antibody heavy chain variable region comprising the amino acid sequence of SEQ ID NO: 106, and a second antibody light chain variable region comprising the amino acid sequence of SEQ ID NO: 117;

(r) a bispecific antibody which comprises a first antibody heavy chain variable region comprising the amino acid sequence of SEQ ID NO: 87, a first antibody light chain variable region comprising the amino acid sequence of SEQ ID NO: 98, a second antibody heavy chain variable region comprising the amino acid sequence of SEQ ID NO: 108, and a second antibody light chain variable region comprising the amino acid sequence of SEQ ID NO: 119;

(s) a bispecific antibody which comprises a first antibody heavy chain variable region comprising the amino acid sequence of SEQ ID NO: 87, a first antibody light chain variable region comprising the amino acid sequence of SEQ ID NO: 96, a second antibody heavy chain variable region comprising the amino acid sequence of SEQ ID NO: 109, and a second antibody light chain variable region comprising the amino acid sequence of SEQ ID NO: 120; and (t) a bispecific antibody which comprises a first antibody heavy chain variable region comprising the amino acid sequence of SEQ ID NO: 122, a first antibody light chain variable region comprising the amino acid sequence of SEQ ID NO: 99, a second antibody heavy chain variable region comprising the amino acid sequence of SEQ ID NO: 110, and a second antibody light chain variable region comprising the amino acid sequence of SEQ ID NO: 121.

The bispecific antibodies of (a) to (t) may further comprise (1) a first antibody heavy chain constant region comprising the amino acid sequence of SEQ ID NO: 139 and/or a first antibody light chain constant region comprising the amino acid sequence of SEQ ID NO: 140, and/or (2) a second antibody heavy chain constant region comprising the amino acid sequence of SEQ ID NO: 141 and/or a second antibody light chain constant region comprising the amino acid sequence of SEQ ID NO: 142.

A preferred bispecific antibody of the present invention is more preferably, for example, any one of the antibodies of the following (a1) to (t1), which are bispecific antibodies described in a patent literature (WO 2019/065795). In the following antibodies, the first antibody heavy chain is associated with the first antibody light chain, and the second antibody heavy chain is associated with the second antibody light chain:

(a1) a bispecific antibody which comprises a first antibody heavy chain comprising the amino acid sequence of SEQ ID NO: 143, a first antibody light chain comprising the amino acid sequence of SEQ ID NO: 149, a second antibody heavy chain comprising the amino acid sequence of SEQ ID NO: 161, and a second antibody light chain comprising the amino acid sequence of SEQ ID NO: 172;

(b1) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 161, and a second antibody light chain comprising the amino acid sequence of SEQ ID NO: 172;

(c1) a bispecific antibody which comprises a first antibody heavy chain comprising the amino acid sequence of SEQ ID NO: 145, a first antibody light chain comprising the amino acid sequence of SEQ ID NO: 151, a second antibody heavy chain comprising the amino acid sequence of SEQ ID NO: 162, and a second antibody light chain comprising the amino acid sequence of SEQ ID NO: 173;

(d1) a bispecific antibody which comprises a first antibody heavy chain comprising the amino acid sequence of SEQ ID NO: 145, a first antibody light chain comprising the amino acid sequence of SEQ ID NO: 152, a second antibody heavy chain comprising the amino acid sequence of SEQ ID NO: 162, and a second antibody light chain comprising the amino acid sequence of SEQ ID NO: 173;

(e1) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 163, and a second antibody light chain comprising the amino acid sequence of SEQ ID NO: 174;

(f1) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 164, and a second antibody light chain comprising the amino acid sequence of SEQ ID NO: 175;

(g1) a bispecific antibody which comprises a first antibody heavy chain comprising the amino acid sequence of SEQ ID NO: 144, a first antibody light chain comprising the amino acid sequence of SEQ ID NO: 150, a second antibody heavy chain comprising the amino acid sequence of SEQ ID NO: 162, and a second antibody light chain comprising the amino acid sequence of SEQ ID NO: 173;

(h1) a bispecific antibody which comprises a first antibody heavy chain comprising the amino acid sequence of SEQ ID NO: 146, a first antibody light chain comprising the amino acid sequence of SEQ ID NO: 153, a second antibody heavy chain comprising the amino acid sequence of SEQ ID NO: 162, and a second antibody light chain comprising the amino acid sequence of SEQ ID NO: 173;

(i1) a bispecific antibody which comprises a first antibody heavy chain comprising the amino acid sequence of SEQ ID NO: 146, a first antibody light chain comprising the amino acid sequence of SEQ ID NO: 154, a second antibody heavy chain comprising the amino acid sequence of SEQ ID NO: 162, and a second antibody light chain comprising the amino acid sequence of SEQ ID NO: 173;

(j1) a bispecific antibody which comprises a first antibody heavy chain comprising the amino acid sequence of SEQ ID NO: 146, a first antibody light chain comprising the amino acid sequence of SEQ ID NO: 154, a second antibody heavy chain comprising the amino acid sequence of SEQ ID NO: 165, and a second antibody light chain comprising the amino acid sequence of SEQ ID NO: 176;

(k1) a bispecific antibody which comprises a first antibody heavy chain comprising the amino acid sequence of SEQ ID NO: 146, a first antibody light chain comprising the amino acid sequence of SEQ ID NO: 155, a second antibody heavy chain comprising the amino acid sequence of SEQ ID NO: 165, and a second antibody light chain comprising the amino acid sequence of SEQ ID NO: 176;

(l1) a bispecific antibody which comprises a first antibody heavy chain comprising the amino acid sequence of SEQ ID NO: 146, a first antibody light chain comprising the amino acid sequence of SEQ ID NO: 155, a second antibody heavy chain comprising the amino acid sequence of SEQ ID NO: 166, and a second antibody light chain comprising the amino acid sequence of SEQ ID NO: 177;

(m1) a bispecific antibody which comprises a first antibody heavy chain comprising the amino acid sequence of SEQ ID NO: 146, a first antibody light chain comprising the amino acid sequence of SEQ ID NO: 156, a second antibody heavy chain comprising the amino acid sequence of SEQ ID NO: 165, and a second antibody light chain comprising the amino acid sequence of SEQ ID NO: 176;

(n1) a bispecific antibody which comprises a first antibody heavy chain comprising the amino acid sequence of SEQ ID NO: 146, a first antibody light chain comprising the amino acid sequence of SEQ ID NO: 156, a second antibody heavy chain comprising the amino acid sequence of SEQ ID NO: 166, and a second antibody light chain comprising the amino acid sequence of SEQ ID NO: 177;

(o1) a bispecific antibody which comprises a first antibody heavy chain comprising the amino acid sequence of SEQ ID NO: 147, a first antibody light chain comprising the amino acid sequence of SEQ ID NO: 157, a second antibody heavy chain comprising the amino acid sequence of SEQ ID NO: 167, and a second antibody light chain comprising the amino acid sequence of SEQ ID NO: 178;

(p1) a bispecific antibody which comprises a first antibody heavy chain comprising the amino acid sequence of SEQ ID NO: 146, a first antibody light chain comprising the amino acid sequence of SEQ ID NO: 158, a second antibody heavy chain comprising the amino acid sequence of SEQ ID NO: 168, and a second antibody light chain comprising the amino acid sequence of SEQ ID NO: 179;

(q1) a bispecific antibody which comprises a first antibody heavy chain comprising the amino acid sequence of SEQ ID NO: 147, a first antibody light chain comprising the amino acid sequence of SEQ ID NO: 159, a second antibody heavy chain comprising the amino acid sequence of SEQ ID NO: 167, and a second antibody light chain comprising the amino acid sequence of SEQ ID NO: 178;

(r1) a bispecific antibody which comprises a first antibody heavy chain comprising the amino acid sequence of SEQ ID NO: 147, a first antibody light chain comprising the amino acid sequence of SEQ ID NO: 159, a second antibody heavy chain comprising the amino acid sequence of SEQ ID NO: 169, and a second antibody light chain comprising the amino acid sequence of SEQ ID NO: 180;

(s1) a bispecific antibody which comprises a first antibody heavy chain comprising the amino acid sequence of SEQ ID NO: 147, a first antibody light chain comprising the amino acid sequence of SEQ ID NO: 157, a second antibody heavy chain comprising the amino acid sequence of SEQ ID NO: 170, and a second antibody light chain comprising the amino acid sequence of SEQ ID NO: 181; and (t1) a bispecific antibody which comprises a first antibody heavy chain comprising the amino acid sequence of SEQ ID NO: 148, a first antibody light chain comprising the amino acid sequence of SEQ ID NO: 160, a second antibody heavy chain comprising the amino acid sequence of SEQ ID NO: 171, and a second antibody light chain comprising the amino acid sequence of SEQ ID NO: 182.

Neutralization

"Neutralization" in a substance that neutralizes the substance having an activity of functionally substituting for F.VIII in the present invention refers to, for example, complete or partial inhibition of the F.VIII function-substituting activity of a substance that has F.VIII function-substituting activity. For example, when the substance having the activity of functionally substituting for F.VIII is an antibody, complete or partial inhibition of the F.VIII function-substituting activity may be accomplished by completely or partially inhibiting binding of the antibody to the antigen, but is not limited thereto.

Antibodies

When the substance having an activity of functionally substituting for F.VIII is a bispecific antibody that binds to F.IX and/or F.IXa and to F.X and/or F.Xa, examples of antibodies that bind to the substance having an activity of functionally substituting for F.VIII include antibodies selected from the group consisting of antibodies that bind to a Fab containing an antigen-binding site that binds to F.IX, antibodies that bind to a Fab containing an antigen-binding site that binds to F.IXa, antibodies that bind to a Fab containing an antigen-binding site that binds to F.X, antibodies that bind to a Fab containing an antigen-binding site that binds to F.Xa, and bispecific antibodies that bind to a Fab containing an antigen-binding site that binds to F.IX and/or F.IXa and to a Fab containing an antigen-binding site that binds to F.X and/or F.Xa. The above-mentioned antibodies can be used individually or in multiple combinations, and they can be used in combination as compositions or as kits. For example, it is possible to use multiple antibodies that bind to a Fab containing an antigen-binding site that binds to one type of antigen, for example, multiple types of antibodies that bind to a Fab containing an antigen-binding site that binds to F.IX. For example, when the substance having an activity of functionally substituting for F.VIII is a bispecific antibody that binds to F.IX and/or F.IXa and to F.X and/or F.Xa, the antibodies may be used in the following combinations:

(a) an antibody that binds to a Fab containing an antigen-binding site that binds to F.IX and an antibody that binds to a Fab containing an antigen-binding site that binds to F.X;

(b) an antibody that binds to a Fab containing an antigen-binding site that binds to F.IXa and an antibody that binds to a Fab containing an antigen-binding site that binds to F.X;

(c) an antibody that binds to a Fab containing an antigen-binding site that binds to F.IX and an antibody that binds to a Fab containing an antigen-binding site that binds to F.IXa; and (d) an antibody that binds to a Fab containing an antigen-binding site that binds to F.IX, an antibody that binds to a Fab containing an antigen-binding site that binds to F.X, and an antibody that binds to a Fab containing an antigen-binding site that binds to F.IXa;

That is, the present invention relates to compositions or kits comprising a combination of neutralizing antibodies described herein.

An example of an antibody that binds to a Fab containing an antigen-binding site that binds to F.IX and/or F.IXa includes the IDA0288 antibody. The nucleotide sequences of the variable regions and the amino acid sequences predicted from them were analyzed by GENETYX Ver. 9 (GENETYX CORPORATION).

The amino acid sequence and the nucleic acid sequence of the heavy chain variable region of IDA0288 are indicated by the following SEQ ID NOs:

amino acid sequence: SEQ ID NO: 1; and nucleic acid sequence: SEQ ID NO: 5.

The amino acid sequence and the nucleic acid sequence of the light chain variable region of IDA0288 are indicated by the following SEQ ID NOs:

amino acid sequence: SEQ ID NO: 2; and nucleic acid sequence: SEQ ID NO: 6.

The amino acid sequences and the nucleic acid sequences of the heavy chain CDRs 1 to 3 of IDA0288 are indicated by the following SEQ ID NOs:

CDR1 amino acid sequence: SEQ ID NO: 12;

CDR2 amino acid sequence: SEQ ID NO: 13;

CDR3 amino acid sequence: SEQ ID NO: 14;

CDR1 nucleic acid sequence: SEQ ID NO: 15;

CDR2 nucleic acid sequence: SEQ ID NO: 16; and

CDR3 nucleic acid sequence: SEQ ID NO: 17.

The amino acid sequences and the nucleic acid sequences of the light chain CDRs 1 to 3 of IDA0288 are indicated by the following SEQ ID NOs:

CDR1 amino acid sequence: SEQ ID NO: 18;
CDR2 amino acid sequence: SEQ ID NO: 19;
CDR3 amino acid sequence: SEQ ID NO: 20;
CDR1 nucleic acid sequence: SEQ ID NO: 21;
CDR2 nucleic acid sequence: SEQ ID NO: 22; and
CDR3 nucleic acid sequence: SEQ ID NO: 23.

The amino acid sequence and the nucleic acid sequence of the antibody heavy chain constant region of IDA0288 are indicated by the following SEQ ID NOs:

amino acid sequence: SEQ ID NO: 123; and
nucleic acid sequence: SEQ ID NO: 125.

The amino acid sequence and the nucleic acid sequence of the antibody light chain constant region of IDA0288 are indicated by the following SEQ ID NOs:

amino acid sequence: SEQ ID NO: 124; and
nucleic acid sequence: SEQ ID NO: 126.

The amino acid sequence and the nucleic acid sequence of the antibody heavy chain of IDA0288 are indicated by the following SEQ ID NOs:

amino acid sequence: SEQ ID NO: 131; and
nucleic acid sequence: SEQ ID NO: 133.

The amino acid sequence and the nucleic acid sequence of the antibody light chain of IDA0288 are indicated by the following SEQ ID NOs:

amino acid sequence: SEQ ID NO: 132; and
nucleic acid sequence: SEQ ID NO: 134.

An example of an antibody that binds to a Fab containing an antigen-binding site that binds to F.X and/or F.Xa includes the IDA0339 antibody. The nucleotide sequences of the variable regions and the amino acid sequences predicted therefrom were analyzed by GENETYX Ver. 9 (GENETYX CORPORATION).

The amino acid sequence and the nucleic acid sequence of the heavy chain variable region of IDA0339 are indicated by the following SEQ ID NOs:

amino acid sequence: SEQ ID NO: 3; and
nucleic acid sequence: SEQ ID NO: 7.

The amino acid sequence and the nucleic acid sequence of the light chain variable region of IDA0339 are indicated by the following SEQ ID NOs:

amino acid sequence: SEQ ID NO: 4; and
nucleic acid sequence: SEQ ID NO: 8.

The amino acid sequences and the nucleic acid sequences of the heavy chain CDRs 1 to 3 of IDA0339 are indicated by the following SEQ ID NOs:

CDR1 amino acid sequence: SEQ ID NO: 24;
CDR2 amino acid sequence: SEQ ID NO: 25;
CDR3 amino acid sequence: SEQ ID NO: 26;
CDR1 nucleic acid sequence: SEQ ID NO: 27;
CDR2 nucleic acid sequence: SEQ ID NO: 28; and
CDR3 nucleic acid sequence: SEQ ID NO: 29.

The amino acid sequences and the nucleic acid sequences of the light chain CDRs 1 to 3 of IDA0339 are indicated by the following SEQ ID NOs:

CDR1 amino acid sequence: SEQ ID NO: 30;
CDR2 amino acid sequence: SEQ ID NO: 31;
CDR3 amino acid sequence: SEQ ID NO: 32;
CDR1 nucleic acid sequence: SEQ ID NO: 33;
CDR2 nucleic acid sequence: SEQ ID NO: 34; and
CDR3 nucleic acid sequence: SEQ ID NO: 35.

The amino acid sequence and the nucleic acid sequence of the antibody heavy chain constant region of IDA0339 are indicated by the following SEQ ID NOs:

amino acid sequence: SEQ ID NO: 127; and nucleic acid sequence: SEQ ID NO: 129.

The amino acid sequence and the nucleic acid sequence of the antibody light chain constant region of IDA0339 are indicated by the following SEQ ID NOs:

amino acid sequence: SEQ ID NO: 128; and
nucleic acid sequence: SEQ ID NO: 130.

The amino acid sequence and the nucleic acid sequence of the antibody heavy chain of IDA0339 are indicated by the following SEQ ID NOs:

amino acid sequence: SEQ ID NO: 135; and
nucleic acid sequence: SEQ ID NO: 137.

The amino acid sequence and the nucleic acid sequence of the antibody light chain of IDA0288 are indicated by the following SEQ ID NOs:

amino acid sequence: SEQ ID NO: 136; and
nucleic acid sequence: SEQ ID NO: 138.

The term "antibody" is used in the broadest sense, and may be monoclonal antibodies, polyclonal antibodies, dimers, multimers, multispecific antibodies (for example, bispecific antibodies), antibody derivatives, and modified antibody products (Miller K et al. J Immunol. 2003, 170(9), 4854-61) as long as they display a desired biological activity. The antibodies may be mouse antibodies, human antibodies, humanized antibodies, chimeric antibodies, or those derived from another species, or they may be artificially synthesized antibodies. The antibodies disclosed herein can be of any type (for example, IgG, IgE, IgM, IgD, and IgA), class (for example, IgG1, IgG2, IgG3, IgG4, IgA1 and IgA2) or subclass of immunoglobulin molecules. The immunoglobulins can be derived from any species (for example, human, mouse, or rabbit). The terms "antibody", "immune globulin" and "immunoglobulin" are used interchangeably in a broad sense.

The term "antibody derivative" includes a portion of an antibody, preferably an antibody variable region, or at least an antigen-binding region of an antibody. Antibody derivatives include, for example, Fab, Fab', F(ab')2, Fv fragments, linear antibodies, and single-chain antibodies (scFv), sc(Fv)$_2$, Fab$_3$, domain antibodies (dAb) (WO2004/058821, WO2003/002609), diabodies, triabodies, tetrabodies, minibodies, and multispecific antibodies formed from antibody derivatives, but are not limited thereto. Here, "Fab" is constructed from a single light chain and the CH1 domain and variable region of a single heavy chain. Furthermore, "Fv" is the smallest antibody derivative, and includes a complete antigen-recognizing region and an antigen-binding region. The antibody derivative may be, for example, a fusion between an IgG antibody and Fc. For example, one can refer to Example 2 in U.S. Pat. No. 5,641,870 specification; Zapata G et al. Protein Eng. 1995, 8(10), 1057-1062; Olafsen T et al. Protein Eng. Design & Sel. 2004, 17(4): 315-323; Holliger P et al. Nat. Biotechnol. 2005, 23(9): 1126-36; Fischer N et al. Pathobiology. 2007, 74(1): 3-14; Shen J et al. J Immunol Methods. 2007, 318, 65-74; and Wu et al. Nat Biotechnol. 2007, 25(11), 1290-7.

Examples of modified antibody products may include antibodies linked to various molecules such as polyethylene glycol (PEG). Antibodies of the present invention include such modified antibody products. The substance to be linked is not limited in the modified antibody products of the present invention. To yield such modified antibody products, chemical modifications can be made to the obtained antibodies. Such methods are already established in this field.

"Bispecific" antibodies refer to antibodies having variable regions that recognize different epitopes, where the regions are within the same antibody molecule. Bispecific antibodies may be antibodies that recognize two or more different antigens or antibodies that recognize two or more different epitopes on the same antigen. Bispecific antibodies may include not only whole antibodies but antibody derivatives. Antibodies of the present invention also include bispecific antibodies. Herein, anti-F.IXa/F.X bispecific antibody and bispecific antibody that binds to F.IXa and F.X are used synonymously.

Methods for Producing Genetically Engineered Antibodies

Recombinant antibodies produced by using genetic engineering techniques can be used as the antibodies. Recombinant antibodies can be obtained by cloning DNAs encoding the antibodies from hybridomas or antibody-producing cells such as sensitized lymphocytes that produce antibodies, inserting them into vectors, and then introducing them into hosts (host cells) to produce the antibodies.

The antibodies include human antibodies, mouse antibodies, and rat antibodies, and their origin is not limited. They may also be genetically modified antibodies such as chimeric antibodies and humanized antibodies.

Methods for obtaining human antibodies are known. For example, transgenic animals carrying the entire repertoire of human antibody genes can be immunized with antigens of interest to obtain human antibodies of interest (see International Publication WO 93/12227, WO 92/03918, WO 94/02602, WO 94/25585, WO 96/34096, and WO 96/33735).

Genetically modified antibodies can be produced using known methods. Specifically, for example, chimeric antibodies comprise heavy chain and light chain variable regions of an immunized animal antibody, and heavy chain and light chain constant regions of a human antibody. Chimeric antibodies can be obtained by linking DNAs encoding the variable regions of the antibody derived from the immunized animal, with DNAs encoding the constant regions of a human antibody, inserting this into an expression vector, and then introducing it into a host to produce the antibodies.

Humanized antibodies are modified antibodies that are also referred to as reshaped human antibodies. A humanized antibody is constructed by transferring the CDRs of an antibody derived from an immunized animal to the complementarity determining regions of a human antibody. Conventional genetic recombination techniques for such purposes are known (see European Patent Application Publication No. EP 239400; International Publication No. WO 96/02576; Sato K et al., Cancer Research 1993, 53: 851-856; International Publication No. WO 99/51743).

Bispecific antibodies are antibodies that have specificity to two different antigens.

While bispecific antibodies are not limited to those of the IgG type, for example, IgG-type bispecific antibodies can be secreted from a hybrid hybridoma (quadroma) produced by fusing two types of hybridomas that produce IgG antibodies (Milstein C. et al., Nature 1983, 305: 537-540). They can also be secreted by introducing the light chain and heavy chain genes constituting the two types of IgGs of interest, a total of four types of genes, into cells to co-express the genes.

In this case, by introducing suitable amino acid substitutions to the CH3 regions of the heavy chains, IgGs having a heterogeneous combination of heavy chains can be preferentially secreted (Ridgway J B et al. Protein Engineering 1996, 9: 617-621; Merchant A M et al. Nature Biotechnology 1998, 16: 677-681; WO 2006/106905; Davis J H et al. Protein Eng Des Sel. 2010, 4: 195-202).

Regarding the light chains, since the diversity of light chain variable regions is lower than that of heavy chain variable regions, one can expect to obtain common light chain that can confer binding ability to both heavy chains. The bispecific antibodies of the present invention may be antibodies comprising common light chains. Bispecific IgGs can be efficiently expressed by introducing the gene of the common light chain and both heavy chains into cells.

Epitopes

Antibodies which are an embodiment of substances that neutralize the substance having an activity of functionally substituting for F.VIII of in present invention include antibodies that bind to an epitope overlapping with an epitope bound by the antibodies described above, and preferably antibodies that bind to the same epitope.

Whether an antibody recognizes an epitope overlapping with or identical to an epitope that is recognized by another antibody can be confirmed by competition between the two antibodies against the epitope. Competition between the antibodies can be evaluated by competitive binding assays using means such as enzyme-linked immunosorbent assay (ELISA), fluorescence energy transfer method (FRET), and fluorometric microvolume assay technology (FMAT (Registered trademark)). The amount of antibodies bound to an antigen indirectly correlate with the binding ability of candidate competitor antibodies (test antibodies) that competitively bind to the same or overlapping epitope. In other words, as the amount of or the affinity of test antibodies against the same or overlapping epitope increases, the amount of antibodies bound to the antigen decreases, and the amount of test antibodies bound to the antigen increases. Specifically, the appropriately labeled antibodies and test antibodies are simultaneously added to the antigens, and then the bound antibodies are detected using the label. The amount of the antibodies bound to the antigen can be easily determined by labeling the antibodies in advance. This label is not particularly limited, and the labeling method is selected according to the assay technique used. Specific examples of the labeling method include fluorescent labeling, radiolabeling, and enzyme labeling.

Herein, the "antibody that binds to the overlapping epitope" or "antibody that binds to the same/identical epitope" refers to a test antibody that can reduce the amount of binding of the labeled antibody by at least 50% at a concentration that is usually 100 times higher, preferably 80 times higher, more preferably 50 times higher, even more preferably 30 times higher, and still more preferably 10 times higher than a concentration of the non-labeled antibody at which binding of the non-labeled antibody reduces the amount of binding of the labeled antibody by 50% (IC$_{50}$). The epitope recognized by the antibody can be analyzed by methods known to those skilled in the art, and for example, it can be performed by Western blotting and such.

In the present invention, in the case of a neutralizing antibody against an antibody having an antigen-binding site that binds to F.IX and/or F.IXa, an antibody that binds to an epitope overlapping with or identical to an epitope bound by the neutralizing antibody can be specified by measuring its activities of binding with the anti-F.IX side of the antibody Emicizumab (Q499-z121/L404-k) and with the QT15 antibody which is an anti-F.IX antibody.

In the present invention, in the case of a neutralizing antibody against an antibody having an antigen-binding site that binds to F.X and/or F.Xa, an antibody that binds to an epitope overlapping with or identical to an epitope bound by the neutralizing antibody can be specified by measuring its activities of binding with the anti-F.X side of the antibody Emicizumab (J327-z119/L404-k) and with the JT13 antibody which is an anti-F.X antibody.

In the composition of the present invention comprising an antibody, an antibody that binds to an epitope overlapping with or identical to an epitope bound by the neutralizing antibody of the present invention can be specified by measuring its binding with Emicizumab and with a mixed composition of the QT15 antibody and the JT13 antibody.

Antibody Production Methods

Antibodies of the present invention can be produced by methods known to those skilled in the art. Specifically, DNA encoding the antibody of interest is inserted into an expression vector. Insertion into an expression vector is carried out such that the expression will take place under the control of expression regulatory regions such as enhancers and promoters. Next, host cells are transformed using this expression vector to express the antibodies. Appropriate combinations of the host and expression vector can be used in this step. The method of producing an antibody in the present invention may include the step of culturing the above-discussed host cells. Host cells may be cultured by methods known to those skilled in the art.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for using the vectors for the purpose of producing the antibody. For example, when the host is *E. coli* such as JM109, DH5α, HB101, or XL1-Blue, the expression vectors indispensably have a promoter that permits efficient expression in *E. coli*, for example, lacZ promoter (Ward et al., Nature (1989) 341, 544-546; and FASEB J (1992) 6, 2422-2427), araB promoter (Better et al., Science (1988) 240, 1041-1043), or T7 promoter. Examples of such vectors include the vectors mentioned above as well as pGEX-5X-1 (manufactured by Pharmacia), "QIAexpress system" (manufactured by QIA-GEN), pEGFP, and pET (in this case, the host is preferably BL21 expressing T7 RNA polymerase).

The vectors may contain a signal sequence for polypeptide secretion. Signal sequence for polypeptide secretion known to those skilled in the art can be used, and in the case of production in the periplasm of *E. coli*, for example, pelB signal sequence (Lei, S. P. et al., J. Bacteriol. (1987) 169, 4397) can be used. The vectors can be transferred to the host cells using, for example, calcium chloride methods or electroporation methods.

In addition to the *E. coli* expression vectors, examples of the vectors for producing the antibody of the present invention include mammal-derived expression vectors (e.g., pcDNA3 (manufactured by Invitrogen Corp.), pEGF-BOS (Nucleic Acids. Res. 1990, 18(17), p 5322), pEF, and pCDM8), insect cell-derived expression vectors (e.g., "Bac-to-BAC baculovirus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "*Pichia* Expression Kit" (manufactured by Invitrogen Corp.), pNV11, and SP-Q01), and *Bacillus subtilis*-derived expression vectors (e.g., pPL608 and pKTH50).

For the purpose of expression in animal cells such as CHO cells, COS cells, or NIH3T3 cells, the vectors indispensably have a promoter necessary for intracellular expression, for example, SV40 promoter (Mulligan et al., Nature (1979)

277, 108), MMTV-LTR promoter, EF1α promoter (Mizushima et al., Nucleic Acids Res (1990) 18, 5322), CAG promoter (Gene (1991) 108, 193), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, pOPRSV, and pOP13.

An exemplary method intended to stably express the gene and increase the number of intracellular gene copies involves transfecting CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having a gene which expresses an SV40 T antigen on their chromosomes to transform the cells with vectors having a replication origin of SV40 (pcD, etc.). Also, a replication origin derived from polyomavirus, adenovirus, bovine papillomavirus (BPV), or the like may be used. The expression vectors for increasing the number of gene copies in a host cell system can additionally contain a selection marker such as an aminoglycoside transferase (APH) gene, a thymidine kinase (TK) gene, an *E. coli* xanthine guanine phosphoribosyltransferase (Ecogpt) gene, or a dihydrofolate reductase (dhfr) gene.

The present invention also provides such vectors in which nucleic acids encoding the antibodies described herein have been inserted. The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Furthermore, the present invention provides an isolated nucleic acid encoding an antibody of the present invention. Such nucleic acid may encode an amino acid sequence comprising the light chain variable region and/or an amino acid sequence comprising the heavy chain variable region of the antibody (for example, an antibody light chain and/or heavy chain). An isolated nucleic acid encoding an antibody may be inserted into one or more vectors for further cloning and/or expression in a host cell. Such nucleic acid may be readily isolated and sequenced by conventional procedures (for example, by using oligo-nucleic acid probes that bind specifically to genes encoding the heavy and/or light chains of the antibody).

The present invention also relates to a cell that comprises a nucleic acid encoding an antibody of the present specification or a vector comprising the nucleic acid. Herein, "cell" refers to cells into which an exogenous nucleic acid has been introduced (including the progeny of such cells). Cells of the present invention include "transformants" and "transformed cells", which include the primary transformed cell and progeny derived therefrom regardless of the number of passages. Progeny may not be completely identical in nucleic acid content to a parent cell, and may contain mutations. Also included are mutant progenies having the same function or biological activity as those used when screening or selecting the originally transformed cells. Herein, the cell comprises (for example, the cell has been transformed with):

(1) a vector that comprises a nucleic acid encoding an
      amino acid sequence comprising the light chain variable region and/or an amino acid sequence comprising the heavy chain variable region of the antibody, or (2) a first vector that comprises a nucleic acid encoding an amino acid sequence comprising the light chain variable region of the antibody and a second vector that comprises a nucleic acid encoding an amino acid sequence comprising the heavy chain variable region of the antibody.

In the present invention, the host may be eukaryotic (for example, a CHO cell or lymphocyte (for example, Y0, NS0, or SP20 cell)).

The antibodies of the present invention obtained by the methods described herein can be isolated from inside host cells or from outside of the cells (the medium, or such), and purified to practically pure and homogeneous antibodies. The antibodies can be separated and purified by methods routinely used for separating and purifying antibodies, and the type of method is not limited. For example, the antibodies can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid-chromatography, for example, HPLC and FPLC. Columns used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The obtained antibodies can be purified to homogeneity. Separation and purification of the antibodies can be performed using separation and purification methods generally used for protein separation and purification. For example, the antibodies can be separated and purified by appropriately selecting and combining column chromatography such as affinity chromatography, filtration, ultrafiltration, salting-out, dialysis, SDS-polyacrylamide gel electrophoresis, isoelectric focusing, and such, without limitation (Antibodies: A Laboratory Manual. Ed Harlow and David Lane, Cold Spring Harbor Laboratory, 1988). Columns used for affinity chromatography include, for example, protein A columns and protein G columns.

As described above, a neutralizing antibody of the present invention can be used in a method for measuring the reactivity of F.VIII in the presence of a substance having a F.VIII function-substituting activity, such as a method for measuring F.VIII activity and F.VIII inhibitor titer. The method for measuring F.VIII activity of the present invention comprises the step of bringing the following (1) into contact with the following (2). Otherwise, the method can be carried out according to conventionally used methods for measuring F.VIII activity.

(1) A blood-derived sample comprising a substance having an activity of functionally substituting for F.VIII.

(2) A substance that neutralizes the substance having an activity of functionally substituting for F.VIII.

An example of the substance that neutralizes the substance having an activity of functionally substituting for F.VIII in the present invention is preferably an antibody that neutralizes the substance having an activity of functionally substituting for F.VIII, or more preferably neutralizing antibodies IDA0288, IDA0339, or such described in the present specification. In the method for measuring F.VIII activity of the present invention, the substance may be used alone, or in combination of two or more types. Furthermore, in the present invention, the above-mentioned substance that neutralizes the substance having an activity of functionally substituting for F.VIII may be in the form of a composition. The composition may contain buffers, substances ordinarily used to measure the reactivity of F.VIII, and such.

Methods for Measuring F.VIII Activity

As the generally used F.VIII activity measurement methods, such methods known to those skilled in the art can be used, and for example, one can use a one-stage clotting assay (Casillas et al., (1971) Coagulation 4: 107-11) that uses factor VIII-deficient plasma (Sysmex, Kobe, Japan), which is based on coagulation time (aPTT measurements). One-stage clotting assay is carried out, for example, by the following method. Three solutions, 50 μL of 10-fold diluted test plasma, 50 μL of F.VIII-deficient plasma, and 50 μL of an APTT reagent, are mixed; this is incubated at 37° C. for 5 minutes; and then upon initiating the coagulation reaction by adding 50 μL of a calcium solution, the time to coagulation is measured. Furthermore, instead of the test plasma, serially diluted samples of normal plasma (F.VIII activity in a ten-fold diluted normal plasma is specified as 100%) are measured, and a calibration curve is produced by plotting the F.VIII activity on the horizontal axis and coagulation time on the vertical axis. The coagulation time of the test plasma is converted to F.VIII activity using the calibration curve, and F.VIII activity in the test plasma is calculated. Herein, unless stated otherwise, the phrase "measurement of F.VIII activity" is used as a phrase that may include "measurement of activated coagulation factor VIII (F.VIIIa) activity".

In addition to one-stage clotting assay, thrombin generation assay (TGA), measurement methods that use rotational thromboelastometry, F.VIII chromogenic assay, coagulation waveform analysis, thrombin and activated factor X production assay, and such may be used as the method for measuring F.VIII activity. The method for measuring F.VIII inhibitor titer of the present invention includes the step of bringing the following (1) into contact with the following (2). Otherwise, the method can be carried out according to generally used methods for measuring F.VIII inhibitor titer.

(1) A blood-derived sample containing a substance having an activity of functionally substituting for F.VIII.

(2) A substance that neutralizes the substance having an activity of functionally substituting for F.VIII.

In the present invention, neutralizing antibodies of the present invention can be used at concentrations at which the substance having an activity of functionally substituting for F.VIII can be neutralized. Such concentrations can be appropriately adjusted by those skilled in the art. Specific examples include, but are not limited to, 1 to 100 μg/mL, preferably 5 to 80 μg/mL, more preferably 10 to 60 μg/mL, and particularly preferably 20 to 40 μg/mL.

Methods for Measuring F.VIII Inhibitor Titer

As the generally used F.VIII inhibitor titer measurement methods, such methods known to those skilled in the art can be used, and for example, one can use Bethesda assay (Kasper et al., (1975) Thrombos Diath Haemorrh 34: 869-872), ELISA method, and Nijmegen Bethesda assay (Nijmegen modification assay) (Verbruggen et al., (1995) Thromb Haemost 73: 247-251). Bethesda assay is carried out, for example, by the following method. A solution produced by mixing equal amounts of normal plasma and test plasma is incubated at 37° C. for two hours, and then the residual factor VIII activity in normal plasma is measured by one-stage clotting assay based on activated partial thromboplastin time (APTT). The action of inhibiting 50% of the factor VIII activity in normal plasma is specified as 1 Bethesda (1 BU), and therefore the F.VIII inhibitor titer is calculated in units of Bethesda. When the F.VIII inhibitor titer in the test plasma is high and the residual F.VIII activity does not lie within the range of 25% to 75%, test plasma suitably diluted with a buffer is used to recalculate the Bethesda units, and subsequently, the value is multiplied by the dilution ratio to calculate the F.VIII inhibitor titer in the test plasma.

F.VIII Inhibitors

The F.VIII inhibitor is an isoantibody against foreign F.VIII and emerges in 20% to 30% of hemophilia A patients. An individual who had been normal may later form autoantibodies against F.VIII. Generally, most F.VIII inhibitor isoantibodies and autoantibodies function as anti-F.VIII neutralizing antibodies, and decrease or eliminate F.VIII activity.

Methods for Obtaining Samples

In the present invention, blood-derived samples are preferably blood-derived samples collected from a test subject. Such blood-derived samples can be obtained from test subjects that received a substance having a F.VIII-substituting activity. A test subject includes, for example, a patient with hemorrhagic symptoms at any part in the body (hemorrhagic disease patient). The main bleeding sites are intraarticular, intramuscular, subcutaneous, intraoral, intracranial, digestive tract, intranasal, and such, but are not limited thereto. The hemorrhagic disease patient is preferably a patient with hemorrhagic disease caused by decrease or deficiency in a F.VIII activity and/or F.VIIIa activity. The patient with hemorrhagic disease caused by decrease or deficiency in the F.VIII activity and/or F.VIIIa activity is a patient with hemorrhagic symptoms, and examples include patients with a priori or posteriori decrease or deficiency in either or both of the F.VIII activity and F.VIIIa activity. Decrease in the activities of F.VIII and F.VIIIa means that in comparison to those of healthy individuals, these activities are preferably less than 40% (for example, less than 40%, less than 30%, less than 20%, or less than 10%), more preferably less than 10% (for example, less than 10%, less than 9%, less than 8%, less than 7%, or less than 6%), even more preferably less than 5% (for example, less than 5%, less than 4%, less than 3%, or less than 2%), and particularly preferably less than 1% in a patient, without being limited thereto.

More specifically, examples of such diseases include diseases selected from among hemophilia (hemophilia A and hemophilia B), acquired hemophilia, and von Willebrand's disease caused by functional abnormality or deficiency of von Willebrand factor (vWF), but are not limited thereto. Blood-derived samples include serum, plasma, or whole blood. In the present invention, use of plasma samples is preferred. Methods for obtaining blood-derived samples from test subjects are well known to those skilled in the art.

Compositions and Kits

A neutralizing antibody of the present invention may compose a composition comprising a buffer required for the method for measuring the reactivity of F.VIII, a substance ordinarily used for measuring the reactivity of F.VIII, and such. Furthermore, a neutralizing antibody of the present invention may be packaged in advance with various types of reagents such as buffers required for the method for measuring the reactivity of F.VIII and substances ordinarily used for measuring the reactivity of F.VIII, and provided as a kit. Examples of a neutralizing antibody that composes a composition or a kit of the present invention are preferably neutralizing antibodies IDA0288, IDA0339, and such described herein. A composition or a kit of the present invention can include either one or preferably both of these neutralizing antibodies. In addition to the buffer, compositions and kits of the present invention may include as the substance ordinarily used for measuring the reactivity of F.VIII, plasma samples isolated from a human whose F.VIII activity and F.IX activity in the blood are normal, a substance having a F.VIII-substituting activity, and anything that can be used in F.VIII activity measurement, or anything that can be used in F.VIII inhibitor titer measurement. Furthermore, the various types of reagents included in the kits can be in the form of a powder or liquid according to their mode of use. Furthermore, they can be stored in appropriate containers and used when suitable.

By using the method that utilizes an antibody of the present invention, for example, the disease severity of a patient who received the substance having an activity of functionally substituting for F.VIII can be diagnosed. Reactivity of F.VIII can be measured using the method that utilizes an antibody of the present invention, and the severity of the patient and/or inhibitor titer can be diagnosed/assessed based on the measurement results. The diagnosis and assessment methods can be performed by methods known to those skilled in the art. Those skilled in the art can decide the therapeutic strategy for the patient based on the diagnosis and assessment. The present invention may comprise the step of determining the dose of the substance having an activity of functionally substituting for F.VIII according to the decided therapeutic strategy, and the step of administering the substance having an activity of functionally substituting for F.VIII.

By using the method that utilizes an antibody of the present invention, for example, the pharmacological activity of a substance having an activity of functionally substituting for F.VIII and/or a F.VIII formulation in patients who received the substance having an activity of functionally substituting for F.VIII and/or the F.VIII formulation can be monitored. Monitoring can be carried out by methods known to those skilled in the art.

The kit that comprises an antibody of the present invention can be used, for example, as a kit for diagnosing the severity of a patient who received a substance having an activity of functionally substituting for F.VIII. Reactivity of F.VIII can be measured using the kit comprising an antibody of the present invention, and the patient's severity and/or inhibitor titer can be diagnosed/assessed based on the measurement results. The diagnosis and assessment methods can be performed by methods known to those skilled in the art.

The kit comprising an antibody of the present invention can be used, for example, as a kit for monitoring the pharmacological activity of a F.VIII formulation in a patient who received a substance having an activity of functionally substituting for F.VIII and the F.VIII formulation. Monitoring can be carried out by methods known to those skilled in the art.

The patients that are the subjects of the methods that use an antibody of the present invention or kits comprising an antibody of the present invention are, for example, hemophilia A patients, acquired hemophilia A patients, von Willebrand disease patients, and hemophilia A patients with emergence of an inhibitor against F.VIII and/or F.VIIIa.

When used herein, embodiments represented by the expression "comprising . . . " include embodiments represented by the expression "essentially consisting of . . ." and embodiments represented by the expression "consisting of . . . ".

The entire contents of all patents and reference documents explicitly cited herein are incorporated herein by reference.

The present invention will be further illustrated by the Examples below, but it is not to be construed as being limited thereto.

EXAMPLES

[Example 1] Production of Antibodies Against Emicizumab and Anti-F.IXa/F.X Bispecific Antibody, Sequencing of Variable Regions, and Production of Expression Vectors QT15 F(ab')2 or JT13 F(ab')2 was produced by a method known to those skilled in the art, and three New Zealand white rabbits (Kitayama Labes Co., Ltd.) were immunized four times. The details of the anti-F.IX antibody QT15, and the anti-F.X antibody JT13, are shown in Table 1.

TABLE 1

| Antibody | VHA | CHA | VLA | CLA |
|---|---|---|---|---|
| QT15 | QH06 | QC2 | QL32 | CL2 |
| | (SEQ ID NO: 39) | (SEQ ID NO: 40) | (SEQ ID NO: 41) | (SEQ ID NO: 42) |
| JT13 | JH07 | JC2 | JL07 | CL4 |
| | (SEQ ID NO: 43) | (SEQ ID NO: 44) | (SEQ ID NO: 45) | (SEQ ID NO: 46) |

One week after the final immunization, peripheral blood mononuclear cells and splenocytes were recovered. Cells that bind to the QT15 Whole antibody or the JT13 Whole antibody were concentrated by MACS. Next, the cells were selected by a cell sorter (FACS aria III, BD) using PE labeled anti-rabbit IgG antibody (Southern biotech) with the QT15 Whole antibody or the JT13 Whole antibody. Using the antibodies secreted in the culture supernatant of those B cells, B cells that secrete antibodies which bind to the variable region of only one of either the QT15 Whole antibody or the JT13 Whole antibody and to the variable region of Emicizumab, but which do not bind to the constant region, were selected. The sequences of the variable regions obtained by RT-PCR from the selected B cells were inserted into expression vectors containing the known rabbit IgG constant region sequences (heavy chain: IgG/SEQ ID NO: 123; light chain: Igκ/SEQ ID NO: 124). Using the obtained plasmids, 1) an antibody (named IDA0288) that binds to the variable regions of QT15 Whole and Emicizumab but does not bind to the constant region and JT13 Whole and 2) an antibody (named IDA0339) that binds to the variable regions of JT13 Whole and Emicizumab but does not bind to the constant region and QT15 Whole were prepared by methods known to those skilled in the art. The nucleotide sequences of the regions encoding IDA0288 and IDA0339 were identified by DNA sequencing.

Heavy Chain Variable Region of IDA0288;
Amino acid sequence: SEQ ID NO: 1
Nucleic acid sequence: SEQ ID NO: 5
CDR1 amino acid sequence: SEQ ID NO: 12
CDR2 amino acid sequence: SEQ ID NO: 13
CDR3 amino acid sequence: SEQ ID NO: 14
CDR1 nucleic acid sequence: SEQ ID NO: 15
CDR2 nucleic acid sequence: SEQ ID NO: 16
CDR3 nucleic acid sequence: SEQ ID NO: 17

Light Chain Variable Region of IDA0288;
Amino acid sequence: SEQ ID NO: 2
Nucleic acid sequence: SEQ ID NO: 6
CDR1 amino acid sequence: SEQ ID NO: 18
CDR2 amino acid sequence: SEQ ID NO: 19
CDR3 amino acid sequence: SEQ ID NO: 20
CDR1 nucleic acid sequence: SEQ ID NO: 21
CDR2 nucleic acid sequence: SEQ ID NO: 22
CDR3 nucleic acid sequence: SEQ ID NO: 23
Heavy Chain Variable Region of IDA0339;
Amino acid sequence: SEQ ID NO: 3
Nucleic acid sequence: SEQ ID NO: 7
CDR1 amino acid sequence: SEQ ID NO: 24
CDR2 amino acid sequence: SEQ ID NO: 25
CDR3 amino acid sequence: SEQ ID NO: 26
CDR1 nucleic acid sequence: SEQ ID NO: 27
CDR2 nucleic acid sequence: SEQ ID NO: 28
CDR3 nucleic acid sequence: SEQ ID NO: 29
Light Chain Variable Region of IDA0339;
Amino acid sequence: SEQ ID NO: 4

Nucleic acid sequence: SEQ ID NO: 8
CDR1 amino acid sequence: SEQ ID NO: 30
CDR2 amino acid sequence: SEQ ID NO: 31
CDR3 amino acid sequence: SEQ ID NO: 32
CDR1 nucleic acid sequence: SEQ ID NO: 33
CDR2 nucleic acid sequence: SEQ ID NO: 34
CDR3 nucleic acid sequence: SEQ ID NO: 35

[Example 2] One-Stage Clotting Assay Carried Out Under Neutralization of Anti-F.IXa/F.X Bispecific Antibody Using IDA0288 and IDA0339 or rAQ8 and rAJ540

The expression clone plasmids produced and obtained in Example 1 were introduced into Expi293 cells, large-scale culturing and purification with ProA were performed, and IDA0288 and IDA0339 antibodies were produced.

IDA0288, IDA0339, rAQ8 (heavy chain variable region: SEQ ID NO: 79; light chain variable region: SEQ ID NO: 80) and rAJ540 (heavy chain variable region: SEQ ID NO: 81; light chain variable region: SEQ ID NO: 82) described in the Examples of WO2016/047656 were individually diluted with TBS to 300 µg/mL, and then equal amounts of IDA0288 and IDA0339 or rAQ8 and rAJ540 were mixed to produce an anti-antibody solution.

Anti-F.IXa/F.X bispecific antibodies (Emicizumab, #1 to #6) were prepared by a routine method. The amino acid sequences of these antibodies are summarized in Table 2-1 and Table 2-2. Each of the anti-F.IXa/F.X bispecific antibodies (Emicizumab, #1 to #6) was diluted stepwise with F.VIII-deficient plasma (Siemens) to 12.5 µg/mL to produce antibody solutions. According to the combinations shown in Table 3, 120 µL of the anti-antibody solution and 30 µL of the antibody solution were mixed to produce measurement sample solutions, and they were left to stand at room temperature for 5 minutes.

50 µL of a measurement sample solution and 50 µL of Thrombocheck APTT-SLA (Sysmex) were mixed and incubated at 37° C. for 190 seconds. After incubation, 50 µL of 0.02 M calcium chloride solution (Sysmex) was added to initiate coagulation, and the coagulation time was measured using CS-2000i (Sysmex). The details of the combinations of the anti-F.IXa/F.X bispecific antibodies and the measurement samples are shown below in Table 3.

TABLE 2-1

| Antibody | Anti-F.IX chain | | | |
| | VHA | CHA | VLA | CLA |
| --- | --- | --- | --- | --- |
| Emicizumab | Q499 (SEQ ID NO: 47) | z121 (SEQ ID NO: 48) | L404 (SEQ ID NO: 49) | K (SEQ ID NO: 50) |
| #1 | Q499 (SEQ ID NO: 47) | QC1 (SEQ ID NO: 51) | QNK131s (SEQ ID NO: 52) | CL1 (SEQ ID NO: 53) |
| #2 | Q499 (SEQ ID NO: 47) | QC1 (SEQ ID NO: 51) | QL20 (SEQ ID NO: 54) | CL1 (SEQ ID NO: 53) |
| #3 | QH04 (SEQ ID NO: 55) | QC3 (SEQ ID NO: 56) | QL26 (SEQ ID NO: 57) | CL2 (SEQ ID NO: 58) |
| #4 | QH06 (SEQ ID NO: 59) | QC3 (SEQ ID NO: 56) | QL30 (SEQ ID NO: 60) | CL2 (SEQ ID NO: 58) |
| #5 | QH04 (SEQ ID NO: 55) | QC3 (SEQ ID NO: 56) | QL31 (SEQ ID NO: 62) | CL2 (SEQ ID NO: 58) |
| #6 | QH06 (SEQ ID NO: 59) | QC3 (SEQ ID NO: 56) | QL32 (SEQ ID NO: 61) | CL2 (SEQ ID NO: 58) |

TABLE 2-2

| Antibody | Anti-F.X chain | | | |
| | VHA | CHA | VLA | CLA |
| --- | --- | --- | --- | --- |
| Emicizumab | J327 (SEQ ID NO: 63) | z119 (SEQ ID NO: 64) | L404 (SEQ ID NO: 65) | K (SEQ ID NO: 66) |
| #1 | J327 (SEQ ID NO: 63) | JC1 (SEQ ID NO: 67) | JNL095 (SEQ ID NO: 68) | CL3 (SEQ ID NO: 69) |
| #2 | J327 (SEQ ID NO: 63) | JC1 (SEQ ID NO: 67) | JL01 (SEQ ID NO: 70) | CL3 (SEQ ID NO: 69) |
| #3 | JH05 (SEQ ID NO: 71) | JC3 (SEQ ID NO: 72) | JL05 (SEQ ID NO: 73) | CL4 (SEQ ID NO: 74) |
| #4 | JH07 (SEQ ID NO: 75) | JC3 (SEQ ID NO: 72) | JL07 (SEQ ID NO: 76) | CL4 (SEQ ID NO: 74) |
| #5 | JH08 (SEQ ID NO: 77) | JC3 (SEQ ID NO: 72) | JL08 (SEQ ID NO: 78) | CL4 (SEQ ID NO: 74) |
| #6 | JH07 (SEQ ID NO: 75) | JC3 (SEQ ID NO: 72) | JL07 (SEQ ID NO: 76) | CL4 (SEQ ID NO: 74) |

TABLE 2-3

| Antibody | Buffer |
| --- | --- |
| Emicizumab | 20 mM Histidine, 160 mM Aspartic acid, 150 mM Arginine, 0.5 mg/mL poloxamer 188, pH 6.0 |
| #1 | Tris-Buffered-Saline |
| #2 | Tris-Buffered-Saline |
| #3 | 20 mM Histidine, 150 mM Arginine-aspartic acid, 0.5 mg/mL Poloxamer 188, pH 6.0 |
| #4 | 20 mM Histidine, 150 mM Arginine-aspartic acid, pH 6.0 |
| #5 | 20 mM Histidine, 150 mM Arginine-aspartic acid, pH 6.0 |
| #6 | 20 mM Histidine-aspartate buffer, 150 mM Arginine, 0.5 mg/mL poloxamer 188, pH 6.0 |

TABLE 3

| | Antibody | Antibody concentration | Anti-antibody | Anti-antibody concentration |
| --- | --- | --- | --- | --- |
| sample01 | Emicizumab | 10 µg/mL | — | — |
| sample02 | #1 | | — | — |
| sample03 | #2 | | — | — |
| sample04 | #3 | | — | — |

TABLE 3-continued

| | Antibody | Antibody concentration | Anti-antibody | Anti-antibody concentration |
|---|---|---|---|---|
| sample05 | #4 | | — | — |
| sample06 | #5 | | — | — |
| sample07 | #6 | | — | — |
| sample08 | — | — | — | — |
| sample09 | Emicizumab | 10 µg/mL | IDA0288/IDA0339 | 30 µg/mL |
| sample10 | #1 | | | |
| sample11 | #2 | | | |
| sample12 | #3 | | | |
| sample13 | #4 | | | |
| sample14 | #5 | | | |
| sample15 | #6 | | | |
| sample16 | — | — | | |
| sample17 | Emicizumab | 10 µg/mL | rAQ8/rAJ540 | 30 µg/mL |
| Sample18 | #1 | | | |
| Sample19 | #2 | | | |
| sample20 | #3 | | | |
| sample21 | #4 | | | |
| sample22 | #5 | | | |
| sample23 | #6 | | | |
| sample24 | — | — | | |

Results

Measurements were taken twice, and the results of calculating the average of the coagulation times are shown in FIG. 1. In the groups without addition of the anti-antibody solution, the coagulation times were shortened by the respective anti-F.IXa/F.X bispecific antibodies. In the groups with addition of the anti-antibody IDA0288/IDA0339, the coagulation times were partly shortened by #1 and #2, but the coagulation times when adding Emicizumab and other anti-F.IXa/F.X bispecific antibodies were the same as in the group without anti-F.IXa/F.X bispecific antibody addition, and the activities of Emicizumab and the anti-F.IXa/F.X bispecific antibodies other than #1 and #2 were shown to be completely neutralized. On the other hand, in the group with addition of the anti-antibody rAQ8/rAJ540, while coagulation time due to Emicizumab addition was similar to the group without anti-F.IXa/F.X bispecific antibody addition, coagulation times were partly shortened by addition of other anti-F.IXa/F.X bispecific antibodies, and the activities of these other anti-F.IXa/F.X bispecific antibodies were not completely neutralized.

INDUSTRIAL APPLICABILITY

The present invention provides antibodies for use in methods for measuring the reactivity of F.VIII in the presence of a bispecific antibody having a F.VIII function-substituting activity, for example, methods for measuring F.VIII activity or F.VIII inhibitor titer. The methods that use the antibodies of the present invention enable accurate measurement of the reactivity of F.VIII in patients during treatment of hemorrhagic diseases, such as hemophilia, by using the bispecific antibody.

The invention claimed is:

1. An antibody that comprises a heavy chain variable region comprising the amino acid sequence of SEQ ID NO: 1 and a light chain variable region comprising the amino acid sequence of SEQ ID NO: 2.

2. An antibody that comprises an antibody heavy chain comprising the amino acid sequence of SEQ ID NO: 131 and an antibody light chain comprising the amino acid sequence of SEQ ID NO: 132.

3. An antibody that comprises a heavy chain variable region comprising the amino acid sequence of SEQ ID NO: 3 and a light chain variable region comprising the amino acid sequence of SEQ ID NO: 4.

4. An antibody that comprises an antibody heavy chain comprising the amino acid sequence of SEQ ID NO: 135 and an antibody light chain comprising the amino acid sequence of SEQ ID NO: 136.

5. A composition comprising the antibody of claim 1.

6. A composition comprising the antibody of claim 2.

7. A composition comprising the antibody of claim 3.

8. A composition comprising the antibody of claim 4.

9. A kit for measuring the reactivity of coagulation factor VIII, wherein the kit comprises the composition of claim 5, 6, 7, or 8.

10. An antibody comprising:

a heavy chain variable region that comprises a CDR1 consisting of the amino acid sequence of SEQ ID NO: 12, a CDR2 consisting of the amino acid sequence of SEQ ID NO: 13, and a CDR3 consisting of the amino acid sequence of SEQ ID NO: 14, and a light chain variable region that comprises a CDR1 consisting of the amino acid sequence of SEQ ID NO: 18, a CDR2 consisting of the amino acid sequence of SEQ ID NO: 19, and a CDR3 consisting of the amino acid sequence of SEQ ID NO: 20.

11. An antibody comprising:

a heavy chain variable region that comprises a CDR1 consisting of the amino acid sequence of SEQ ID NO: 24, a CDR2 consisting of the amino acid sequence of SEQ ID NO: 25, and a CDR3 consisting of the amino acid sequence of SEQ ID NO: 26, and a light chain variable region that comprises a CDR1 consisting of the amino acid sequence of SEQ ID NO: 30, a CDR2 consisting of the amino acid sequence of SEQ ID NO: 31, and a CDR3 consisting of the amino acid sequence of SEQ ID NO: 32.

12. A composition comprising the antibody of claim 10.

13. A composition comprising the antibody of claim 11.

14. A method for neutralizing a bispecific antibody, the method comprising:

providing a blood-derived sample obtained from a test subject who was administered the bispecific antibody, wherein the bispecific antibody comprises a first heavy chain comprising the amino acid sequence of SEQ ID NO: 9, a second heavy chain comprising the amino acid sequence of SEQ ID NO: 11, and two light chains, each comprising the amino acid sequence of SEQ ID NO: 10; and contacting the blood-derived sample with both:

(a) the antibody of claim 4, and (b) an antibody that comprises a heavy chain variable region comprising the amino acid sequence of SEQ ID NO: 3 and a light chain variable region comprising the amino acid sequence of SEQ ID NO: 4.

15. A method for neutralizing a bispecific antibody, the method comprising:

providing a blood-derived sample obtained from a test subject who was administered the bispecific antibody, wherein the bispecific antibody comprises a first heavy chain comprising the amino acid sequence of SEQ ID NO: 9, a second heavy chain comprising the amino acid sequence of SEQ ID NO: 11, and two light chains, each comprising the amino acid sequence of SEQ ID NO: 10; and contacting the blood-derived sample with both:

(a) the composition of claim 12, and (b) a composition comprising an antibody that comprises a heavy chain variable region comprising the amino acid sequence of SEQ ID NO: 3 and a light chain variable region comprising the amino acid sequence of SEQ ID NO: 4.

16. A method for neutralizing a bispecific antibody, the method comprising:

providing a blood-derived sample obtained from a test subject who was administered the bispecific antibody, wherein the bispecific antibody comprises a first heavy chain comprising the amino acid sequence of SEQ ID NO:9, a second heavy chain comprising the amino acid sequence of SEQ ID NO: 11, and two light chains, each comprising the amino acid sequence of SEQ ID NO: 10; and contacting the blood-derived sample with both:

(a) the antibody of claim 10, and (b) an antibody comprising a heavy chain variable region that comprises a CDR1 consisting of the amino acid sequence of SEQ ID NO: 24, a CDR2 consisting of the amino acid sequence of SEQ ID NO: 25, and a CDR3 consisting of the amino acid sequence of SEQ ID NO: 26; and a light chain variable region that comprises a CDR1 consisting of the amino acid sequence of SEQ ID NO: 30, a CDR2 consisting of the amino acid sequence of SEQ ID NO: 31, and a CDR3 consisting of the amino acid sequence of SEQ ID NO: 32.

\* \* \* \* \*

SEQUENCE LISTING

```
<160> NUMBER OF SEQ ID NOS: 182

<210> SEQ ID NO 1
<211> LENGTH: 118
<212> TYPE: PRT
<213> ORGANISM: Oryctolagus cuniculus

<400> SEQUENCE: 1

Arg Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
            20                  25                  30

Tyr Trp Val Cys Trp Val Arg Gln Ala Pro Gly Lys Gly Leu Glu Trp
            35                  40                  45

Ile Gly Cys Ile Asp Thr Gly Ser Gly Asn Thr Ala Tyr Ala Ser Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Tyr Val Val Ala His Phe Asn Leu Trp Gly Pro Gly Thr
            100                 105                 110
```

```
Leu Val Thr Val Ser Ser
        115

<210> SEQ ID NO 2
<211> LENGTH: 111
<212> TYPE: PRT
<213> ORGANISM: Oryctolagus cuniculus

<400> SEQUENCE: 2

Ala Asp Val Val Met Thr Gln Thr Pro Ala Ser Val Ser Glu Pro Val
1               5                   10                  15

Gly Gly Thr Val Thr Ile Lys Cys Gln Ala Ser Glu Asp Ile Glu Arg
            20                  25                  30

Tyr Leu Ala Trp Tyr Gln Gln Lys Pro Gly Gln Pro Pro Lys Leu Leu
        35                  40                  45

Ile Asp Asp Ala Ser Asp Leu Ala Ser Gly Val Pro Ser Arg Phe Lys
    50                  55                  60

Gly Ser Gly Ser Gly Thr Glu Tyr Thr Leu Thr Ile Ser Ala Leu Glu
65                  70                  75                  80

Cys Ala Asp Ala Ala Thr Tyr Tyr Cys Gln Ser Tyr Tyr Ala Ile Ser
                85                  90                  95

Thr Tyr Gly Val Ala Phe Gly Gly Gly Thr Glu Val Val Val Lys
            100                 105                 110

<210> SEQ ID NO 3
<211> LENGTH: 118
<212> TYPE: PRT
<213> ORGANISM: Oryctolagus cuniculus

<400> SEQUENCE: 3

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Ser Trp Val Arg Gln Ala Pro Gly Lys Gly Leu Glu Tyr Ile Gly
        35                  40                  45

Tyr Ile Thr Val Asn Gly Val Thr Tyr Tyr Ala Asn Trp Ala Lys Gly
    50                  55                  60

Arg Phe Thr Ile Ser Lys Thr Ser Thr Thr Val Asp Leu Lys Ile Ser
65                  70                  75                  80

Ser Pro Thr Thr Glu Asp Thr Ala Thr Tyr Phe Cys Ala Arg Asp Gln
                85                  90                  95

Tyr Ile Asn Asn Gly Gly Ala Glu Phe Asn Ile Trp Gly Pro Gly Thr
            100                 105                 110

Leu Val Thr Val Ser Ser
        115

<210> SEQ ID NO 4
<211> LENGTH: 110
<212> TYPE: PRT
<213> ORGANISM: Oryctolagus cuniculus

<400> SEQUENCE: 4

Ala Tyr Asp Met Thr Gln Thr Pro Ser Phe Val Glu Ala Ala Val Gly
1               5                   10                  15

Gly Thr Val Thr Ile Lys Cys Gln Ala Ser Glu Ser Ile Ser Ser Trp
            20                  25                  30
```

```
Leu Ser Trp Tyr Gln Gln Lys Pro Gly Gln Pro Pro Lys Leu Leu Ile
        35                  40                  45

Tyr Gln Ala Ser Thr Leu Ala Ser Gly Val Ser Ser Arg Phe Lys Gly
        50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Gln Gly Tyr Ser Tyr Gly Asp
                85                  90                  95

Val Asp Asn Ala Phe Gly Gly Gly Thr Glu Val Val Val Lys
                100                 105                 110
```

<210> SEQ ID NO 5
<211> LENGTH: 354
<212> TYPE: DNA
<213> ORGANISM: Oryctolagus cuniculus

<400> SEQUENCE: 5

```
cgggagcaac tggaggagtc cggggggagac ctggtcaagc ctgagggatc cctgacactc     60
acctgcacag cctctggatt ctccttcagt agcagctact gggtgtgctg ggtccgccag    120
gctccaggga aggggctgga gtggatcgga tgcattgata ctggtagtgg taacactgcc    180
tacgcgagct gggcgaaagg ccgattcacc atctccaaga cctcgtcgac cacggtgact    240
ctgcaaatga ccagtctgac agccgcggac acggccacct atttctgtgc gagaggttat    300
gttgttgctc actttaactt gtggggccca ggcaccctgg tcaccgtctc ctcc          354
```

<210> SEQ ID NO 6
<211> LENGTH: 333
<212> TYPE: DNA
<213> ORGANISM: Oryctolagus cuniculus

<400> SEQUENCE: 6

```
gccgatgttg tgatgaccca gactccagcc tccgtgtctg aacctgtggg aggcacagtc     60
accatcaagt gccaggccag tgaggacatt gaaaggtatt tagcctggta tcagcagaaa    120
ccagggcagc ctcccaagct cctgatcgat gatgcatccg atctggcatc tggggtccca    180
tcgcggttca aaggcagtgg atctgggaca gaatacactc tcaccatcag cgccctggag    240
tgtgccgatg ctgccactta ctactgtcaa agctatatg ctattagtac ttatggtgtt    300
gctttcggcg gagggaccga ggtggtggtc aaa                                 333
```

<210> SEQ ID NO 7
<211> LENGTH: 354
<212> TYPE: DNA
<213> ORGANISM: Oryctolagus cuniculus

<400> SEQUENCE: 7

```
cagtcggtgg aggagtccgg gggtcgcctg gtcacgcctg ggacacccct gacactcacc     60
tgcacagtct ctggattctc cctcagcagc tacgacatga ctgggtccg ccaggctcca    120 ggaaaggggc tggagtacat cggatacatt actgttaatg gtgtcacata ctacgcgaac    180
tgggcgaaag gccgattcac catctccaaa acctcgacca cggtggatct gaaaatctcc    240
agtccgacaa ccgaggacac ggccacctat ttctgtgcca gagatcaata tattaataat    300
ggtggtgctg aatttaacat ctggggccca ggcaccctgg tcaccgtctc ctcc          354
```

<210> SEQ ID NO 8
<211> LENGTH: 330
<212> TYPE: DNA

<213> ORGANISM: Oryctolagus cuniculus

<400> SEQUENCE: 8

```
gcctatgata tgacccagac tccatccttc gtggaggcag ctgtgggagg cacagtcacc      60
atcaagtgcc aggccagtga gagcattagc agttggttat cctggtatca gcagaaacca     120
gggcagcctc ccaagctcct gatctaccag gcatccactt ggcatctggg ggtctcatcg     180
cggttcaaag gcagtggatc tgggacacag ttcactctca ccatcagcga cctggagtgt     240
gccgatgctg ccacttacta ttgtcaacag ggttatagtt atggtgatgt tgataatgct     300
ttcggcggag ggaccgaggt ggtggtcaaa                                       330
```

<210> SEQ ID NO 9
<211> LENGTH: 448
<212> TYPE: PRT
<213> ORGANISM: Artificial Sequence
<220> FEATURE:
<223> OTHER INFORMATION: An artificially synthesized sequence

<400> SEQUENCE: 9

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
    275                 280                 285
```

```
Asn Ala Lys Thr Lys Pro Arg Glu Glu Gln Tyr Asn Ser Thr Tyr Arg
    290             295             300
Val Val Ser Val Leu Thr Val Leu His Gln Asp Trp Leu Asn Gly Lys
305             310             315             320
Glu Tyr Lys Cys Lys Val Ser Asn Lys Gly Leu Pro Ser Ser Ile Glu
            325             330             335
Lys Thr Ile Ser Lys Ala Lys Gly Gln Pro Arg Glu Pro Gln Val Tyr
            340             345             350
Thr Leu Pro Pro Ser Gln Lys Glu Met Thr Lys Asn Gln Val Ser Leu
            355             360             365
Thr Cys Leu Val Lys Gly Phe Tyr Pro Ser Asp Ile Ala Val Glu Trp
            370             375             380
Glu Ser Asn Gly Gln Pro Glu Asn Asn Tyr Lys Thr Thr Pro Pro Val
385             390             395             400
Leu Asp Ser Asp Gly Ser Phe Phe Leu Tyr Ser Lys Leu Thr Val Asp
            405             410             415
Lys Ser Arg Trp Gln Glu Gly Asn Val Phe Ser Cys Ser Val Met His
            420             425             430
Glu Ala Leu His Asn Arg Tyr Thr Gln Lys Ser Leu Ser Leu Ser Pro
            435             440             445
```

<210> SEQ ID NO 10
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 10

```
Asp Ile Gln Met Thr Gln Ser Pro Ser Ser Leu Ser Ala Ser Val Gly
1               5               10              15
Asp Arg Val Thr Ile Thr Cys Lys Ala Ser Arg Asn Ile Glu Arg Gln
            20              25              30
Leu Ala Trp Tyr Gln Gln Lys Pro Gly Gln Ala Pro Glu Leu Leu Ile
            35              40              45
Tyr Gln Ala Ser Arg Lys Glu Ser Gly Val Pro Asp Arg Phe Ser Gly
    50              55              60
Ser Arg Tyr Gly Thr Asp Phe Thr Leu Thr Ile Ser Ser Leu Gln Pro
65              70              75              80
Glu Asp Ile Ala Thr Tyr Tyr Cys Gln Gln Tyr Ser Asp Pro Pro Leu
            85              90              95
Thr Phe Gly Gly Gly Thr Lys Val Glu Ile Lys Arg Thr Val Ala Ala
            100             105             110
Pro Ser Val Phe Ile Phe Pro Pro Ser Asp Glu Gln Leu Lys Ser Gly
            115             120             125
Thr Ala Ser Val Val Cys Leu Leu Asn Asn Phe Tyr Pro Arg Glu Ala
    130             135             140
Lys Val Gln Trp Lys Val Asp Asn Ala Leu Gln Ser Gly Asn Ser Gln
145             150             155             160
Glu Ser Val Thr Glu Gln Asp Ser Lys Asp Ser Thr Tyr Ser Leu Ser
            165             170             175
Ser Thr Leu Thr Leu Ser Lys Ala Asp Tyr Glu Lys His Lys Val Tyr
            180             185             190
Ala Cys Glu Val Thr His Gln Gly Leu Ser Ser Pro Val Thr Lys Ser
            195             200             205
```

```
Phe Asn Arg Gly Glu Cys
    210

<210> SEQ ID NO 11
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 11

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350
```

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
        435                 440

<210> SEQ ID NO 12
<211> LENGTH: 6
<212> TYPE: PRT
<213> ORGANISM: Oryctolagus cuniculus

<400> SEQUENCE: 12

Ser Ser Tyr Trp Val Cys
1               5

<210> SEQ ID NO 13
<211> LENGTH: 17
<212> TYPE: PRT
<213> ORGANISM: Oryctolagus cuniculus

<400> SEQUENCE: 13

Cys Ile Asp Thr Gly Ser Gly Asn Thr Ala Tyr Ala Ser Trp Ala Lys
1               5                   10                  15

Gly

<210> SEQ ID NO 14
<211> LENGTH: 9
<212> TYPE: PRT
<213> ORGANISM: Oryctolagus cuniculus

<400> SEQUENCE: 14

Gly Tyr Val Val Ala His Phe Asn Leu
1               5

<210> SEQ ID NO 15
<211> LENGTH: 18
<212> TYPE: DNA
<213> ORGANISM: Oryctolagus cuniculus

<400> SEQUENCE: 15
agcagctact gggtgtgc                                              18

<210> SEQ ID NO 16
<211> LENGTH: 51
<212> TYPE: DNA
<213> ORGANISM: Oryctolagus cuniculus

<400> SEQUENCE: 16
tgcattgata ctggtagtgg taacactgcc tacgcgagct gggcgaaagg c         51

<210> SEQ ID NO 17
<211> LENGTH: 27
<212> TYPE: DNA
<213> ORGANISM: Oryctolagus cuniculus -continued

<400> SEQUENCE: 17
ggttatgttg ttgctcactt taacttg                                             27

<210> SEQ ID NO 18
<211> LENGTH: 11
<212> TYPE: PRT
<213> ORGANISM: Oryctolagus cuniculus

<400> SEQUENCE: 18

Gln Ala Ser Glu Asp Ile Glu Arg Tyr Leu Ala
1               5                   10

<210> SEQ ID NO 19
<211> LENGTH: 7
<212> TYPE: PRT
<213> ORGANISM: Oryctolagus cuniculus

<400> SEQUENCE: 19

Asp Ala Ser Asp Leu Ala Ser
1               5

<210> SEQ ID NO 20
<211> LENGTH: 12
<212> TYPE: PRT
<213> ORGANISM: Oryctolagus cuniculus

<400> SEQUENCE: 20

Gln Ser Tyr Tyr Ala Ile Ser Thr Tyr Gly Val Ala
1               5                   10

<210> SEQ ID NO 21
<211> LENGTH: 33
<212> TYPE: DNA
<213> ORGANISM: Oryctolagus cuniculus

<400> SEQUENCE: 21
caggccagtg aggacattga aaggtattta gcc                                      33

<210> SEQ ID NO 22
<211> LENGTH: 21
<212> TYPE: DNA
<213> ORGANISM: Oryctolagus cuniculus

<400> SEQUENCE: 22
gatgcatccg atctggcatc t                                                   21

<210> SEQ ID NO 23
<211> LENGTH: 36
<212> TYPE: DNA
<213> ORGANISM: Oryctolagus cuniculus

<400> SEQUENCE: 23
caaagctatt atgctattag tacttatggt gttgct                                   36

<210> SEQ ID NO 24
<211> LENGTH: 5
<212> TYPE: PRT
<213> ORGANISM: Oryctolagus cuniculus

<400> SEQUENCE: 24

Ser Tyr Asp Met Ser
1               5

```
<210> SEQ ID NO 25
<211> LENGTH: 16
<212> TYPE: PRT
<213> ORGANISM: Oryctolagus cuniculus

<400> SEQUENCE: 25

Tyr Ile Thr Val Asn Gly Val Thr Tyr Tyr Ala Asn Trp Ala Lys Gly
1               5                   10                  15

<210> SEQ ID NO 26
<211> LENGTH: 13
<212> TYPE: PRT
<213> ORGANISM: Oryctolagus cuniculus

<400> SEQUENCE: 26

Asp Gln Tyr Ile Asn Asn Gly Gly Ala Glu Phe Asn Ile
1               5                   10

<210> SEQ ID NO 27
<211> LENGTH: 15
<212> TYPE: DNA
<213> ORGANISM: Oryctolagus cuniculus

<400> SEQUENCE: 27
agctacgaca tgagc                                              15

<210> SEQ ID NO 28
<211> LENGTH: 48
<212> TYPE: DNA
<213> ORGANISM: Oryctolagus cuniculus

<400> SEQUENCE: 28
tacattactg ttaatggtgt cacatactac gcgaactggg cgaaaggc          48

<210> SEQ ID NO 29
<211> LENGTH: 39
<212> TYPE: DNA
<213> ORGANISM: Oryctolagus cuniculus

<400> SEQUENCE: 29
gatcaatata ttaataatgg tggtgctgaa tttaacatc                    39

<210> SEQ ID NO 30
<211> LENGTH: 11
<212> TYPE: PRT
<213> ORGANISM: Oryctolagus cuniculus

<400> SEQUENCE: 30

Gln Ala Ser Glu Ser Ile Ser Ser Trp Leu Ser
1               5                   10

<210> SEQ ID NO 31
<211> LENGTH: 7
<212> TYPE: PRT
<213> ORGANISM: Oryctolagus cuniculus

<400> SEQUENCE: 31

Gln Ala Ser Thr Leu Ala Ser
1               5

<210> SEQ ID NO 32
<211> LENGTH: 12
<212> TYPE: PRT
<213> ORGANISM: Oryctolagus cuniculus
```

-continued

<400> SEQUENCE: 32

Gln Gln Gly Tyr Ser Tyr Gly Asp Val Asp Asn Ala
1               5                   10

<210> SEQ ID NO 33
<211> LENGTH: 33
<212> TYPE: DNA
<213> ORGANISM: Oryctolagus cuniculus

<400> SEQUENCE: 33
caggccagtg agagcattag cagttggtta tcc                                      33

<210> SEQ ID NO 34
<211> LENGTH: 21
<212> TYPE: DNA
<213> ORGANISM: Oryctolagus cuniculus

<400> SEQUENCE: 34
caggcatcca ctttggcatc t                                                   21

<210> SEQ ID NO 35
<211> LENGTH: 36
<212> TYPE: DNA
<213> ORGANISM: Oryctolagus cuniculus

<400> SEQUENCE: 35
caacagggtt atagttatgg tgatgttgat aatgct                                   36

<210> SEQ ID NO 36
<211> LENGTH: 448
<212> TYPE: PRT
<213> ORGANISM: Artificial Sequence
<220> FEATURE:
<223> OTHER INFORMATION: An artificially synthesized sequence

<400> SEQUENCE: 36

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Asn Trp Val Arg Gln Ala Pro Gly Lys Gly Leu Glu Trp Val
        35                  40                  45

Ala Ser Ile Ser Pro Ser Gly Gly Ser Thr Tyr Tyr Arg Arg Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Arg Ala Gly His Asn Tyr Gly Ala Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

```
Pro Ala Val Leu Gln Ser Ser Gly Leu Tyr Ser Leu Ser Ser Val Val
        180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
                340                 345                 350

Thr Leu Pro Pro Ser Gln Glu Glu Met Thr Lys Asn Gln Val Ser Leu
                355                 360                 365

Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
        435                 440                 445
```

```
<210> SEQ ID NO 37
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 37
```

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
        50                  55                  60

Gln Asp Arg Val Thr Met Thr Ile Asp Lys Ser Thr Gly Thr Ala Tyr
65              70                  75                  80

Met Glu Leu Ser Ser Leu Arg Ser Glu Asp Thr Ala Val Tyr Tyr Cys
                85                  90                  95
```

```
Ala Arg Arg Arg Ser Tyr Gly Tyr Tyr His Asp Glu Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
            435                 440
```

<210> SEQ ID NO 38
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 38

```
Asp Ile Gln Met Thr Gln Ser Pro Ser Ser Leu Ser Ala Ser Val Gly
1               5                   10                  15
```

-continued

```
Asp Arg Val Thr Ile Thr Cys Lys Ala Ser Arg Asn Ile Glu Arg Asn
        20                  25                  30

Leu Ala Trp Tyr Gln Gln Lys Pro Gly Gln Ala Pro Glu Leu Leu Ile
        35                  40                  45

Tyr Ser Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Tyr Ser Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 39
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 39

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
        20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser
            115                 120
```

```
<210> SEQ ID NO 40
<211> LENGTH: 325
<212> TYPE: PRT
<213> ORGANISM: Artificial Sequence
<220> FEATURE:
```

-continued

<223> OTHER INFORMATION: An artificially synthesized sequence

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Ala His Tyr Thr Arg Lys Glu
305                 310                 315                 320

Leu Ser Leu Ser Pro
                325

<210> SEQ ID NO 41
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 41

Glu Ile Val Leu Thr Gln Ser Pro Ala Thr Leu Ser Val Ser Pro Gly
1               5                   10                  15

-continued

```
Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
            100                 105
```

```
<210> SEQ ID NO 42
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 42
```

```
Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 43
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 43
```

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Val Ile Tyr Asn Glu Glu Phe
        50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
```

-continued

```
              100             105             110
Thr Leu Val Thr Val Ser Ser
        115

<210> SEQ ID NO 44
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Ala His Tyr Thr Arg Glu Glu
305                 310                 315                 320

Leu Ser Leu Ser Pro
                325
```

-continued

```
<210> SEQ ID NO 45
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 45

Ser Tyr Val Leu Thr Gln Pro Val Ser Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
            100                 105

<210> SEQ ID NO 46
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 46

Gly Gln Pro Lys Ala Ala Pro Ser Val Thr Leu Phe Pro Pro Ser Ser
1               5                   10                  15

Glu Glu Leu Gln Ala Asn Lys Ala Lys Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Lys Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 47
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 47

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
                20                  25                  30

Asp Ile Gln Trp Val Arg Gln Ala Pro Gly Lys Gly Leu Glu Trp Val
            35                  40                  45
```

```
Ser Ser Ile Ser Pro Ser Gly Gln Ser Thr Tyr Tyr Arg Arg Glu Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Arg Thr Gly Arg Glu Tyr Gly Gly Gly Trp Tyr Phe Asp Tyr
            100             105             110

Trp Gly Gln Gly Thr Leu Val Thr Val Ser Ser
            115             120

<210> SEQ ID NO 48
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 48

Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Thr Cys Asn Val Asp His Lys Pro Ser Asn Thr Lys Val Asp Lys
                85              90              95

Arg Val Glu Ser Lys Tyr Gly Pro Pro Cys Pro Pro Cys Pro Ala Pro
            100             105             110

Glu Phe Leu Gly Gly Pro Ser Val Phe Leu Phe Pro Pro Lys Pro Lys
            115             120             125

Asp Thr Leu Met Ile Ser Arg Thr Pro Glu Val Thr Cys Val Val Val
    130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Tyr
            165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
            195             200             205

Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Lys Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
            275             280             285
```

Lys Leu Thr Val Asp Lys Ser Arg Trp Gln Glu Gly Asn Val Phe Ser
    290                 295                 300

Cys Ser Val Met His Glu Ala Leu His Asn Arg Tyr Thr Gln Lys Ser
305                 310                 315                 320

Leu Ser Leu Ser Pro
                325

<210> SEQ ID NO 49
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 50

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 51
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Arg Arg Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 52
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 52

Glu Ile Val Leu Thr Gln Ser Pro Ala Thr Leu Ser Val Ser Pro Gly
1               5                   10                  15

-continued

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Arg Pro Leu Thr
                85                  90                  95

Phe Gly Gly Gly Thr Lys Val Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 53

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 54
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 54

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Ser Pro Leu Thr
                85                  90                  95

Phe Gly Gly Gly Thr Lys Val Glu Ile Lys
            100                 105

-continued

```
<210> SEQ ID NO 55
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 55

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Glu Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser
        115                 120

<210> SEQ ID NO 56
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 56

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
```

-continued

```
                180             185             190

Trp Leu Asn Gly Lys Glu Tyr Lys Cys Lys Val Ser Asn Lys Gly Leu
        195             200             205

Pro Ser Ser Ile Glu Lys Thr Ile Ser Lys Ala Lys Gly Gln Pro Arg
        210             215             220

Glu Pro Gln Val Tyr Thr Leu Pro Pro Ser Gln Lys Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Lys Leu Thr Val Asp Lys Ser Arg Trp Gln Glu Gly Asn Val Phe Ser
        290             295             300

Cys Ser Val Leu His Glu Ala Leu His Ala His Tyr Thr Arg Lys Glu
305             310             315             320

Leu Ser Leu Ser Pro
            325
```

```
<210> SEQ ID NO 57
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 57

Glu Ile Val Leu Thr Gln Ser Pro Ala Thr Leu Ser Val Ser Pro Gly
1               5               10              15

Glu Arg Ala Thr Leu Ser Cys Arg Ala Ser Arg Ser Val Arg Arg Glu
            20              25              30

Leu Ala Trp Tyr Gln Lys Lys Pro Gly Gln Ala Pro Glu Leu Leu Ile
        35              40              45

Tyr Gly Ala Ser Thr Arg Glu Thr Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Met Ala Val Tyr Tyr Cys Gln Gln Tyr Arg Asp Pro Pro Gly
                85              90              95

Thr Phe Gly Gly Gly Thr Lys Val Glu Ile Lys
            100             105
```

```
<210> SEQ ID NO 58
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 58

Arg Thr Val Ala Ala Pro Ser Val Phe Ile Phe Pro Pro Ser Asp Glu
1               5               10              15

Gln Leu Lys Ser Gly Thr Ala Glu Val Val Cys Leu Leu Asn Asn Phe
            20              25              30

Tyr Pro Arg Glu Ala Lys Val Gln Trp Lys Val Asp Asn Ala Leu Gln
        35              40              45
```

Ser Gly Asn Ser Gln Glu Ser Val Thr Glu Gln Asp Ser Lys Asp Ser
    50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 59
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 59

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser
            115                 120

<210> SEQ ID NO 60
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 60

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 61

```
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 61

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 62

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 63
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 63

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45
```

-continued

```
Gly Asp Ile Asn Thr Arg Ser Gly Gly Ser Ile Tyr Asn Glu Glu Phe
    50              55                  60

Gln Asp Arg Val Ile Met Thr Val Asp Lys Ser Thr Asp Thr Ala Tyr
65              70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
                100                 105                 110

Thr Leu Val Thr Val Ser Ser
        115

<210> SEQ ID NO 64
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 64

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285
```

-continued

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Pro
                325

<210> SEQ ID NO 65
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 65

Asp Ile Gln Met Thr Gln Ser Pro Ser Ser Leu Ser Ala Ser Val Gly
1                   5                   10                  15

Asp Arg Val Thr Ile Thr Cys Lys Ala Ser Arg Asn Ile Glu Arg Gln
                20                  25                  30

Leu Ala Trp Tyr Gln Gln Lys Pro Gly Gln Ala Pro Glu Leu Leu Ile
            35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 66
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 66

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 67
<211> LENGTH: 325
<212> TYPE: PRT
<213> ORGANISM: Artificial Sequence
<220> FEATURE:
<223> OTHER INFORMATION: An artificially synthesized sequence

```
<400> SEQUENCE: 67

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Arg Arg Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Glu Ser
305                 310                 315                 320

Leu Ser Leu Ser Pro
                325

<210> SEQ ID NO 68
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 68

Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
```

-continued

```
                20                    25                    30

His Trp Tyr His Gln Arg Pro Gly Gln Ala Pro Ile Leu Val Met Phe
            35                    40                    45

Arg Asp Ala Arg Arg Pro Ser Gly Ile Pro Glu Arg Leu Ser Gly Ser
    50                    55                    60

Asn Ser Gly Asn Thr Ala Ser Leu Thr Ile Ser Gly Ala Gln Ala Gly
65                    70                    75                    80

Asp Glu Gly Asp Tyr Tyr Cys Gln Val Trp Asp Ser Ser Ser Ala Val
                85                    90                    95

Val Phe Gly Gly Gly Thr Lys Val Thr Val Val
            100                   105
```

```
<210> SEQ ID NO 69
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 69
```

```
Gly Gln Pro Lys Ala Ala Pro Ser Val Thr Leu Phe Pro Pro Ser Ser
1                   5                    10                    15

Glu Glu Leu Gln Ala Asn Lys Ala Thr Leu Val Cys Leu Ile Ser Asp
                20                    25                    30

Phe Tyr Pro Gly Ala Val Thr Val Ala Trp Lys Ala Asp Ser Ser Pro
            35                    40                    45

Val Lys Ala Gly Val Glu Thr Thr Thr Pro Ser Lys Gln Ser Asn Asn
    50                    55                    60

Lys Tyr Ala Ala Ser Ser Tyr Leu Ser Leu Thr Pro Glu Gln Trp Lys
65                    70                    75                    80

Ser His Arg Ser Tyr Ser Cys Gln Val Thr His Glu Gly Ser Thr Val
                85                    90                    95

Glu Lys Thr Val Ala Pro Thr Glu Cys Ser
            100                   105
```

```
<210> SEQ ID NO 70
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 70
```

```
Ser Tyr Val Leu Thr Gln Pro Val Ser Val Ser Val Ala Arg Gly Gln
1                   5                    10                    15

Thr Ala Thr Ile Thr Cys Glu Gly Asn His Ile Gly Asp Lys His Val
                20                    25                    30

His Trp Tyr His Gln Arg Pro Gly Gln Ala Pro Ile Leu Val Met Phe
            35                    40                    45

Arg Asp Ala Arg Arg Pro Ser Gly Ile Pro Glu Arg Leu Ser Gly Ser
    50                    55                    60

Asn Ser Gly Asn Thr Ala Ser Leu Thr Ile Ser Gly Ala Gln Ala Gly
65                    70                    75                    80

Asp Glu Gly Asp Tyr Tyr Cys Gln Val Trp Asp Ser Ser Ser Tyr Thr
                85                    90                    95

Val Phe Gly Gly Gly Thr Lys Val Thr Val Val
            100                   105
```

<210> SEQ ID NO 71
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 71

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
                20                  25                  30

Asn Met Asp Trp Val Arg Lys Ala Pro Gly Gln Gly Leu Glu Trp Met
            35                  40                  45

Gly Asp Ile Asn Thr Arg Ser Gly Gly Val Ile Tyr Asn Glu Glu Phe
        50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
                100                 105                 110

Thr Leu Val Thr Val Ser Ser
            115

<210> SEQ ID NO 72
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Glu Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Glu Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
                180                 185                 190

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
        290                 295                 300

Cys Ser Val Leu His Glu Ala Leu His Ala His Tyr Thr Arg Glu Glu
305                 310                 315                 320

Leu Ser Leu Ser Pro
                325

<210> SEQ ID NO 73
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 73

Ser Tyr Val Leu Thr Gln Pro Val Ser Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Glu Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
            100                 105

<210> SEQ ID NO 74
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 74

Gly Gln Pro Lys Ala Ala Pro Ser Val Thr Leu Phe Pro Pro Ser Ser
1               5                   10                  15

Glu Glu Leu Gln Ala Asn Lys Ala Lys Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
```

-continued

```
          50              55              60

Lys Tyr Ala Ala Ser Ser Tyr Leu Lys Leu Thr Pro Glu Gln Trp Lys
65              70              75              80

Ser His Arg Ser Tyr Ser Cys Gln Val Thr His Glu Gly Ser Thr Val
                85              90              95

Glu Lys Thr Val Ala Pro Thr Glu Cys Ser
            100             105

<210> SEQ ID NO 75
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 75

Gln Val Gln Leu Val Gln Ser Gly Ser Glu Leu Lys Lys Pro Gly Ala
1               5               10              15

Ser Val Lys Val Ser Cys Lys Ala Ser Gly Tyr Thr Phe Thr Gln Asn
            20              25              30

Asn Met Asp Trp Val Arg Gln Ala Pro Gly Gln Gly Leu Glu Trp Met
        35              40              45

Gly Asp Ile Asn Thr Arg Ser Gly Gly Val Ile Tyr Asn Glu Glu Phe
    50              55              60

Gln Asp Arg Leu Ile Met Thr Val Asp Lys Ser Thr Asp Thr Ala Tyr
65              70              75              80

Met Glu Leu Ser Ser Leu Arg Ser Glu Asp Thr Ala Thr Tyr His Cys
                85              90              95

Ala Arg Arg Lys Ser Tyr Gly Tyr Tyr Leu Asp Val Trp Gly Glu Gly
            100             105             110

Thr Leu Val Thr Val Ser Ser
        115

<210> SEQ ID NO 76
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 76

Ser Tyr Val Leu Thr Gln Pro Val Ser Val Ser Val Ala Leu Gly Gln
1               5               10              15

Thr Ala Thr Ile Thr Cys Glu Gly Glu Gln Ile Gly Ser Lys Glu Val
            20              25              30

His Trp Tyr His Gln Arg Pro Gly Gln Ala Pro Ile Leu Val Met Phe
        35              40              45

Arg Asp Ala Arg Arg Pro Ser Gly Ile Pro Glu Arg Leu Ser Gly Ser
    50              55              60

Asn Ser Gly Asn Thr Ala Ser Leu Thr Ile Ser Gly Ala Glu Ala Gly
65              70              75              80

Asp Glu Gly Asp Tyr Tyr Cys Gln Val Trp Asp Ser Ser Ser Tyr Thr
                85              90              95

Val Phe Gly Gly Gly Thr Lys Val Thr Val Val
            100             105

<210> SEQ ID NO 77
<211> LENGTH: 119
```

```
<212> TYPE: PRT
<213> ORGANISM: Artificial Sequence
<220> FEATURE:
<223> OTHER INFORMATION: An artificially synthesized sequence

<400> SEQUENCE: 77

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
        50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 78
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 78

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Ile Tyr
        35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
            100                 105

<210> SEQ ID NO 79
<211> LENGTH: 124
<212> TYPE: PRT
<213> ORGANISM: Artificial Sequence
<220> FEATURE:
<223> OTHER INFORMATION: AQ8 VH

<400> SEQUENCE: 79

Glu Val Asn Leu Val Glu Ser Gly Gly Gly Leu Val Gln Pro Gly Gly
1               5                   10                  15

Ser Met Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
```

-continued

```
            35                      40                      45

Ala Leu Ile Arg Asn Lys Ala Asn Gly Tyr Thr Thr Glu Tyr Ser Ala
    50                      55                      60

Ser Val Lys Gly Arg Phe Thr Ile Ser Arg Asp Asn Ser Gln Ser Ile
65                      70                      75                      80

Leu Tyr Leu Gln Met Asn Ala Leu Arg Ala Glu Asp Ser Ala Thr Tyr
                85                      90                      95

Tyr Cys Ala Arg Asp Ser Tyr Tyr Ser Tyr Asp Gly Tyr Ala Met Asp
                100                     105                     110

Tyr Trp Gly Gln Gly Thr Ser Val Thr Val Ser Ser
        115                     120

<210> SEQ ID NO 80
<211> LENGTH: 107
<212> TYPE: PRT
<213> ORGANISM: Artificial Sequence
<220> FEATURE:
<223> OTHER INFORMATION: AQ8 VL

<400> SEQUENCE: 80

Asp Ile Gln Met Thr Gln Ser Pro Ala Ser Leu Ala Ala Ser Val Gly
1                   5                       10                      15

Glu Thr Ile Thr Ile Thr Cys Gln Ala Ser Glu Asn Ile Tyr Phe Ser
                20                      25                      30

Leu Ala Trp Tyr Gln Gln Lys Gln Gly Lys Ser Pro Gln Leu Leu Ile
        35                      40                      45

Tyr Asn Thr Asp Ser Leu Lys Asp Gly Val Pro Ser Arg Phe Ser Gly
    50                      55                      60

Ser Gly Ser Gly Thr Gln Tyr Ser Met Lys Ile Asn Ser Met Gln Pro
65                      70                      75                      80

Glu Asp Thr Ala Thr Tyr Phe Cys Arg Gln Ser Tyr Asp Phe Pro Trp
                85                      90                      95

Thr Phe Gly Gly Gly Thr Lys Leu Glu Ile Lys
                100                     105

<210> SEQ ID NO 81
<211> LENGTH: 120
<212> TYPE: PRT
<213> ORGANISM: Artificial Sequence
<220> FEATURE:
<223> OTHER INFORMATION: AJ540 VH

<400> SEQUENCE: 81

Gln Ile Gln Leu Val Gln Ser Gly Pro Glu Leu Lys Lys Pro Gly Glu
1                   5                       10                      15

Ser Val Lys Ile Ser Cys Lys Ala Ser Gly Tyr Thr Phe Thr Asp Tyr
                20                      25                      30

Ala Met His Trp Val Lys Gln Val Pro Gly Lys Gly Leu Lys Trp Met
        35                      40                      45

Gly Trp Ile Asn Thr Tyr Thr Gly Lys Pro Thr Tyr Ala Asp Asp Phe
        50                      55                      60

Lys Gly Arg Phe Val Phe Ser Leu Glu Ala Ser Ala Ser Thr Ala Asn
65                      70                      75                      80

Leu Gln Ile Ser Asn Leu Lys Asn Glu Asp Thr Ala Asn Val Phe Cys
                85                      90                      95

Ala Arg Glu Gly Gly Gly Tyr Tyr Trp Tyr Phe Asp Phe Trp Gly Pro
                100                     105                     110
```

Gly Thr Met Val Thr Val Ser Ser
     115            120

<210> SEQ ID NO 82
<211> LENGTH: 107
<212> TYPE: PRT
<213> ORGANISM: Artificial Sequence
<220> FEATURE:
<223> OTHER INFORMATION: AJ540 VL

<400> SEQUENCE: 82

Asp Ile Val Met Thr Gln Ser Pro Thr Ser Met Ser Ile Ser Val Gly
1             5             10            15

Asp Arg Val Thr Met Asn Cys Lys Ala Asn Gln Asn Val Asp Phe Asn
         20             25            30

Val Asp Trp Tyr Gln Gln Lys Thr Gly Gln Ser Pro Lys Leu Leu Ile
       35            40            45

Tyr Lys Ala Ser Asn Arg Tyr Thr Gly Val Pro Asp Arg Phe Thr Gly
   50           55           60

Ser Gly Ser Gly Thr Asp Phe Thr Phe Thr Ile Ser Asn Met Gln Ala
65             70           75           80

Glu Asp Leu Ala Val Tyr Tyr Cys Met Gln Ser Asn Ser Phe Pro Leu
         85           90           95

Thr Phe Gly Ser Gly Thr Asn Leu Glu Ile Lys
        100          105

<210> SEQ ID NO 83
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 83

Gln Val Gln Leu Val Glu Ser Gly Gly Gly Leu Val Gln Pro Gly Gly
1             5             10            15

Ser Leu Arg Leu Ser Cys Ala Ala Ser Gly Phe Thr Phe Ser Tyr Tyr
         20             25            30

Asp Ile Gln Trp Val Arg Gln Ala Pro Gly Lys Gly Leu Glu Trp Val
       35            40            45

Ser Ser Ile Ser Pro Ser Gly Gln Ser Thr Tyr Tyr Arg Arg Glu Val
   50           55           60

Lys Gly Arg Phe Thr Ile Ser Arg Asp Asn Ser Lys Asn Thr Leu Tyr
65             70           75           80

Leu Gln Met Asn Ser Leu Arg Ala Glu Asp Thr Ala Val Tyr Tyr Cys
         85           90           95

Ala Arg Arg Thr Gly Arg Glu Tyr Asp Gly Gly Trp Tyr Phe Asp Tyr
        100          105          110

Trp Gly Gln Gly Thr Leu Val Thr Val Ser Ser
        115          120

<210> SEQ ID NO 84
<211> LENGTH: 123
<212> TYPE: PRT
<213> ORGANISM: Artificial Sequence
<220> FEATURE:
<223> OTHER INFORMATION: An artificially synthesized sequence

<400> SEQUENCE: 84

Gln Val Gln Leu Val Glu Ser Gly Gly Gly Leu Val Gln Pro Gly Gly

```
1               5                   10                  15

Ser Leu Arg Leu Ser Cys Ala Ala Ser Gly Phe Thr Phe Ser Tyr Tyr
            20                  25                  30

Asp Ala Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Ser Glu Asp Gly Ala Gly Trp Tyr Phe Asp Tyr
            100                 105                 110

Trp Gly Gln Gly Thr Leu Val Thr Val Ser Ser
        115                 120
```

<210> SEQ ID NO 85
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 85

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Asp Gly Gly Trp His Phe Asp Tyr Trp
            100                 105                 110

Gly Gln Gly Thr Leu Val Thr Val Ser Ser
        115                 120
```

<210> SEQ ID NO 86
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 86

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Glu Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser
        115                 120

<210> SEQ ID NO 87
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 87

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser
        115                 120

<210> SEQ ID NO 88
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 88

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Arg Arg Asp
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Ser Pro Leu Thr
                85                  90                  95

Phe Gly Gly Gly Thr Lys Val Glu Ile Lys
            100                 105

<210> SEQ ID NO 89
```

```
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 89

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

Phe Gly Gly Gly Thr Lys Val Glu Ile Lys
            100                 105

<210> SEQ ID NO 90
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 90

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Glu Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

Phe Gly Gly Gly Thr Lys Val Glu Ile Lys
            100                 105

<210> SEQ ID NO 91
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 91

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Arg Leu Leu Ile
        35                  40                  45
```

-continued

```
Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Leu Thr
                85                  90                  95

Phe Gly Gly Gly Thr Lys Val Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 92

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
                20                  25                  30

Leu Ala Trp Tyr Gln Lys Lys Pro Gly Gln Ala Pro Arg Leu Leu Ile
            35                  40                  45

Tyr Gly Ala Ser Thr Arg Glu Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 93

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
                20                  25                  30

Leu Ala Trp Tyr Gln Lys Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 94
<211> LENGTH: 107
<212> TYPE: PRT
<213> ORGANISM: Artificial Sequence
```

-continued

```
<220> FEATURE:
<223> OTHER INFORMATION: An artificially synthesized sequence

<400> SEQUENCE: 94

Glu Ile Val Leu Thr Gln Ser Pro Ala Thr Leu Ser Val Ser Pro Gly
1               5                   10                  15

Glu Arg Ala Thr Leu Ser Cys Arg Ala Thr Arg Ser Val Arg Arg Asp
            20                  25                  30

Leu Ala Trp Tyr Gln Lys Lys Pro Gly Gln Ala Pro Arg Leu Leu Ile
        35                  40                  45

Tyr Gly Ala Ser Arg Arg Glu Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 95

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Arg Leu Leu Ile
        35                  40                  45

Tyr Gly Ala Ser Thr Arg Glu Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Pro Gly
                85                  90                  95

Thr Phe Gly Gly Gly Thr Lys Val Glu Ile Lys
            100                 105

<210> SEQ ID NO 96
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 96

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
    50                  55                  60
```

```
Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys
            100                 105
```

<210> SEQ ID NO 97
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 97

```
Glu Ile Val Leu Thr Gln Ser Pro Ala Thr Leu Ser Val Ser Pro Gly
1                   5                   10                  15

Glu Arg Ala Thr Leu Ser Cys Arg Ala Ser Arg Ser Val Arg Arg Glu
                20                  25                  30

Leu Ala Trp Tyr Gln Lys Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
            100                 105
```

<210> SEQ ID NO 98
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 98

```
Glu Ile Val Leu Thr Gln Ser Pro Ala Thr Leu Ser Val Ser Pro Gly
1                   5                   10                  15

Glu Arg Ala Thr Leu Ser Cys Arg Ala Ser Arg Ser Val Arg Arg Glu
                20                  25                  30

Leu Ala Trp Tyr Gln Gln Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
            100                 105
```

<210> SEQ ID NO 99
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 99

```
Glu Ile Val Leu Thr Gln Ser Pro Ala Thr Leu Ser Val Ser Pro Gly
1               5                   10                  15

Glu Arg Ala Thr Leu Ser Cys Arg Ala Thr Arg Ser Val Arg Arg Asp
            20                  25                  30

Leu Ala Trp Tyr Gln Gln Lys Pro Gly Gln Ala Pro Glu Leu Leu Ile
        35                  40                  45

Tyr Gly Ala Ser Arg Arg Glu Thr Gly Ile Pro Ala Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys
            100                 105
```

<210> SEQ ID NO 100
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 100

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ser Asn Thr Arg Ser Gly Thr Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115
```

<210> SEQ ID NO 101
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 101

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60
```

```
Gln Asn Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115

<210> SEQ ID NO 102
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 102

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Arg Val Ile Ser Asn Glu Glu Phe
        50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 103
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 103

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Val Ile Tyr Asn Glu Glu Phe
        50                  55                  60

Gln Gln Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115
```

<210> SEQ ID NO 104
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 104

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115

<210> SEQ ID NO 105
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 105

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Arg Ser Ile Tyr Asn Glu Glu Phe
    50                  55                  60

Gln Asp Arg Val Ile Met Thr Val Asp Ile Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
        115

<210> SEQ ID NO 106
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 106

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser
            115
```

```
<210> SEQ ID NO 107
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 107
```

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
    50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
            115
```

```
<210> SEQ ID NO 108
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 108
```

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Lys Phe
    50                  55                  60
```

```
Gln Asp Arg Val Ile Met Thr Val Asp Lys Ser Thr Asp Thr Ala Tyr
65                  70                  75                  80

Met Glu Leu Ser Glu Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
                100                 105                 110

Thr Leu Val Thr Val Ser Ser
        115

<210> SEQ ID NO 109
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 109

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
                20                  25                  30

Asn Met Asp Trp Val Arg Gln Ala Pro Gly Gln Gly Leu Glu Trp Met
        35                  40                  45

Gly Asp Ile Asn Thr Arg Ser Gly Arg Ser Ile Tyr Asn Arg Glu Phe
        50                  55                  60

Gln Asp Arg Val Ile Met Thr Val Asp Ile Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
                100                 105                 110

Thr Leu Val Thr Val Ser Ser
        115

<210> SEQ ID NO 110
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 110

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
                20                  25                  30

Asn Met Asp Trp Val Arg Lys Ala Pro Gly Gln Gly Leu Glu Trp Met
        35                  40                  45

Gly Asp Ile Asn Thr Arg Ser Gly Gly Val Ile Tyr Asn Glu Glu Phe
        50                  55                  60

Gln Asp Arg Leu Ile Met Thr Val Asp Lys Ser Thr Asp Thr Ala Tyr
65                  70                  75                  80

Met Glu Leu Ser Glu Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
                100                 105                 110

Thr Leu Val Thr Val Ser Ser
```

-continued

115

<210> SEQ ID NO 111
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 111

Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
            20                  25                  30

His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
            100                 105

<210> SEQ ID NO 112
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 112

Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
            20                  25                  30

His Trp Tyr His Gln Arg Pro Gly Gln Ala Pro Ile Leu Val Met Phe
        35                  40                  45

Gln Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
            100                 105

<210> SEQ ID NO 113
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 113

Ser Tyr Val Leu Thr Gln Pro Val Ser Val Ser Val Ala Arg Gly Gln
1               5                   10                  15

Thr Ala Thr Ile Thr Cys Thr Gly Asn His Ile Ser Asp Lys His Val
            20                  25                  30

His Trp Tyr His Gln Arg Pro Gly Gln Ala Pro Ile Leu Val Met Phe
        35                  40                  45

Gln Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Asp Tyr Thr
                85                  90                  95

Val Phe Gly Gly Gly Thr Lys Val Thr Val Val
                100                 105

<210> SEQ ID NO 114
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 114

Ser Tyr Val Leu Thr Gln Pro Val Ser Val Ser Val Ala Arg Gly Gln
1               5                   10                  15

Thr Ala Thr Ile Thr Cys Glu Gly Asn Gln Ile Ser Gln Lys Gln Val
                20                  25                  30

His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ala Val Val
                85                  90                  95

Phe Gly Gly Gly Thr Lys Val Thr Val Val
                100                 105

<210> SEQ ID NO 115
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 115

Ser Tyr Val Leu Thr Gln Pro Val Ser Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Glu Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
                100                 105

-continued

<210> SEQ ID NO 116
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 116

Ser Tyr Val Leu Thr Gln Pro Val Ser Val Ser Val Ala Leu Gly Gln
1               5                   10                  15

Thr Ala Thr Ile Thr Cys Glu Gly Asn Gln Ile Gly Ser Arg Glu Val
            20                  25                  30

His Trp Tyr His Glu Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                85                  90                  95

Phe Gly Gly Gly Thr Lys Val Thr Val Val
            100                 105

<210> SEQ ID NO 117
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 117

Ser Tyr Val Leu Thr Gln Pro Val Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Gln Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val
            100                 105

<210> SEQ ID NO 118
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 118

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Ile Tyr
        35                  40                  45

-continued

```
Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val
            100                 105

<210> SEQ ID NO 119
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 119

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Gln Arg Pro Gly Gln Ala Pro Ile Leu Val Ile Tyr
            35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val
            100                 105

<210> SEQ ID NO 120
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 120

Ser Tyr Glu Leu Thr Gln Pro Pro Ser Val Ser Val Ala Leu Gly Gln
1               5                   10                  15

Thr Ala Thr Ile Thr Cys Glu Gly Asn Gln Ile Gly Glu Lys Glu Val
                20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                85                  90                  95

Phe Gly Gly Gly Thr Lys Val Thr Val Val
            100                 105

<210> SEQ ID NO 121
<211> LENGTH: 107
<212> TYPE: PRT
```

-continued

```
<213> ORGANISM: Artificial Sequence
<220> FEATURE:
<223> OTHER INFORMATION: An artificially synthesized sequence

<400> SEQUENCE: 121

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Met Phe
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val
            100                 105

<210> SEQ ID NO 122
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 122

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Asp Arg Glu Asp His Gly Trp Ile Phe Asp Tyr Trp
            100                 105                 110

Gly Gln Gly Thr Leu Val Thr Val Ser Ser
        115                 120

<210> SEQ ID NO 123
<211> LENGTH: 323
<212> TYPE: PRT
<213> ORGANISM: Oryctolagus cuniculus

<400> SEQUENCE: 123

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
```

-continued

```
                50                    55                        60

Leu Ser Ser Val Val Ser Val Thr Ser Ser Ser Gln Pro Val Thr Cys
65                    70                        75                        80

Asn Val Ala His Pro Ala Thr Asn Thr Lys Val Asp Lys Thr Val Ala
                    85                        90                        95

Pro Ser Thr Cys Ser Lys Pro Thr Cys Pro Pro Pro Glu Leu Leu Gly
                    100                       105                       110

Gly Pro Ser Val Phe Ile Phe Pro Pro Lys Pro Lys Asp Thr Leu Met
            115                       120                       125

Ile Ser Arg Thr Pro Glu Val Thr Cys Val Val Val Asp Val Ser Gln
            130                       135                       140

Asp Asp Pro Glu Val Gln Phe Thr Trp Tyr Ile Asn Asn Glu Gln Val
145                       150                       155                       160

Arg Thr Ala Arg Pro Pro Leu Arg Glu Gln Gln Phe Asn Ser Thr Ile
                    165                       170                       175

Arg Val Val Ser Thr Leu Pro Ile Thr His Gln Asp Trp Leu Arg Gly
                    180                       185                       190

Lys Glu Phe Lys Cys Lys Val His Asn Lys Ala Leu Pro Ala Pro Ile
            195                       200                       205

Glu Lys Thr Ile Ser Lys Ala Arg Gly Gln Pro Leu Glu Pro Lys Val
            210                       215                       220

Tyr Thr Met Gly Pro Pro Arg Glu Glu Leu Ser Ser Arg Ser Val Ser
225                       230                       235                       240

Leu Thr Cys Met Ile Asn Gly Phe Tyr Pro Ser Asp Ile Ser Val Glu
                    245                       250                       255

Trp Glu Lys Asn Gly Lys Ala Glu Asp Asn Tyr Lys Thr Thr Pro Ala
                    260                       265                       270

Val Leu Asp Ser Asp Gly Ser Tyr Phe Leu Tyr Asn Lys Leu Ser Val
                    275                       280                       285

Pro Thr Ser Glu Trp Gln Arg Gly Asp Val Phe Thr Cys Ser Val Met
            290                       295                       300

His Glu Ala Leu His Asn His Tyr Thr Gln Lys Ser Ile Ser Arg Ser
305                       310                       315                       320

Pro Gly Lys
```

```
<210> SEQ ID NO 124
<211> LENGTH: 104
<212> TYPE: PRT
<213> ORGANISM: Oryctolagus cuniculus

<400> SEQUENCE: 124
```

```
Gly Asp Pro Val Ala Pro Thr Val Leu Ile Phe Pro Pro Ala Ala Asp
1                   5                       10                        15

Gln Val Ala Thr Gly Thr Val Thr Ile Val Cys Val Ala Asn Lys Tyr
                    20                        25                        30

Phe Pro Asp Val Thr Val Thr Trp Glu Val Asp Gly Thr Thr Gln Thr
            35                        40                        45

Thr Gly Ile Glu Asn Ser Lys Thr Pro Gln Asn Ser Ala Asp Cys Thr
            50                        55                        60

Tyr Asn Leu Ser Ser Thr Leu Thr Leu Thr Ser Thr Gln Tyr Asn Ser
65                        70                        75                        80

His Lys Glu Tyr Thr Cys Lys Val Thr Gln Gly Thr Thr Ser Val Val
                    85                        90                        95

Gln Ser Phe Asn Arg Gly Asp Cys
```

```
        100
```

```
<210> SEQ ID NO 125
<211> LENGTH: 969
<212> TYPE: DNA
<213> ORGANISM: Oryctolagus cuniculus

<400> SEQUENCE: 125
gggcaaccta aggctccatc agtcttccca ctggcccect gctgcgggga cacacccagc        60
tccacggtga ccctgggctg cctggtcaaa ggctacctcc cggagccagt gaccgtgacc       120
tggaactcgg gcaccctcac caatgggqta cgcaccttcc cgtccgtccg gcagtcctca       180
ggcctctact cgctgagcag cgtggtgagc gtgacctcaa gcagccagcc cgtcacctgc       240
aacgtggccc acccagccac caacaccaaa gtggacaaga ccgttgcacc ctcgacatgc       300
agcaagccca cgtgcccacc ccctgaactc ctgggggggac cgtctgtctt catcttcccc       360
ccaaaaccca aggacaccct catgatctca cgcaccccg aggtcacatg cgtggtggtg       420
gacgtgagcc aggatgaccc cgaggtgcag ttcacatggt acataaacaa cgagcaggtg       480
cgcaccgccc ggccgccgct acgggagcag cagttcaaca gcacgatccg cgtggtcagc       540
accctcccca tcacgcacca ggactggctg aggggcaaga agttcaagtg caaagtccac       600
aacaaggcac tcccggcccc catcgagaaa accatctcca aagccagagg gcagcccctg       660
gagccgaagg tctacaccat gggccctccc cgggaggagc tgagcagcag gtcggtcagc       720
ctgacctgca tgatcaacgg cttctaccct tccgacatct cggtggagtg ggagaagaac       780
gggaaggcag aggacaacta caagaccacg ccggccgtgc tggacagcga cggctcctac       840
ttcctctaca caagctctc agtgcccacg agtgagtggc agcggggcga cgtcttcacc       900
tgctccgtga tgcacgaggc cttgcacaac cactacacgc agaagtccat ctcccgctct       960
ccgggtaaa                                                              969

<210> SEQ ID NO 126
<211> LENGTH: 312
<212> TYPE: DNA
<213> ORGANISM: Oryctolagus cuniculus

<400> SEQUENCE: 126
ggtgatccag ttgcacctac tgtcctcatc ttcccaccag ctgctgatca ggtggcaact        60
ggaacagtca ccatcgtgtg tgtggcgaat aaatactttc ccgatgtcac cgtcacctgg       120
gaggtggatg gcaccaccca aacaactggc atcgagaaca gtaaaacacc gcagaattct       180
gcagattgta cctacaacct cagcagcact ctgacactga ccagcacaca gtacaacagc       240
cacaaagagt acacctgcaa ggtgacccag ggcacgacct cagtcgtcca gagcttcaat       300
aggggtgact gt                                                          312

<210> SEQ ID NO 127
<211> LENGTH: 323
<212> TYPE: PRT
<213> ORGANISM: Oryctolagus cuniculus

<400> SEQUENCE: 127

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
```

-continued

```
            35              40              45
Gly Val Arg Thr Phe Pro Ser Val Arg Gln Ser Ser Gly Leu Tyr Ser
    50              55              60

Leu Ser Ser Val Val Ser Val Thr Ser Ser Ser Gln Pro Val Thr Cys
65              70              75              80

Asn Val Ala His Pro Ala Thr Asn Thr Lys Val Asp Lys Thr Val Ala
                85              90              95

Pro Ser Thr Cys Ser Lys Pro Thr Cys Pro Pro Glu Leu Leu Gly
            100             105             110

Gly Pro Ser Val Phe Ile Phe Pro Pro Lys Pro Lys Asp Thr Leu Met
        115             120             125

Ile Ser Arg Thr Pro Glu Val Thr Cys Val Val Val Asp Val Ser Gln
    130             135             140

Asp Asp Pro Glu Val Gln Phe Thr Trp Tyr Ile Asn Asn Glu Gln Val
145             150             155             160

Arg Thr Ala Arg Pro Pro Leu Arg Glu Gln Gln Phe Asn Ser Thr Ile
                165             170             175

Arg Val Val Ser Thr Leu Pro Ile Thr His Gln Asp Trp Leu Arg Gly
            180             185             190

Lys Glu Phe Lys Cys Lys Val His Asn Lys Ala Leu Pro Ala Pro Ile
        195             200             205

Glu Lys Thr Ile Ser Lys Ala Arg Gly Gln Pro Leu Glu Pro Lys Val
    210             215             220

Tyr Thr Met Gly Pro Pro Arg Glu Glu Leu Ser Ser Arg Ser Val Ser
225             230             235             240

Leu Thr Cys Met Ile Asn Gly Phe Tyr Pro Ser Asp Ile Ser Val Glu
                245             250             255

Trp Glu Lys Asn Gly Lys Ala Glu Asp Asn Tyr Lys Thr Thr Pro Ala
            260             265             270

Val Leu Asp Ser Asp Gly Ser Tyr Phe Leu Tyr Asn Lys Leu Ser Val
            275             280             285

Pro Thr Ser Glu Trp Gln Arg Gly Asp Val Phe Thr Cys Ser Val Met
    290             295             300

His Glu Ala Leu His Asn His Tyr Thr Gln Lys Ser Ile Ser Arg Ser
305             310             315             320

Pro Gly Lys

<210> SEQ ID NO 128
<211> LENGTH: 104
<212> TYPE: PRT
<213> ORGANISM: Oryctolagus cuniculus

<400> SEQUENCE: 128

Gly Asp Pro Val Ala Pro Thr Val Leu Ile Phe Pro Pro Ala Ala Asp
1               5               10              15

Gln Val Ala Thr Gly Thr Val Thr Ile Val Cys Val Ala Asn Lys Tyr
            20              25              30

Phe Pro Asp Val Thr Val Thr Trp Glu Val Asp Gly Thr Thr Gln Thr
        35              40              45

Thr Gly Ile Glu Asn Ser Lys Thr Pro Gln Asn Ser Ala Asp Cys Thr
    50              55              60

Tyr Asn Leu Ser Ser Thr Leu Thr Leu Thr Ser Thr Gln Tyr Asn Ser
65              70              75              80

His Lys Glu Tyr Thr Cys Lys Val Thr Gln Gly Thr Thr Ser Val Val
```

-continued

```
                    85                  90                  95

Gln Ser Phe Asn Arg Gly Asp Cys
                100

<210> SEQ ID NO 129
<211> LENGTH: 969
<212> TYPE: DNA
<213> ORGANISM: Oryctolagus cuniculus

<400> SEQUENCE: 129
gggcaaccta aggctccatc agtcttccca ctggcccccct gctgcgggga cacacccagc      60
tccacggtga ccctgggctg cctggtcaaa ggctacctcc cggagccagt gaccgtgacc     120
tggaactcgg gcaccctcac caatggggta cgcaccttcc cgtccgtccg gcagtcctca     180
ggcctctact cgctgagcag cgtggtgagc gtgacctcaa gcagccagcc cgtcacctgc     240
aacgtggccc acccagccac caacaccaaa gtggacaaga ccgttgcacc ctcgacatgc     300
agcaagccca cgtgcccacc ccctgaactc ctggggggac cgtctgtctt catcttcccc     360
ccaaaaccca aggacaccct catgatctca cgcacccccg aggtcacatg cgtggtggtg     420
gacgtgagcc aggatgaccc cgaggtgcag ttcacatggt acataaacaa cgagcaggtg     480
cgcaccgccc ggccgccgct acgggagcag cagttcaaca gcacgatccg cgtggtcagc     540
accctcccca tcacgcacca ggactggctg aggggcaagg agttcaagtg caaagtccac     600
aacaaggcac tcccggcccc catcgagaaa accatctcca agccagagg gcagcccctg     660 gagccgaagg tctacaccat gggccctccc cgggaggagc tgagcagcag gtcggtcagc     720
ctgacctgca tgatcaacgg cttctaccct tccgacatct cggtggagtg ggagaagaac     780
gggaaggcag aggacaacta caagaccacg ccggccgtgc tggacagcga cggctcctac     840
ttcctctaca caagctctc agtgcccacg agtgagtggc agcggggcga cgtcttcacc     900
tgctccgtga tgcacgaggc cttgcacaac cactacacgc agaagtccat ctcccgctct     960
ccgggtaaa                                                             969

<210> SEQ ID NO 130
<211> LENGTH: 312
<212> TYPE: DNA
<213> ORGANISM: Oryctolagus cuniculus

<400> SEQUENCE: 130
ggtgatccag ttgcacctac tgtcctcatc ttcccaccag ctgctgatca ggtggcaact      60
ggaacagtca ccatcgtgtg tgtggcgaat aaatactttc ccgatgtcac cgtcacctgg     120
gaggtggatg gcaccaccca aacaactggc atcgagaaca gtaaacacc gcagaattct     180 gcagattgta cctacaacct cagcagcact ctgacactga ccagcacaca gtacaacagc     240
cacaaagagt acacctgcaa ggtgacccag ggcacgacct cagtcgtcca gagcttcaat     300
aggggtgact gt                                                         312

<210> SEQ ID NO 131
<211> LENGTH: 441
<212> TYPE: PRT
<213> ORGANISM: Oryctolagus cuniculus

<400> SEQUENCE: 131

Arg Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
```

```
                      20                    25                    30
Tyr Trp Val Cys Trp Val Arg Gln Ala Pro Gly Lys Gly Leu Glu Trp
            35                    40                    45
Ile Gly Cys Ile Asp Thr Gly Ser Gly Asn Thr Ala Tyr Ala Ser Trp
        50                    55                    60
Ala Lys Gly Arg Phe Thr Ile Ser Lys Thr Ser Ser Thr Thr Val Thr
65                    70                    75                    80
Leu Gln Met Thr Ser Leu Thr Ala Ala Asp Thr Ala Thr Tyr Phe Cys
                85                    90                    95
Ala Arg Gly Tyr Val Val Ala His Phe Asn Leu Trp Gly Pro Gly Thr
                100                   105                   110
Leu Val Thr Val Ser Ser Gly Gln Pro Lys Ala Pro Ser Val Phe Pro
                115                   120                   125
Leu Ala Pro Cys Cys Gly Asp Thr Pro Ser Ser Thr Val Thr Leu Gly
        130                   135                   140
Cys Leu Val Lys Gly Tyr Leu Pro Glu Pro Val Thr Val Thr Trp Asn
145                   150                   155                   160
Ser Gly Thr Leu Thr Asn Gly Val Arg Thr Phe Pro Ser Val Arg Gln
                165                   170                   175
Ser Ser Gly Leu Tyr Ser Leu Ser Ser Val Val Ser Val Thr Ser Ser
            180                   185                   190
Ser Gln Pro Val Thr Cys Asn Val Ala His Pro Ala Thr Asn Thr Lys
            195                   200                   205
Val Asp Lys Thr Val Ala Pro Ser Thr Cys Ser Lys Pro Thr Cys Pro
        210                   215                   220
Pro Pro Glu Leu Leu Gly Gly Pro Ser Val Phe Ile Phe Pro Pro Lys
225                   230                   235                   240
Pro Lys Asp Thr Leu Met Ile Ser Arg Thr Pro Glu Val Thr Cys Val
                245                   250                   255
Val Val Asp Val Ser Gln Asp Asp Pro Glu Val Gln Phe Thr Trp Tyr
                260                   265                   270
Ile Asn Asn Glu Gln Val Arg Thr Ala Arg Pro Pro Leu Arg Glu Gln
            275                   280                   285
Gln Phe Asn Ser Thr Ile Arg Val Val Ser Thr Leu Pro Ile Thr His
        290                   295                   300
Gln Asp Trp Leu Arg Gly Lys Glu Phe Lys Cys Lys Val His Asn Lys
305                   310                   315                   320
Ala Leu Pro Ala Pro Ile Glu Lys Thr Ile Ser Lys Ala Arg Gly Gln
                325                   330                   335
Pro Leu Glu Pro Lys Val Tyr Thr Met Gly Pro Pro Arg Glu Glu Leu
            340                   345                   350
Ser Ser Arg Ser Val Ser Leu Thr Cys Met Ile Asn Gly Phe Tyr Pro
            355                   360                   365
Ser Asp Ile Ser Val Glu Trp Glu Lys Asn Gly Lys Ala Glu Asp Asn
        370                   375                   380
Tyr Lys Thr Thr Pro Ala Val Leu Asp Ser Asp Gly Ser Tyr Phe Leu
385                   390                   395                   400
Tyr Asn Lys Leu Ser Val Pro Thr Ser Glu Trp Gln Arg Gly Asp Val
                405                   410                   415
Phe Thr Cys Ser Val Met His Glu Ala Leu His Asn His Tyr Thr Gln
            420                   425                   430
Lys Ser Ile Ser Arg Ser Pro Gly Lys
            435                   440
```

```
<210> SEQ ID NO 132
<211> LENGTH: 215
<212> TYPE: PRT
<213> ORGANISM: Oryctolagus cuniculus

<400> SEQUENCE: 132

Ala Asp Val Val Met Thr Gln Thr Pro Ala Ser Val Ser Glu Pro Val
1               5                   10                  15

Gly Gly Thr Val Thr Ile Lys Cys Gln Ala Ser Glu Asp Ile Glu Arg
            20                  25                  30

Tyr Leu Ala Trp Tyr Gln Gln Lys Pro Gly Gln Pro Pro Lys Leu Leu
        35                  40                  45

Ile Asp Asp Ala Ser Asp Leu Ala Ser Gly Val Pro Ser Arg Phe Lys
    50                  55                  60

Gly Ser Gly Ser Gly Thr Glu Tyr Thr Leu Thr Ile Ser Ala Leu Glu
65                  70                  75                  80

Cys Ala Asp Ala Ala Thr Tyr Tyr Cys Gln Ser Tyr Tyr Ala Ile Ser
                85                  90                  95

Thr Tyr Gly Val Ala Phe Gly Gly Gly Thr Glu Val Val Val Lys Gly
            100                 105                 110

Asp Pro Val Ala Pro Thr Val Leu Ile Phe Pro Pro Ala Ala Asp Gln
        115                 120                 125

Val Ala Thr Gly Thr Val Thr Ile Val Cys Val Ala Asn Lys Tyr Phe
    130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
        195                 200                 205

Ser Phe Asn Arg Gly Asp Cys
    210                 215

<210> SEQ ID NO 133
<211> LENGTH: 1326
<212> TYPE: DNA
<213> ORGANISM: Oryctolagus cuniculus

<400> SEQUENCE: 133
cgggagcaac tggaggagtc cggggagac ctggtcaagc ctgagggatc cctgacactc        60
acctgcacag cctctggatt ctccttcagt agcagctact gggtgtgctg ggtccgccag       120
gctccaggga aggggctgga gtggatcgga tgcattgata ctggtagtgg taacactgcc       180
tacgcgagct gggcgaaagg ccgattcacc atctccaaga cctcgtcgac cacggtgact       240
ctgcaaatga ccagtctgac agccgcggac acggccacct atttctgtgc gagaggttat       300
gttgttgctc actttaactt gtggggccca ggcaccctgg tcaccgtctc ctccgggcaa       360
cctaaggctc catcagtctt cccactggcc ccctgctgcg gggacacacc cagtccacg       420 gtgaccctgg gctgcctggt caaaggctac ctcccggagc cagtgaccgt gacctggaac       480
tcgggcaccc tcaccaatgg ggtacgcacc ttcccgtccg tccggcagtc ctcaggcctc       540
tactcgctga gcagcgtggt gagcgtgacc tcaagcagcc agcccgtcac ctgcaacgtg       600
```

-continued

```
gcccacccag ccaccaacac caaagtggac aagaccgttg caccctcgac atgcagcaag    660
cccacgtgcc cacccctga  actcctgggg ggaccgtctg tcttcatctt cccccaaaa     720 cccaaggaca ccctcatgat ctcacgcacc cccgaggtca catgcgtggt ggtggacgtg    780
agccaggatg accccgaggt gcagttcaca tggtacataa acaacgagca ggtgcgcacc    840
gcccggccgc cgctacggga gcagcagttc aacagcacga tccgcgtggt cagcaccctc    900
cccatcacgc accaggactg gctgaggggc aaggagttca gtgcaaagt  ccacaacaag    960 gcactcccgg cccccatcga gaaaaccatc tccaaagcca gagggcagcc cctggagccg   1020
aaggtctaca ccatgggccc tccccgggag gagctgagca gcaggtcggt cagcctgacc   1080
tgcatgatca acggcttcta cccttccgac atctcggtgg agtgggagaa gaacgggaag   1140
gcagaggaca actacaagac cacgcccgcc gtgctggaca cgacggctc  ctacttcctc   1200 tacaacaagc tctcagtgcc cacgagtgag tggcagcggg gcgacgtctt cacctgctcc   1260
gtgatgcacg aggccttgca caaccactac acgcagaagt ccatctcccg ctctccgggt   1320
aaatga                                                             1326
```

<210> SEQ ID NO 134
<211> LENGTH: 648
<212> TYPE: DNA
<213> ORGANISM: Oryctolagus cuniculus

<400> SEQUENCE: 134

```
gccgatgttg tgatgaccca gactccagcc tccgtgtctg aacctgtggg aggcacagtc     60
accatcaagt gccaggccag tgaggacatt gaaaggtatt tagcctggta tcagcagaaa    120
ccagggcagc ctcccaagct cctgatcgat gatgcatccg atctggcatc tggggtccca    180
tcgcggttca aaggcagtgg atctgggaca gaatacactc tcaccatcag cgccctggag    240
tgtgccgatg ctgccactta ctactgtcaa agctattatg ctattagtac ttatggtgtt    300
gctttcggcg gagggaccga ggtggtggtc aaaggtgatc cagttgcacc tactgtcctc    360 atcttccac cagctgctga tcaggtggca actggaacag tcaccatcgt gtgtgtggcg    420
aataaatact ttcccgatgt caccgtcacc tgggaggtgg atggcaccac ccaaacaact    480
ggcatcgaga acagtaaaac accgcagaat tctgcagatt gtacctacaa cctcagcagc    540
actctgacac tgaccagcac acagtacaac agccacaaag agtacacctg caaggtgacc    600
cagggcacga cctcagtcgt ccagagcttc aataggggtg actgttag              648
```

<210> SEQ ID NO 135
<211> LENGTH: 441
<212> TYPE: PRT
<213> ORGANISM: Oryctolagus cuniculus

<400> SEQUENCE: 135

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Ser Trp Val Arg Gln Ala Pro Gly Lys Gly Leu Glu Tyr Ile Gly
        35                  40                  45

Tyr Ile Thr Val Asn Gly Val Thr Tyr Tyr Ala Asn Trp Ala Lys Gly
    50                  55                  60

Arg Phe Thr Ile Ser Lys Thr Ser Thr Thr Val Asp Leu Lys Ile Ser
65                  70                  75                  80
```

-continued

```
Ser Pro Thr Thr Glu Asp Thr Ala Thr Tyr Phe Cys Ala Arg Asp Gln
            85              90                  95

Tyr Ile Asn Asn Gly Gly Ala Glu Phe Asn Ile Trp Gly Pro Gly Thr
            100             105             110

Leu Val Thr Val Ser Ser Gly Gln Pro Lys Ala Pro Ser Val Phe Pro
            115             120             125

Leu Ala Pro Cys Cys Gly Asp Thr Pro Ser Ser Thr Val Thr Leu Gly
    130             135             140

Cys Leu Val Lys Gly Tyr Leu Pro Glu Pro Val Thr Val Thr Trp Asn
145             150             155             160

Ser Gly Thr Leu Thr Asn Gly Val Arg Thr Phe Pro Ser Val Arg Gln
            165             170             175

Ser Ser Gly Leu Tyr Ser Leu Ser Ser Val Val Ser Val Thr Ser Ser
            180             185             190

Ser Gln Pro Val Thr Cys Asn Val Ala His Pro Ala Thr Asn Thr Lys
            195             200             205

Val Asp Lys Thr Val Ala Pro Ser Thr Cys Ser Lys Pro Thr Cys Pro
    210             215             220

Pro Pro Glu Leu Leu Gly Gly Pro Ser Val Phe Ile Phe Pro Pro Lys
225             230             235             240

Pro Lys Asp Thr Leu Met Ile Ser Arg Thr Pro Glu Val Thr Cys Val
            245             250             255

Val Val Asp Val Ser Gln Asp Asp Pro Glu Val Gln Phe Thr Trp Tyr
            260             265             270

Ile Asn Asn Glu Gln Val Arg Thr Ala Arg Pro Pro Leu Arg Glu Gln
            275             280             285

Gln Phe Asn Ser Thr Ile Arg Val Val Ser Thr Leu Pro Ile Thr His
    290             295             300

Gln Asp Trp Leu Arg Gly Lys Glu Phe Lys Cys Lys Val His Asn Lys
305             310             315             320

Ala Leu Pro Ala Pro Ile Glu Lys Thr Ile Ser Lys Ala Arg Gly Gln
            325             330             335

Pro Leu Glu Pro Lys Val Tyr Thr Met Gly Pro Pro Arg Glu Glu Leu
            340             345             350

Ser Ser Arg Ser Val Ser Leu Thr Cys Met Ile Asn Gly Phe Tyr Pro
            355             360             365

Ser Asp Ile Ser Val Glu Trp Glu Lys Asn Gly Lys Ala Glu Asp Asn
    370             375             380

Tyr Lys Thr Thr Pro Ala Val Leu Asp Ser Asp Gly Ser Tyr Phe Leu
385             390             395             400

Tyr Asn Lys Leu Ser Val Pro Thr Ser Glu Trp Gln Arg Gly Asp Val
            405             410             415

Phe Thr Cys Ser Val Met His Glu Ala Leu His Asn His Tyr Thr Gln
            420             425             430

Lys Ser Ile Ser Arg Ser Pro Gly Lys
            435             440
```

<210> SEQ ID NO 136
<211> LENGTH: 214
<212> TYPE: PRT
<213> ORGANISM: Oryctolagus cuniculus

<400> SEQUENCE: 136

```
Ala Tyr Asp Met Thr Gln Thr Pro Ser Phe Val Glu Ala Ala Val Gly
1               5               10              15
```

```
Gly Thr Val Thr Ile Lys Cys Gln Ala Ser Glu Ser Ile Ser Ser Trp
        20              25              30

Leu Ser Trp Tyr Gln Gln Lys Pro Gly Gln Pro Pro Lys Leu Leu Ile
        35              40              45

Tyr Gln Ala Ser Thr Leu Ala Ser Gly Val Ser Ser Arg Phe Lys Gly
    50              55              60

Ser Gly Ser Gly Thr Gln Phe Thr Leu Thr Ile Ser Asp Leu Glu Cys
65              70              75              80

Ala Asp Ala Ala Thr Tyr Tyr Cys Gln Gln Gly Tyr Ser Tyr Gly Asp
            85              90              95

Val Asp Asn Ala Phe Gly Gly Gly Thr Glu Val Val Val Lys Gly Asp
            100             105             110

Pro Val Ala Pro Thr Val Leu Ile Phe Pro Pro Ala Ala Asp Gln Val
        115             120             125

Ala Thr Gly Thr Val Thr Ile Val Cys Val Ala Asn Lys Tyr Phe Pro
    130             135             140

Asp Val Thr Val Thr Trp Glu Val Asp Gly Thr Thr Gln Thr Thr Gly
145             150             155             160

Ile Glu Asn Ser Lys Thr Pro Gln Asn Ser Ala Asp Cys Thr Tyr Asn
            165             170             175

Leu Ser Ser Thr Leu Thr Leu Thr Ser Thr Gln Tyr Asn Ser His Lys
            180             185             190

Glu Tyr Thr Cys Lys Val Thr Gln Gly Thr Thr Ser Val Val Gln Ser
        195             200             205

Phe Asn Arg Gly Asp Cys
    210
```

```
<210> SEQ ID NO 137
<211> LENGTH: 1326
<212> TYPE: DNA
<213> ORGANISM: Oryctolagus cuniculus

<400> SEQUENCE: 137
cagtcggtgg aggagtccgg gggtcgcctg gtcacgcctg ggacacccct gacactcacc      60
tgcacagtct ctggattctc cctcagcagc tacgacatga gctgggtccg ccaggctcca     120
ggaaaggggc tggagtacat cggatacatt actgttaatg gtgtcacata ctacgcgaac     180
tgggcgaaag gccgattcac catctccaaa acctcgacca cggtggatct gaaaatctcc     240
agtccgacaa ccgaggacac ggccacctat ttctgtgcca gagatcaata tattaataat     300
ggtggtgctg aatttaacat ctggggccca ggcaccctgg tcaccgtctc ctccgggcaa     360
cctaaggctc catcagtctt cccactggcc cctgctgcg gggacacacc cagctccacg     420
gtgaccctgg ctgcctggt caaaggctac ctcccggagc cagtgaccgt gacctggaac     480
tcgggcaccc tcaccaatgg ggtacgcacc ttcccgtccg tccggcagtc ctcaggcctc     540
tactcgctga gcagcgtggt gagcgtgacc tcaagcagcc agcccgtcac ctgcaacgtg     600
gcccacccag ccaccaacac caaagtggac aagaccgttg caccctcgac atgcagcaag     660
cccacgtgcc caccccctga actcctgggg ggaccgtctg tcttcatctt cccccccaaaa     720 cccaaggaca ccctcatgat ctcacgcacc cccgaggtca catgcgtggt ggtggacgtg     780
agccaggatg accccgaggt gcagttcaca tggtacataa acaacgagca ggtgcgcacc     840
gcccggccgc cgctacggga gcagcagttc aacagcacga tccgcgtggt cagcaccctc     900
cccatcacgc accaggactg gctgagggc aaggagttca gtgcaaagt ccacaacaag     960
```

```
gcactcccgg cccccatcga gaaaaccatc tccaaagcca gagggcagcc cctggagccg        1020
aaggtctaca ccatgggccc tccccgggag gagctgagca gcaggtcggt cagcctgacc        1080
tgcatgatca acggcttcta cccttccgac atctcggtgg agtgggagaa gaacgggaag        1140
gcagaggaca actacaagac cacgccggcc gtgctggaca cgacggctc ctacttcctc         1200 tacaacaagc tctcagtgcc cacgagtgag tggcagcggg gcgacgtctt cacctgctcc        1260
gtgatgcacg aggccttgca caaccactac acgcagaagt ccatctcccg ctctccgggt        1320
aaatga                                                                    1326
```

<210> SEQ ID NO 138
<211> LENGTH: 645
<212> TYPE: DNA
<213> ORGANISM: Oryctolagus cuniculus

<400> SEQUENCE: 138

```
gcctatgata tgacccagac tccatccttc gtggaggcag ctgtgggagg cacagtcacc          60
atcaagtgcc aggccagtga gagcattagc agttggttat cctggtatca gcagaaacca         120
gggcagcctc ccaagctcct gatctaccag gcatccactt ggcatctgg ggtctcatcg          180 cggttcaaag gcagtggatc tgggacacag ttcactctca ccatcagcga cctggagtgt         240
gccgatgctg ccacttacta ttgtcaacag ggttatagtt atggtgatgt tgataatgct         300
ttcggcggag ggaccgaggt ggtggtcaaa ggtgatccag ttgcacctac tgtcctcatc         360
ttcccaccag ctgctgatca ggtggcaact ggaacagtca ccatcgtgtg tgtggcgaat         420
aaatactttc cgatgtcac cgtcacctgg gaggtggatg caccaccca aacaactggc          480 atcgagaaca gtaaacacc gcagaattct gcagattgta cctacaacct cagcagcact         540
ctgacactga ccagcacaca gtacaacagc cacaaagagt acacctgcaa ggtgacccag         600
ggcacgacct cagtcgtcca gagcttcaat aggggtgact gttag                        645
```

<210> SEQ ID NO 139
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 139

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
    130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Tyr
            165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
            195             200             205

Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Lys Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
            275             280             285

Lys Leu Thr Val Asp Lys Ser Arg Trp Gln Glu Gly Asn Val Phe Ser
    290             295             300

Cys Ser Val Leu His Glu Ala Leu His Ala His Tyr Thr Arg Lys Glu
305             310             315             320

Leu Ser Leu Ser Pro
            325
```

```
<210> SEQ ID NO 140
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 140
```

```
Arg Thr Val Ala Ala Pro Ser Val Phe Ile Phe Pro Pro Ser Asp Glu
1               5               10              15

Gln Leu Lys Ser Gly Thr Ala Glu Val Val Cys Leu Leu Asn Asn Phe
            20              25              30

Tyr Pro Arg Glu Ala Lys Val Gln Trp Lys Val Asp Asn Ala Leu Gln
            35              40              45

Ser Gly Asn Ser Gln Glu Ser Val Thr Glu Gln Asp Ser Lys Asp Ser
    50              55              60

Thr Tyr Ser Leu Ser Ser Thr Leu Glu Leu Ser Lys Ala Asp Tyr Glu
65              70              75              80

Lys His Lys Val Tyr Ala Cys Glu Val Thr His Gln Gly Leu Ser Ser
            85              90              95

Pro Val Thr Lys Ser Phe Asn Arg Gly Glu Cys
            100             105
```

```
<210> SEQ ID NO 141
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 141
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Leu His Glu Ala Leu His Ala His Tyr Thr Arg Glu Glu
305                 310                 315                 320

Leu Ser Leu Ser Pro
                325
```

```
<210> SEQ ID NO 142
<211> LENGTH: 106
<212> TYPE: PRT
<213> ORGANISM: Artificial Sequence
<220> FEATURE:
<223> OTHER INFORMATION: An artificially synthesized sequence

<400> SEQUENCE: 142

Gly Gln Pro Lys Ala Ala Pro Ser Val Thr Leu Phe Pro Pro Ser Ser
1               5                   10                  15

Glu Glu Leu Gln Ala Asn Lys Ala Lys Leu Val Cys Leu Ile Ser Asp
            20                  25                  30
```

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
     50                  55                  60

Lys Tyr Ala Ala Ser Ser Tyr Leu Lys Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
             100                 105

<210> SEQ ID NO 143
<211> LENGTH: 448
<212> TYPE: PRT
<213> ORGANISM: Artificial Sequence
<220> FEATURE:
<223> OTHER INFORMATION: An artificially synthesized sequence

<400> SEQUENCE: 143

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
             20                  25                  30

Asp Ile Gln Trp Val Arg Gln Ala Pro Gly Lys Gly Leu Glu Trp Val
         35                  40                  45

Ser Ser Ile Ser Pro Ser Gly Gln Ser Thr Tyr Tyr Arg Arg Glu Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Thr Gly Arg Glu Tyr Asp Gly Gly Trp Tyr Phe Asp Tyr
             100                 105                 110

Trp Gly Gln Gly Thr Leu Val Thr Val Ser Ser Ala Ser Thr Lys Gly
         115                 120                 125

Pro Ser Val Phe Pro Leu Ala Pro Cys Ser Arg Ser Thr Ser Glu Ser
     130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Lys Ser Ser Gly Leu Tyr Ser Leu Ser Ser Val Val
             180                 185                 190

Thr Val Pro Ser Ser Ser Leu Gly Thr Gln Thr Tyr Thr Cys Asn Val
             195                 200                 205

Asp His Lys Pro Ser Asn Thr Lys Val Asp Lys Arg Val Glu Ser Lys
     210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
     275                 280                 285

```
Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Gly Leu Pro Ser Ser Ile Glu
            325             330             335

Lys Thr Ile Ser Lys Ala Lys Gly Gln Pro Arg Glu Pro Gln Val Tyr
            340             345             350

Thr Leu Pro Pro Ser Gln Lys Glu Met Thr Lys Asn Gln Val Ser Leu
            355             360             365

Thr Cys Leu Val Lys Gly Phe Tyr Pro Ser Asp Ile Ala Val Glu Trp
            370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Glu Gly Asn Val Phe Ser Cys Ser Val Leu His
            420             425             430

Glu Ala Leu His Ala His Tyr Thr Arg Lys Glu Leu Ser Leu Ser Pro
            435             440             445
```

```
<210> SEQ ID NO 144
<211> LENGTH: 448
<212> TYPE: PRT
<213> ORGANISM: Artificial Sequence
<220> FEATURE:
<223> OTHER INFORMATION: An artificially synthesized sequence

<400> SEQUENCE: 144
```

```
Gln Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Tyr Tyr
            20              25              30

Asp Ala Gln Trp Val Arg Gln Ala Pro Gly Lys Gly Leu Glu Trp Val
            35              40              45

Ser Ser Ile Ser Pro Ser Gly Gln Ser Thr Tyr Tyr Arg Arg Glu Val
            50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Arg Thr Gly Ser Glu Asp Gly Ala Gly Trp Tyr Phe Asp Tyr
            100             105             110

Trp Gly Gln Gly Thr Leu Val Thr Val Ser Ser Ala Ser Thr Lys Gly
            115             120             125

Pro Ser Val Phe Pro Leu Ala Pro Cys Ser Arg Ser Thr Ser Glu Ser
            130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
                165             170             175

Pro Ala Val Leu Lys Ser Ser Gly Leu Tyr Ser Leu Ser Ser Val Val
            180             185             190

Thr Val Pro Ser Ser Ser Leu Gly Thr Gln Thr Tyr Thr Cys Asn Val
            195             200             205
```

-continued

```
Asp His Lys Pro Ser Asn Thr Lys Val Asp Lys Arg Val Glu Ser Lys
    210             215                 220

Tyr Gly Pro Pro Cys Pro Cys Pro Ala Pro Glu Phe Leu Gly Gly
225             230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305             310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Glu Gly Asn Val Phe Ser Cys Ser Val Leu His
            420                 425                 430

Glu Ala Leu His Ala His Tyr Thr Arg Lys Glu Leu Ser Leu Ser Pro
            435                 440                 445

<210> SEQ ID NO 145
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 145

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Arg Arg Thr Gly Arg Glu Asp Gly Gly Trp His Phe Asp Tyr Trp
            100                 105                 110

Gly Gln Gly Thr Leu Val Thr Val Ser Ser Ala Ser Thr Lys Gly Pro
            115                 120                 125
```

-continued

```
Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Lys Ser Ser Gly Leu Tyr Ser Leu Ser Ser Val Val Thr
                180                 185                 190

Val Pro Ser Ser Ser Leu Gly Thr Gln Thr Tyr Thr Cys Asn Val Asp
                195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Lys Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Leu His Glu
                420                 425                 430

Ala Leu His Ala His Tyr Thr Arg Lys Glu Leu Ser Leu Ser Pro
                435                 440                 445
```

<210> SEQ ID NO 146
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 146

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
                20                  25                  30

Asp Ile Gln Trp Val Arg Glu Ala Pro Gly Lys Gly Leu Glu Trp Val
                35                  40                  45
```

```
Ser Ser Ile Ser Pro Ser Gly Gln Ser Thr Tyr Tyr Arg Arg Glu Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Arg Thr Gly Arg Glu Glu Gly Gly Trp Ile Phe Asp Tyr Trp
            100             105             110

Gly Gln Gly Thr Leu Val Thr Val Ser Ser Ala Ser Thr Lys Gly Pro
        115             120             125

Ser Val Phe Pro Leu Ala Pro Cys Ser Arg Ser Thr Ser Glu Ser Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Lys Ser Ser Gly Leu Tyr Ser Leu Ser Ser Val Val Thr
            180             185             190

Val Pro Ser Ser Ser Leu Gly Thr Gln Thr Tyr Thr Cys Asn Val Asp
        195             200             205

His Lys Pro Ser Asn Thr Lys Val Asp Lys Arg Val Glu Ser Lys Tyr
    210             215             220

Gly Pro Pro Cys Pro Pro Cys Pro Ala Pro Glu Phe Leu Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser Gln Glu Asp
            260             265             270

Pro Glu Val Gln Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Gly Leu Pro Ser Ser Ile Glu Lys
            325             330             335

Thr Ile Ser Lys Ala Lys Gly Gln Pro Arg Glu Pro Gln Val Tyr Thr
            340             345             350

Leu Pro Pro Ser Gln Lys Glu Met Thr Lys Asn Gln Val Ser Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Glu Gly Asn Val Phe Ser Cys Ser Val Leu His Glu
            420             425             430

Ala Leu His Ala His Tyr Thr Arg Lys Glu Leu Ser Leu Ser Pro
        435             440             445
```

<210> SEQ ID NO 147
<211> LENGTH: 447

```
<212> TYPE: PRT
<213> ORGANISM: Artificial Sequence
<220> FEATURE:
<223> OTHER INFORMATION: An artificially synthesized sequence

<400> SEQUENCE: 147

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Glu Gly Gly Trp Ile Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Lys Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
            195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Lys Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

-continued

```
Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Glu Gly Asn Val Phe Ser Cys Ser Val Leu His Glu
            420             425             430

Ala Leu His Ala His Tyr Thr Arg Lys Glu Leu Ser Leu Ser Pro
        435             440             445

<210> SEQ ID NO 148
<211> LENGTH: 447
<212> TYPE: PRT
<213> ORGANISM: Artificial Sequence
<220> FEATURE:
<223> OTHER INFORMATION: An artificially synthesized sequence

<400> SEQUENCE: 148

Gln Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser His Tyr
            20              25              30

Asp Ile Gln Trp Val Arg Gln Ala Pro Gly Lys Gly Leu Glu Trp Val
        35              40              45

Ser Ser Ile Ser Pro Ser Gly Gln Ser Thr Tyr Tyr Arg Arg Glu Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Arg Thr Asp Arg Glu Asp His Gly Trp Ile Phe Asp Tyr Trp
            100             105             110

Gly Gln Gly Thr Leu Val Thr Val Ser Ser Ala Ser Thr Lys Gly Pro
        115             120             125

Ser Val Phe Pro Leu Ala Pro Cys Ser Arg Ser Thr Ser Glu Ser Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Lys Ser Ser Gly Leu Tyr Ser Leu Ser Ser Val Val Thr
            180             185             190

Val Pro Ser Ser Ser Leu Gly Thr Gln Thr Tyr Thr Cys Asn Val Asp
    195             200             205

His Lys Pro Ser Asn Thr Lys Val Asp Lys Arg Val Glu Ser Lys Tyr
    210             215             220

Gly Pro Pro Cys Pro Pro Cys Pro Ala Pro Glu Phe Leu Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser Gln Glu Asp
            260             265             270

Pro Glu Val Gln Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300
```

```
Val Ser Val Leu Thr Val Leu His Gln Asp Trp Leu Asn Gly Lys Glu
305             310             315             320

Tyr Lys Cys Lys Val Ser Asn Lys Gly Leu Pro Ser Ser Ile Glu Lys
            325             330             335

Thr Ile Ser Lys Ala Lys Gly Gln Pro Arg Glu Pro Gln Val Tyr Thr
            340             345             350

Leu Pro Pro Ser Gln Lys Glu Met Thr Lys Asn Gln Val Ser Leu Thr
            355             360             365

Cys Leu Val Lys Gly Phe Tyr Pro Ser Asp Ile Ala Val Glu Trp Glu
            370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Glu Gly Asn Val Phe Ser Cys Ser Val Leu His Glu
            420             425             430

Ala Leu His Ala His Tyr Thr Arg Lys Glu Leu Ser Leu Ser Pro
            435             440             445
```

```
<210> SEQ ID NO 149
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 149
```

```
Glu Ile Val Leu Thr Gln Ser Pro Ala Thr Leu Ser Val Ser Pro Gly
1               5               10              15

Glu Arg Ala Thr Leu Ser Cys Arg Ala Ser Gln Ser Val Arg Arg Asp
            20              25              30

Leu Ala Trp Tyr Gln Gln Lys Pro Gly Gln Ala Pro Arg Leu Leu Ile
            35              40              45

Tyr Gly Ala Ser Arg Arg Ala Thr Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys Gln Gln Tyr Lys Ser Pro Leu Thr
            85              90              95

Phe Gly Gly Gly Thr Lys Val Glu Ile Lys Arg Thr Val Ala Ala Pro
            100             105             110

Ser Val Phe Ile Phe Pro Pro Ser Asp Glu Gln Leu Lys Ser Gly Thr
            115             120             125

Ala Glu Val Val Cys Leu Leu Asn Asn Phe Tyr Pro Arg Glu Ala Lys
            130             135             140

Val Gln Trp Lys Val Asp Asn Ala Leu Gln Ser Gly Asn Ser Gln Glu
145             150             155             160

Ser Val Thr Glu Gln Asp Ser Lys Asp Ser Thr Tyr Ser Leu Ser Ser
            165             170             175

Thr Leu Glu Leu Ser Lys Ala Asp Tyr Glu Lys His Lys Val Tyr Ala
            180             185             190

Cys Glu Val Thr His Gln Gly Leu Ser Ser Pro Val Thr Lys Ser Phe
            195             200             205

Asn Arg Gly Glu Cys
    210
```

<210> SEQ ID NO 150
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 150

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Arg Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Glu Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Glu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 151
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 151

Glu Ile Val Leu Thr Gln Ser Pro Ala Thr Leu Ser Val Ser Pro Gly
1               5                   10                  15

Glu Arg Ala Thr Leu Ser Cys Arg Ala Thr Gln Ser Val Arg Arg Asp
            20                  25                  30

Leu Ala Trp Tyr Gln Gln Lys Pro Gly Gln Ala Pro Glu Leu Leu Ile
        35                  40                  45

Tyr Gly Ala Ser Arg Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Ser Pro Leu Thr
                85                  90                  95

-continued

```
Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Glu Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Glu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

```
<210> SEQ ID NO 152
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 152
```

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Arg Leu Leu Ile
            35                  40                  45

Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Leu Thr
            85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Glu Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Glu Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

```
<210> SEQ ID NO 153
```

```
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 153

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Arg Leu Leu Ile
        35                  40                  45

Tyr Gly Ala Ser Thr Arg Glu Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Glu Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 154
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 154

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
```

```
              100              105              110

Pro Ser Val Phe Ile Phe Pro Pro Ser Asp Glu Gln Leu Lys Ser Gly
        115              120              125

Thr Ala Glu Val Val Cys Leu Leu Asn Asn Phe Tyr Pro Arg Glu Ala
    130              135              140

Lys Val Gln Trp Lys Val Asp Asn Ala Leu Gln Ser Gly Asn Ser Gln
145              150              155              160

Glu Ser Val Thr Glu Gln Asp Ser Lys Asp Ser Thr Tyr Ser Leu Ser
            165              170              175

Ser Thr Leu Glu Leu Ser Lys Ala Asp Tyr Glu Lys His Lys Val Tyr
            180              185              190

Ala Cys Glu Val Thr His Gln Gly Leu Ser Ser Pro Val Thr Lys Ser
        195              200              205

Phe Asn Arg Gly Glu Cys
    210

<210> SEQ ID NO 155
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 155

Glu Ile Val Leu Thr Gln Ser Pro Ala Thr Leu Ser Val Ser Pro Gly
1               5               10              15

Glu Arg Ala Thr Leu Ser Cys Arg Ala Thr Arg Ser Val Arg Arg Asp
            20              25              30

Leu Ala Trp Tyr Gln Lys Lys Pro Gly Gln Ala Pro Arg Leu Leu Ile
        35              40              45

Tyr Gly Ala Ser Arg Arg Glu Thr Gly Ile Pro Asp Arg Phe Ser Gly
        50              55              60

Ser Gly Ser Gly Thr Glu Phe Thr Leu Thr Ile Ser Ser Leu Glu Pro
65              70              75              80

Glu Asp Phe Ala Val Tyr Tyr Cys Gln Gln Tyr Arg Asp Pro Pro Gly
            85              90              95

Thr Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Glu Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Glu Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 156
<211> LENGTH: 214
<212> TYPE: PRT
```

<213> ORGANISM: Artificial Sequence
<220> FEATURE:
<223> OTHER INFORMATION: An artificially synthesized sequence

<400> SEQUENCE: 156

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Lys Lys Pro Gly Gln Ala Pro Arg Leu Leu Ile
        35                  40                  45

Tyr Gly Ala Ser Thr Arg Glu Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Glu Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 157
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 157

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
        35                  40                  45

Tyr Gly Ala Ser Thr Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Met Ala Val Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

-continued

```
Pro Ser Val Phe Ile Phe Pro Pro Ser Asp Glu Gln Leu Lys Ser Gly
        115                 120                 125

Thr Ala Glu Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 158
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 158

Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
                20                  25                  30

Leu Ala Trp Tyr Gln Lys Lys Pro Gly Gln Ala Pro Glu Leu Leu Ile
                35                  40                  45

Tyr Gly Ala Ser Thr Arg Glu Thr Gly Ile Pro Ala Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Glu Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 159
<211> LENGTH: 214
<212> TYPE: PRT
<213> ORGANISM: Artificial Sequence
<220> FEATURE:
```

-continued

<223> OTHER INFORMATION: An artificially synthesized sequence

<400> SEQUENCE: 159

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Arg Ser Val Arg Arg Glu
            20                  25                  30

Leu Ala Trp Tyr Gln Gln Lys Pro Gly Gln Ala Pro Glu Leu Leu Ile
            35                  40                  45

Tyr Gly Ala Ser Thr Arg Glu Thr Gly Ile Pro Ala Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Glu Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 160
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 160

```
Glu Ile Val Leu Thr Gln Ser Pro Ala Thr Leu Ser Val Ser Pro Gly
1               5                   10                  15

Glu Arg Ala Thr Leu Ser Cys Arg Ala Thr Arg Ser Val Arg Arg Asp
            20                  25                  30

Leu Ala Trp Tyr Gln Gln Lys Pro Gly Gln Ala Pro Glu Leu Leu Ile
            35                  40                  45

Tyr Gly Ala Ser Arg Arg Glu Thr Gly Ile Pro Ala Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Arg Asp Pro Pro Gly
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

-continued

```
Thr Ala Glu Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 161
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 161

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ser Asn Thr Arg Ser Gly Thr Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
                420                 425                 430

Ala His Tyr Thr Arg Glu Glu Leu Ser Leu Ser Pro
                435                 440
```

<210> SEQ ID NO 162
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 162

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Asn
                20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
        50                  55                  60

Gln Asn Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
                100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
                180                 185                 190
```

-continued

```
Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440
```

<210> SEQ ID NO 163
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 163

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Arg Val Ile Ser Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
            85                  90                  95

Ala Arg Arg Lys Ser Tyr Gly Tyr Tyr Leu Asp Glu Trp Gly Glu Gly
            100                 105                 110
```

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
        435                 440

<210> SEQ ID NO 164
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 164

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
                20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Val Ile Tyr Asn Glu Glu Phe
        50                  55                  60

Gln Gln Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
                180                 185                 190

Ser Ser Leu Gly Thr Gln Thr Tyr Thr Cys Asn Val Asp His Lys Pro
                195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
                420                 425                 430

Ala His Tyr Thr Arg Glu Glu Leu Ser Leu Ser Pro
        435                 440

<210> SEQ ID NO 165
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 165

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Gln Asn
            20                  25                  30

Asn Met Asp Trp Val Arg Lys Ala Pro Gly Gln Gly Leu Glu Trp Met
            35                  40                  45

Gly Asp Ile Asn Thr Arg Ser Gly Gly Val Ile Tyr Asn Glu Glu Phe
        50                  55                  60

Gln Asp Arg Leu Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365
```

-continued

```
Lys Gly Phe Tyr Pro Ser Asp Ile Ala Val Glu Trp Glu Ser Asn Gly
    370             375                 380

Gln Pro Glu Asn Asn Tyr Lys Thr Thr Pro Pro Val Leu Asp Ser Asp
385             390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440
```

```
<210> SEQ ID NO 166
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 166
```

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
            20                  25                  30

Asn Met Asp Trp Val Arg Lys Ala Pro Gly Gln Gly Leu Glu Trp Met
            35                  40                  45

Gly Asp Ile Asn Thr Arg Ser Gly Arg Ser Ile Tyr Asn Glu Glu Phe
    50                  55                  60

Gln Asp Arg Val Ile Met Thr Val Asp Ile Ser Thr Asp Thr Ala Tyr
65                  70                  75                  80

Met Glu Leu Ser Ser Leu Arg Ser Glu Asp Thr Ala Thr Tyr His Cys
            85                  90                  95

Ala Arg Arg Lys Ser Tyr Gly Tyr Tyr Leu Asp Val Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285
```

-continued

```
Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Gly Leu Pro Ser Ser Ile Glu Lys Thr Ile Ser
            325             330             335

Lys Ala Lys Gly Gln Pro Arg Glu Pro Gln Val Tyr Thr Leu Pro Pro
            340             345             350

Ser Gln Glu Glu Met Thr Lys Asn Gln Val Ser Leu Thr Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Glu Gly Asn Val Phe Ser Cys Ser Val Leu His Glu Ala Leu His
            420             425             430

Ala His Tyr Thr Arg Glu Glu Leu Ser Leu Ser Pro
            435             440
```

```
<210> SEQ ID NO 167
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 167
```

```
Gln Val Gln Leu Val Gln Ser Gly Ser Glu Leu Lys Lys Pro Gly Ala
1               5               10              15

Ser Val Lys Val Ser Cys Lys Ala Ser Gly Tyr Thr Phe Thr Gln Asn
            20              25              30

Asn Met Asp Trp Val Arg Gln Ala Pro Gly Gln Gly Leu Glu Trp Met
            35              40              45

Gly Asp Ile Asn Thr Arg Ser Gly Gly Val Ile Tyr Asn Glu Glu Phe
    50              55              60

Gln Asp Arg Leu Ile Met Thr Val Asp Lys Ser Thr Asp Thr Ala Tyr
65              70              75              80

Met Glu Leu Ser Ser Leu Arg Ser Glu Asp Thr Ala Thr Tyr His Cys
            85              90              95

Ala Arg Arg Lys Ser Tyr Gly Tyr Tyr Leu Asp Val Trp Gly Glu Gly
            100             105             110

Thr Leu Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
    130             135             140

Gly Cys Leu Val Glu Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Glu Ser Ser Gly Leu Tyr Ser Leu Ser Ser Val Val Thr Val Pro Ser
            180             185             190

Ser Ser Leu Gly Thr Gln Thr Tyr Thr Cys Asn Val Asp His Lys Pro
            195             200             205
```

-continued

```
Ser Asn Thr Lys Val Asp Lys Arg Val Glu Ser Lys Tyr Gly Pro Pro
    210             215             220

Cys Pro Pro Cys Pro Ala Pro Glu Phe Leu Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser Gln Glu Asp Pro Glu Val
            260             265             270

Gln Phe Asn Trp Tyr Val Asp Gly Val Glu Val His Asn Ala Lys Thr
            275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Gly Leu Pro Ser Ser Ile Glu Lys Thr Ile Ser
            325             330             335

Lys Ala Lys Gly Gln Pro Arg Glu Pro Gln Val Tyr Thr Leu Pro Pro
            340             345             350

Ser Gln Glu Glu Met Thr Lys Asn Gln Val Ser Leu Thr Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Glu Gly Asn Val Phe Ser Cys Ser Val Leu His Glu Ala Leu His
            420             425             430

Ala His Tyr Thr Arg Glu Glu Leu Ser Leu Ser Pro
            435             440
```

```
<210> SEQ ID NO 168
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 168
```

```
Gln Val Gln Leu Val Gln Ser Gly Ser Glu Leu Lys Lys Pro Gly Ala
1               5               10              15

Ser Val Lys Val Ser Cys Lys Ala Ser Gly Tyr Thr Phe Thr Gln Asn
            20              25              30

Asn Met Asp Trp Val Arg Lys Ala Pro Gly Gln Gly Leu Glu Trp Met
            35              40              45

Gly Asp Ile Asn Thr Arg Ser Gly Gly Val Ile Tyr Asn Glu Glu Phe
    50              55              60

Gln Asp Arg Leu Ile Met Thr Val Asp Lys Ser Thr Asp Thr Ala Tyr
65              70              75              80

Met Glu Leu Ser Ser Leu Arg Ser Glu Asp Thr Ala Thr Tyr His Cys
            85              90              95

Ala Arg Arg Lys Ser Tyr Gly Tyr Tyr Leu Asp Glu Trp Gly Glu Gly
            100             105             110

Thr Leu Val Thr Val Ser Ser Ala Ser Thr Lys Gly Pro Ser Val Phe
            115             120             125
```

```
Pro Leu Ala Pro Cys Ser Arg Ser Thr Ser Glu Ser Thr Ala Ala Leu
    130             135             140
```

```
Gly Cys Leu Val Glu Asp Tyr Phe Pro Glu Pro Val Thr Val Ser Trp
145             150             155             160
```

```
Asn Ser Gly Ala Leu Thr Ser Gly Val His Thr Phe Pro Ala Val Leu
            165             170             175
```

```
Glu Ser Ser Gly Leu Tyr Ser Leu Ser Ser Val Val Thr Val Pro Ser
            180             185             190
```

```
Ser Ser Leu Gly Thr Gln Thr Tyr Thr Cys Asn Val Asp His Lys Pro
        195             200             205
```

```
Ser Asn Thr Lys Val Asp Lys Arg Val Glu Ser Lys Tyr Gly Pro Pro
    210             215             220
```

```
Cys Pro Pro Cys Pro Ala Pro Glu Phe Leu Gly Gly Pro Ser Val Phe
225             230             235             240
```

```
Leu Phe Pro Pro Lys Pro Lys Asp Thr Leu Met Ile Ser Arg Thr Pro
            245             250             255
```

```
Glu Val Thr Cys Val Val Val Asp Val Ser Gln Glu Asp Pro Glu Val
            260             265             270
```

```
Gln Phe Asn Trp Tyr Val Asp Gly Val Glu Val His Asn Ala Lys Thr
    275             280             285
```

```
Lys Pro Arg Glu Glu Gln Tyr Asn Ser Thr Tyr Arg Val Val Ser Val
    290             295             300
```

```
Leu Thr Val Leu His Gln Asp Trp Leu Asn Gly Lys Glu Tyr Lys Cys
305             310             315             320
```

```
Lys Val Ser Asn Lys Gly Leu Pro Ser Ser Ile Glu Lys Thr Ile Ser
            325             330             335
```

```
Lys Ala Lys Gly Gln Pro Arg Glu Pro Gln Val Tyr Thr Leu Pro Pro
            340             345             350
```

```
Ser Gln Glu Glu Met Thr Lys Asn Gln Val Ser Leu Thr Cys Leu Val
            355             360             365
```

```
Lys Gly Phe Tyr Pro Ser Asp Ile Ala Val Glu Trp Glu Ser Asn Gly
    370             375             380
```

```
Gln Pro Glu Asn Asn Tyr Lys Thr Thr Pro Pro Val Leu Asp Ser Asp
385             390             395             400
```

```
Gly Ser Phe Phe Leu Tyr Ser Lys Leu Thr Val Asp Lys Ser Arg Trp
            405             410             415
```

```
Gln Glu Gly Asn Val Phe Ser Cys Ser Val Leu His Glu Ala Leu His
            420             425             430
```

```
Ala His Tyr Thr Arg Glu Glu Leu Ser Leu Ser Pro
            435             440
```

```
<210> SEQ ID NO 169
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 169
```

```
Gln Val Gln Leu Val Gln Ser Gly Ser Glu Leu Lys Lys Pro Gly Ala
1               5               10              15
```

```
Ser Val Lys Val Ser Cys Lys Ala Ser Gly Tyr Thr Phe Thr Gln Asn
            20              25              30
```

```
Asn Met Asp Trp Val Arg Gln Ala Pro Gly Gln Gly Leu Glu Trp Met
        35              40              45
```

-continued

```
Gly Asp Ile Asn Thr Arg Ser Gly Gly Val Ile Tyr Asn Glu Lys Phe
    50              55                  60

Gln Asp Arg Val Ile Met Thr Val Asp Lys Ser Thr Asp Thr Ala Tyr
65              70                  75                  80

Met Glu Leu Ser Glu Leu Arg Ser Glu Asp Thr Ala Thr Tyr His Cys
            85                  90                  95

Ala Arg Arg Lys Ser Tyr Gly Tyr Tyr Leu Asp Val Trp Gly Glu Gly
            100             105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130             135                 140

Gly Cys Leu Val Glu Asp Tyr Phe Pro Glu Pro Val Thr Val Ser Trp
145             150                 155                 160

Asn Ser Gly Ala Leu Thr Ser Gly Val His Thr Phe Pro Ala Val Leu
            165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
    210             215                 220

Cys Pro Pro Cys Pro Ala Pro Glu Phe Leu Gly Gly Pro Ser Val Phe
225             230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290             295                 300

Leu Thr Val Leu His Gln Asp Trp Leu Asn Gly Lys Glu Tyr Lys Cys
305             310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
            420                 425                 430

Ala His Tyr Thr Arg Glu Glu Leu Ser Leu Ser Pro
            435                 440
```

```
<210> SEQ ID NO 170
<211> LENGTH: 444
<212> TYPE: PRT
```

```
<213> ORGANISM: Artificial Sequence
<220> FEATURE:
<223> OTHER INFORMATION: An artificially synthesized sequence

<400> SEQUENCE: 170

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Glu Phe Thr His Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Arg Ser Ile Tyr Asn Arg Glu Phe
        50                  55                  60

Gln Asp Arg Val Ile Met Thr Val Asp Ile Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Glu Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
```

-continued

```
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
                420                 425                 430

Ala His Tyr Thr Arg Glu Glu Leu Ser Leu Ser Pro
                435                 440
```

<210> SEQ ID NO 171
<211> LENGTH: 444
<212> TYPE: PRT
<213> ORGANISM: Artificial Sequence
<220> FEATURE:
<223> OTHER INFORMATION: An artificially synthesized sequence

<400> SEQUENCE: 171

```
Gln Val Gln Leu Val Gln Ser Gly Ser Glu Leu Lys Lys Pro Gly Ala
1                 5                  10                 15

Ser Val Lys Val Ser Cys Lys Ala Ser Gly Tyr Thr Phe Thr Gln Asn
                20                 25                 30

Asn Met Asp Trp Val Arg Lys Ala Pro Gly Gln Gly Leu Glu Trp Met
                35                 40                 45

Gly Asp Ile Asn Thr Arg Ser Gly Gly Val Ile Tyr Asn Glu Glu Phe
        50                  55                  60

Gln Asp Arg Leu Ile Met Thr Val Asp Lys Ser Thr Asp Thr Ala Tyr
65                  70                  75                  80

Met Glu Leu Ser Glu Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Glu Ser Ser Gly Leu Tyr Ser Leu Ser Ser Val Val Thr Val Pro Ser
                180                 185                 190

Ser Ser Leu Gly Thr Gln Thr Tyr Thr Cys Asn Val Asp His Lys Pro
                195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
```

```
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Leu His Glu Ala Leu His
                420                 425                 430

Ala His Tyr Thr Arg Glu Glu Leu Ser Leu Ser Pro
                435                 440

<210> SEQ ID NO 172
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 172

Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
                20                  25                  30

His Trp Tyr His Gln Arg Pro Gly Gln Ala Pro Ile Leu Val Met Phe
                35                  40                  45

Arg Asp Ala Arg Arg Pro Ser Gly Ile Pro Glu Arg Leu Ser Gly Ser
                50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Lys Leu Val Cys Leu Ile Ser Asp Phe Tyr Pro Gly Ala
                130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
                180                 185                 190

Ser Cys Gln Val Thr His Glu Gly Ser Thr Val Glu Lys Thr Val Ala
                195                 200                 205

Pro Thr Glu Cys Ser
    210
```

```
<210> SEQ ID NO 173
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 173

Ser Tyr Val Leu Thr Gln Pro Val Ser Val Ser Val Ala Arg Gly Gln
1               5                   10                  15

Thr Ala Thr Ile Thr Cys Glu Gly Asn His Ile Gly Asp Lys His Val
                20                  25                  30

His Trp Tyr His Gln Arg Pro Gly Gln Ala Pro Ile Leu Val Met Phe
            35                  40                  45

Gln Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210

<210> SEQ ID NO 174
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 174

Ser Tyr Val Leu Thr Gln Pro Val Ser Val Ser Val Ala Arg Gly Gln
1               5                   10                  15

Thr Ala Thr Ile Thr Cys Thr Gly Asn His Ile Ser Asp Lys His Val
                20                  25                  30

His Trp Tyr His Gln Arg Pro Gly Gln Ala Pro Ile Leu Val Met Phe
            35                  40                  45

Gln Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Asp Tyr Thr
                85                  90                  95
```

-continued

```
Val Phe Gly Gly Gly Thr Lys Val Thr Val Val Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
            130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210
```

<210> SEQ ID NO 175
<211> LENGTH: 212
<212> TYPE: PRT
<213> ORGANISM: Artificial Sequence
<220> FEATURE:
<223> OTHER INFORMATION: An artificially synthesized sequence

<400> SEQUENCE: 175

```
Ser Tyr Val Leu Thr Gln Pro Val Ser Val Ser Val Ala Arg Gly Gln
1               5                   10                  15

Thr Ala Thr Ile Thr Cys Glu Gly Asn Gln Ile Ser Gln Lys Gln Val
            20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Gln Ala Gly
65                  70                  75                  80

Asp Glu Gly Asp Tyr Tyr Cys Gln Val Trp Asp Ser Ser Ala Val Val
                85                  90                  95

Phe Gly Gly Gly Thr Lys Val Thr Val Val Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Lys Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Lys Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210
```

<210> SEQ ID NO 176
<211> LENGTH: 213

```
<212> TYPE: PRT
<213> ORGANISM: Artificial Sequence
<220> FEATURE:
<223> OTHER INFORMATION: An artificially synthesized sequence

<400> SEQUENCE: 176

Ser Tyr Val Leu Thr Gln Pro Val Ser Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Glu Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Tyr Thr
                85                  90                  95

Val Phe Gly Gly Gly Thr Lys Val Thr Val Val Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
        210

<210> SEQ ID NO 177
<211> LENGTH: 212
<212> TYPE: PRT
<213> ORGANISM: Artificial Sequence
<220> FEATURE:
<223> OTHER INFORMATION: An artificially synthesized sequence

<400> SEQUENCE: 177

Ser Tyr Val Leu Thr Gln Pro Val Ser Val Ser Val Ala Leu Gly Gln
1               5                   10                  15

Thr Ala Thr Ile Thr Cys Glu Gly Asn Gln Ile Gly Ser Arg Glu Val
                20                  25                  30

His Trp Tyr His Glu Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                85                  90                  95

Phe Gly Gly Gly Thr Lys Val Thr Val Val Gly Gln Pro Lys Ala Ala
                100                 105                 110
```

```
Pro Ser Val Thr Leu Phe Pro Pro Ser Ser Glu Glu Leu Gln Ala Asn
        115                 120                 125

Lys Ala Lys Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Lys Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 178
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 178

```
Ser Tyr Val Leu Thr Gln Pro Val Ser Val Ser Val Ala Leu Gly Gln
1               5                   10                  15

Thr Ala Thr Ile Thr Cys Glu Gly Glu Gln Ile Gly Ser Lys Glu Val
                20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Lys Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 179
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 179

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Ile Tyr
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210

<210> SEQ ID NO 180
<211> LENGTH: 213
<212> TYPE: PRT
<213> ORGANISM: Artificial Sequence
<220> FEATURE:
<223> OTHER INFORMATION: An artificially synthesized sequence

<400> SEQUENCE: 180

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Gln Arg Pro Gly Gln Ala Pro Ile Leu Val Ile Tyr
        35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val Gly Gln Pro Lys Ala
            100                 105                 110

Ala Pro Ser Val Thr Leu Phe Pro Pro Ser Ser Glu Glu Leu Gln Ala

-continued

```
             115                 120                 125

Asn Lys Ala Lys Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210
```

<210> SEQ ID NO 181
<211> LENGTH: 212
<212> TYPE: PRT
<213> ORGANISM: Artificial Sequence
<220> FEATURE:
<223> OTHER INFORMATION: An artificially synthesized sequence

<400> SEQUENCE: 181

```
Ser Tyr Glu Leu Thr Gln Pro Pro Ser Val Ser Val Ala Leu Gly Gln
1               5                   10                  15

Thr Ala Thr Ile Thr Cys Glu Gly Asn Gln Ile Gly Glu Lys Glu Val
                20                  25                  30

His Trp Tyr His Gln Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
    50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Ala Ser Asp Ala Val Val
                85                  90                  95

Phe Gly Gly Gly Thr Lys Val Thr Val Val Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Lys Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Lys Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210
```

<210> SEQ ID NO 182
<211> LENGTH: 213
<212> TYPE: PRT
<213> ORGANISM: Artificial Sequence
<220> FEATURE:
<223> OTHER INFORMATION: An artificially synthesized sequence -continued

```
<400> SEQUENCE: 182

Ser Tyr Glu Leu Thr Gln Pro Pro Ser Val Ser Val Ala Leu Gly Gln
1               5                   10                  15

Thr Ala Thr Ile Thr Cys Glu Gly Glu Gln Ile Gly Ser Lys Glu Val
            20                  25                  30

His Trp Tyr His Glu Arg Pro Gly Gln Ala Pro Ile Leu Val Met Phe
            35                  40                  45

Arg Asp Ala Arg Arg Pro Ser Gly Ile Pro Glu Arg Leu Ser Gly Ser
        50                  55                  60

Asn Ser Gly Asn Thr Ala Ser Leu Thr Ile Ser Gly Ala Glu Ala Gly
65                  70                  75                  80

Asp Glu Gly Asp Tyr Tyr Cys Gln Val Trp Asp Ser Ser Ser Tyr Thr
                85                  90                  95

Val Phe Gly Gly Gly Thr Lys Val Thr Val Val Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Lys Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Lys Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
        210
```